United States Patent
Hennrich et al.

(10) Patent No.: US 11,268,636 B2
(45) Date of Patent: Mar. 8, 2022

(54) FEATURES FOR CABLE MANAGERS AND OTHER ELECTRONIC EQUIPMENT STRUCTURES

(71) Applicant: CHATSWORTH PRODUCTS, INC., Agoura Hills, CA (US)

(72) Inventors: Preston Ellis Hennrich, Leander, TX (US); John W. Robertson, Georgetown, TX (US); Johnny C. Fraga, Round Rock, TX (US)

(73) Assignee: Chatsworth Products, Inc., Agoura Hills, CA (US)

( * ) Notice: Subject to any disclaimer, the term of this patent is extended or adjusted under 35 U.S.C. 154(b) by 0 days.

(21) Appl. No.: 16/983,973

(22) Filed: Aug. 3, 2020

(65) Prior Publication Data

US 2020/0367382 A1  Nov. 19, 2020

Related U.S. Application Data

(63) Continuation of application No. 16/203,050, filed on Nov. 28, 2018, now Pat. No. 11,071,227, which is a
(Continued)

(51) Int. Cl.
*F16L 3/24* (2006.01)
*H02G 3/04* (2006.01)
(Continued)

(52) U.S. Cl.
CPC ............... *F16L 3/24* (2013.01); *E05C 9/041* (2013.01); *E05D 15/502* (2013.01); *E05D 15/56* (2013.01);
(Continued)

(58) Field of Classification Search
CPC ......... F16L 3/24; F16L 3/2431; G02B 6/4452; G02B 6/3897; G02B 6/4471; G02B 6/4478
(Continued)

(56) References Cited

U.S. PATENT DOCUMENTS

| 2,212,156 A | 8/1940 | Erdley |
| 2,537,928 A | 1/1951 | Churchill |

(Continued)

FOREIGN PATENT DOCUMENTS

| AU | 322233 | 11/2008 |
| CN | ZL200830139490.9 | 11/2009 |

(Continued)

OTHER PUBLICATIONS

Information Disclosure Statement (IDS) Letter Regarding Common Patent Application(s), dated May 17, 2021.
(Continued)

*Primary Examiner* — Christopher Garft
(74) *Attorney, Agent, or Firm* — Tillman Wright, PLLC; James D. Wright; David R. Higgins

(57) ABSTRACT

A cable manager includes a backbone assembly and at least one side wall extending from the backbone assembly. The at least one side wall optionally includes one or more cable finger units. The backbone assembly includes a spine member having an extruded construction. The spine member includes one or more channels extending substantially an entire length thereof to facilitate easy attachment, removal and/or repositioning of a structure relative to the spine member. The cable manager optionally includes an accessory rod, a half-spool assembly, a cable finger accessory, a strap/buckle accessory, and/or a door assembly having an interference-free hinge set.

7 Claims, 55 Drawing Sheets

Related U.S. Application Data continuation of application No. 15/843,879, filed on Dec. 15, 2017, now Pat. No. 10,271,452, which is a continuation of application No. PCT/US2017/043892, filed on Jul. 26, 2017, said application No. 16/203,050 is a continuation of application No. PCT/US2017/043892, filed on Jul. 26, 2017.

(60) Provisional application No. 62/366,900, filed on Jul. 26, 2016.

(51) Int. Cl.

| | | |
|---|---|---|
| H04Q 1/02 | (2006.01) | |
| H04Q 1/06 | (2006.01) | |
| H05K 7/14 | (2006.01) | |
| E05C 9/04 | (2006.01) | |
| E05D 15/50 | (2006.01) | |
| E05D 15/56 | (2006.01) | |
| E05F 1/06 | (2006.01) | |
| E05F 1/12 | (2006.01) | |
| F16B 2/22 | (2006.01) | |
| F16L 3/12 | (2006.01) | |
| F16L 3/137 | (2006.01) | |
| F16L 3/18 | (2006.01) | |
| F16L 3/22 | (2006.01) | |
| F16L 3/233 | (2006.01) | |
| F16L 3/26 | (2006.01) | |
| H05K 7/16 | (2006.01) | |
| G16H 10/00 | (2018.01) | |
| F16B 2/10 | (2006.01) | |
| F16B 2/18 | (2006.01) | |
| F16B 37/04 | (2006.01) | |

(52) U.S. Cl.
CPC ............ *E05F 1/068* (2013.01); *E05F 1/1207* (2013.01); *F16B 2/22* (2013.01); *F16L 3/1215* (2013.01); *F16L 3/137* (2013.01); *F16L 3/18* (2013.01); *F16L 3/221* (2013.01); *F16L 3/233* (2013.01); *F16L 3/2431* (2019.08); *F16L 3/26* (2013.01); *G16H 10/00* (2018.01); *H02G 3/04* (2013.01); *H02G 3/045* (2013.01); *H04Q 1/02* (2013.01); *H04Q 1/06* (2013.01); *H05K 7/1488* (2013.01); *H05K 7/1491* (2013.01); *H05K 7/16* (2013.01); *E05Y 2900/606* (2013.01); *F16B 2/10* (2013.01); *F16B 2/185* (2013.01); *F16B 37/045* (2013.01)

(58) Field of Classification Search
USPC .................. 248/231.81, 228.7, 72, 67.5; 385/134–136
See application file for complete search history.

(56) References Cited

U.S. PATENT DOCUMENTS

| | | |
|---|---|---|
| 2,921,607 A | 1/1960 | Caveney |
| 3,485,937 A | 12/1969 | Caveney |
| 3,518,727 A | 7/1970 | Eberle et al. |
| 3,705,737 A | 12/1972 | Westerlund et al. |
| 3,828,403 A | 8/1974 | Perrin et al. |
| 3,913,187 A | 10/1975 | Okuda |
| 4,123,095 A | 10/1978 | Stehlin |
| 4,478,381 A | 10/1984 | Pittion et al. |
| 4,497,411 A | 2/1985 | DeBortoli |
| 4,501,458 A | 2/1985 | Cubbage |
| 4,524,937 A | 6/1985 | Zizan |
| 4,573,717 A | 3/1986 | Peacock |
| 4,613,174 A | 9/1986 | Berg et al. |
| 4,639,979 A | 2/1987 | Polson |
| 4,783,029 A | 11/1988 | Geppert et al. |
| 4,962,652 A | 10/1990 | Schneider |
| 4,998,757 A | 3/1991 | Ramsauer |
| 5,165,770 A | 11/1992 | Hahn |
| 5,359,866 A | 11/1994 | Boddy |
| 5,398,339 A | 3/1995 | Wagner |
| 5,441,307 A | 8/1995 | Quintana et al. |
| 5,538,208 A | 7/1996 | Cordes et al. |
| 5,570,940 A | 11/1996 | Maro |
| 5,580,014 A | 12/1996 | Rinderer |
| 5,580,181 A | 12/1996 | Nomura |
| 5,586,012 A | 12/1996 | Lerman |
| 5,640,482 A | 6/1997 | Barry et al. |
| 5,655,865 A | 8/1997 | Plank et al. |
| 5,704,574 A | 1/1998 | Kasubke |
| 5,806,811 A | 9/1998 | Viklund et al. |
| 5,806,945 A | 9/1998 | Anderson et al. |
| 5,902,961 A | 5/1999 | Viklund et al. |
| 5,934,485 A | 8/1999 | Harris et al. |
| 6,017,104 A | 1/2000 | Foschino et al. |
| 6,047,838 A | 4/2000 | Rindoks et al. |
| 6,082,837 A | 7/2000 | Battochio et al. |
| 6,102,214 A | 8/2000 | Mendoza |
| 6,123,400 A | 9/2000 | Nicolai et al. |
| 6,129,316 A | 10/2000 | Bauer |
| 6,188,826 B1 * | 2/2001 | Daoud ............... G02B 6/4442 385/135 |
| 6,201,919 B1 | 3/2001 | Puetz et al. |
| 6,238,029 B1 | 5/2001 | Marzec et al. |
| 6,293,637 B1 | 9/2001 | Anderson et al. |
| 6,347,714 B1 | 2/2002 | Fournier et al. |
| 6,365,834 B1 | 4/2002 | Larsen et al. |
| 6,401,940 B1 | 6/2002 | Hartel et al. |
| 6,446,913 B1 | 9/2002 | Schroeder |
| 6,467,633 B1 | 10/2002 | Mendoza |
| 6,468,112 B1 | 10/2002 | Follingstad et al. |
| 6,481,160 B1 | 11/2002 | Kowalczyk |
| 6,489,565 B1 | 12/2002 | Krietzman et al. |
| 6,501,899 B1 | 12/2002 | Marrs et al. |
| 6,513,770 B1 | 2/2003 | Franz et al. |
| 6,517,174 B2 | 2/2003 | Sevier |
| 6,527,351 B1 | 3/2003 | Sevier et al. |
| 6,535,681 B2 * | 3/2003 | Daoud ............... G02B 6/4452 385/134 |
| 6,546,179 B2 * | 4/2003 | Petri ................. G02B 6/4457 385/134 |
| 6,561,602 B1 | 5/2003 | Sevier et al. |
| 6,584,267 B1 | 6/2003 | Caveney et al. |
| 6,605,782 B1 | 8/2003 | Krietzman et al. |
| 6,614,665 B2 | 9/2003 | Witty et al. |
| 6,614,978 B1 | 9/2003 | Caveney et al. |
| 6,708,830 B2 | 3/2004 | Mendoza |
| 6,760,531 B1 | 7/2004 | Solheid et al. |
| 6,766,093 B2 | 7/2004 | McGrath et al. |
| 6,785,459 B2 * | 8/2004 | Schmidt ............. G02B 6/4471 211/26 |
| 6,796,437 B2 | 9/2004 | Krampotich et al. |
| 6,796,438 B2 | 9/2004 | Mendoza |
| 6,884,942 B2 | 4/2005 | McGrath et al. |
| 6,918,796 B2 | 7/2005 | Elliot et al. |
| 6,920,038 B2 | 7/2005 | Gehlbach |
| 6,946,605 B2 | 9/2005 | Levesque et al. |
| 6,964,588 B2 | 11/2005 | Follingstad et al. |
| 6,968,647 B2 | 11/2005 | Levesque et al. |
| 6,980,726 B2 * | 12/2005 | Daoud ............... G02B 6/4452 385/136 |
| 6,981,893 B2 | 1/2006 | Barker et al. |
| 7,000,784 B2 | 2/2006 | Canty et al. |
| 7,019,213 B1 | 3/2006 | McNutt et al. |
| 7,026,553 B2 | 4/2006 | Levesque et al. |
| 7,060,893 B1 | 6/2006 | Villi |
| 7,083,051 B2 | 8/2006 | Smith et al. |
| 7,119,282 B2 | 10/2006 | Krietzman et al. |
| 7,142,765 B2 | 11/2006 | Rapp et al. |
| 7,144,320 B2 | 12/2006 | Turek et al. |
| 7,152,936 B2 | 12/2006 | Tarasewicz |
| 7,154,748 B2 | 12/2006 | Yamada |
| 7,172,078 B2 | 2/2007 | Abby et al. |
| 7,178,679 B2 | 2/2007 | Canty et al. |

(56) References Cited

U.S. PATENT DOCUMENTS

| | | |
|---|---|---|
| 7,210,319 B2 | 5/2007 | Artsiely |
| 7,220,150 B2 | 5/2007 | Follingstad et al. |
| 7,225,586 B2 | 6/2007 | Levesque et al. |
| 7,268,998 B2 | 9/2007 | Ewing et al. |
| 7,285,027 B2 | 10/2007 | McGrath et al. |
| 7,293,666 B2 | 11/2007 | Mattlin et al. |
| 7,312,980 B2 | 12/2007 | Ewing et al. |
| 7,344,113 B2 | 3/2008 | Tsai |
| 7,359,610 B2 * | 4/2008 | Vongseng .......... G02B 6/4452 385/134 |
| 7,362,941 B2 | 4/2008 | Rinderer et al. |
| 7,378,046 B2 | 5/2008 | Canty et al. |
| 7,381,100 B2 | 6/2008 | Follingstad et al. |
| 7,417,188 B2 | 8/2008 | McNutt et al. |
| 7,425,678 B2 | 9/2008 | Adducci et al. |
| 7,427,713 B2 | 9/2008 | Adducci et al. |
| 7,437,048 B2 | 10/2008 | Farrell et al. |
| 7,458,859 B2 | 12/2008 | McGrath et al. |
| 7,472,970 B2 | 1/2009 | Bergesch et al. |
| 7,476,804 B2 | 1/2009 | Adducci et al. |
| 7,485,803 B2 | 2/2009 | Adducci et al. |
| 7,495,169 B2 | 2/2009 | Adducci et al. |
| 7,498,512 B2 | 3/2009 | Adducci et al. |
| 7,504,581 B2 | 3/2009 | Adducci et al. |
| 7,592,541 B2 | 9/2009 | Adducci et al. |
| 7,600,724 B2 | 10/2009 | Nelson et al. |
| 7,608,779 B2 | 10/2009 | Adducci et al. |
| 7,667,135 B2 | 2/2010 | Adducci et al. |
| D611,326 S | 3/2010 | Alaniz et al. |
| 7,718,891 B2 | 5/2010 | Adducci et al. |
| 7,762,405 B2 | 7/2010 | Vogel et al. |
| 7,772,489 B2 | 8/2010 | Adducci et al. |
| 7,778,513 B2 | 8/2010 | Rinderer et al. |
| 7,781,675 B2 | 8/2010 | Adducci et al. |
| 7,795,532 B2 | 9/2010 | Walker |
| 7,880,084 B2 | 2/2011 | Adducci et al. |
| 7,893,356 B2 | 2/2011 | Garza et al. |
| 7,900,324 B2 | 3/2011 | Ginocchio |
| 7,913,957 B2 | 3/2011 | Nelson et al. |
| 7,939,763 B2 | 5/2011 | Jones et al. |
| 7,944,692 B2 | 5/2011 | Grantham et al. |
| 7,973,242 B2 | 7/2011 | Jones et al. |
| 7,974,105 B2 | 7/2011 | Dean, Jr. et al. |
| 7,999,183 B2 | 8/2011 | Garza et al. |
| 8,003,890 B2 | 8/2011 | Donowho et al. |
| 8,014,171 B2 | 9/2011 | Kelly et al. |
| 8,035,965 B2 | 10/2011 | Adducci et al. |
| 8,138,419 B2 | 3/2012 | Garza et al. |
| 8,237,052 B2 | 8/2012 | Adducci et al. |
| 8,263,867 B2 | 9/2012 | Garza et al. |
| 8,273,989 B2 | 9/2012 | Garza et al. |
| 8,330,043 B2 | 12/2012 | Alaniz et al. |
| 8,405,982 B2 | 3/2013 | Grantham et al. |
| 8,411,465 B2 | 4/2013 | Dean, Jr. et al. |
| 8,424,691 B2 | 4/2013 | McMillan, III et al. |
| 8,424,814 B2 * | 4/2013 | Davis ................ H02G 3/0608 248/49 |
| 8,437,147 B2 | 5/2013 | Dean, Jr. et al. |
| 8,558,113 B2 | 10/2013 | Krietzman et al. |
| 8,573,482 B1 | 11/2013 | Lute et al. |
| 8,596,601 B1 | 12/2013 | Anderson |
| 8,710,369 B2 | 4/2014 | Krietzman et al. |
| 8,730,678 B1 | 5/2014 | Cunningham et al. |
| 8,844,888 B1 | 9/2014 | Gretz |
| 9,054,506 B2 | 6/2015 | Krietzman et al. |
| 9,146,375 B2 * | 9/2015 | Terry .................. G02B 6/46 |
| 9,248,941 B1 | 2/2016 | Legel et al. |
| 9,270,097 B2 | 2/2016 | Krietzman et al. |
| 9,304,549 B2 | 4/2016 | Siddiqui |
| 9,350,146 B2 | 5/2016 | Krietzman et al. |
| 9,351,427 B2 | 5/2016 | Lewis, II et al. |
| 9,363,922 B2 | 6/2016 | Larsen et al. |
| 9,420,727 B2 | 8/2016 | Lewis, II et al. |
| 9,549,482 B2 | 1/2017 | Podemski et al. |
| 9,549,487 B2 | 1/2017 | Lewis, II et al. |
| 9,556,976 B1 | 1/2017 | Thompson et al. |
| 9,572,286 B2 * | 2/2017 | Greeson ................ B60J 10/24 |
| 9,577,414 B2 | 2/2017 | Krietzman et al. |
| 9,627,860 B2 | 4/2017 | Proserpio et al. |
| 9,795,060 B2 | 10/2017 | Greeson et al. |
| 9,814,150 B2 | 11/2017 | Krietzman et al. |
| 9,829,019 B2 | 11/2017 | McFadden |
| 9,899,812 B2 | 2/2018 | Krietzman et al. |
| 9,949,406 B2 | 4/2018 | Lewis, II et al. |
| 9,969,110 B2 | 5/2018 | Chen et al. |
| 9,986,655 B1 | 5/2018 | Stoner et al. |
| 10,003,180 B1 | 6/2018 | Krietzman |
| 10,037,057 B2 | 7/2018 | Schafer et al. |
| 10,039,423 B2 | 8/2018 | Schultz et al. |
| 10,072,794 B2 | 9/2018 | Koch |
| 10,237,994 B2 | 3/2019 | Donowho et al. |
| 10,271,452 B2 | 4/2019 | Hennrich et al. |
| 10,274,691 B2 | 4/2019 | Janssens et al. |
| 10,281,070 B2 | 5/2019 | Kuo et al. |
| 10,436,362 B2 | 10/2019 | Ahrens et al. |
| 10,477,720 B2 | 11/2019 | Hennrich et al. |
| 10,508,668 B2 | 12/2019 | Ikushima |
| 10,588,227 B2 | 3/2020 | Donowho et al. |
| 10,674,634 B2 | 6/2020 | Lewis, II et al. |
| 10,797,441 B2 | 10/2020 | Utz et al. |
| 11,071,227 B2 | 7/2021 | Hennrich et al. |
| 11,083,108 B2 | 8/2021 | Lewis, II et al. |
| 11,133,656 B2 | 9/2021 | Krietzman et al. |
| 11,162,615 B2 | 11/2021 | Hennrich et al. |
| 2001/0022231 A1 | 9/2001 | Dyer |
| 2002/0097973 A1 * | 7/2002 | Petri .................. G02B 6/4457 385/134 |
| 2002/0121571 A1 * | 9/2002 | Ferris ................ H02G 3/0406 242/615 |
| 2002/0138947 A1 | 10/2002 | Jantschek |
| 2002/0191936 A1 * | 12/2002 | Daoud ................ H04N 5/32 385/134 |
| 2002/0197045 A1 * | 12/2002 | Schmidt ............. H04Q 1/066 385/134 |
| 2003/0020379 A1 | 1/2003 | Larsen et al. |
| 2004/0007372 A1 | 1/2004 | Krietzman et al. |
| 2004/0037533 A1 | 2/2004 | Knudsen |
| 2004/0050808 A1 | 3/2004 | Krampotich et al. |
| 2004/0094491 A1 | 5/2004 | Smith et al. |
| 2004/0146266 A1 | 7/2004 | Solheid et al. |
| 2004/0173545 A1 | 9/2004 | Canty et al. |
| 2004/0226900 A1 | 11/2004 | Canty et al. |
| 2004/0240828 A1 * | 12/2004 | Daoud ................ G02B 6/4452 385/136 |
| 2004/0247277 A1 * | 12/2004 | Spayes ................ G02B 6/4452 385/135 |
| 2005/0006323 A1 | 1/2005 | Abby et al. |
| 2005/0103517 A1 | 5/2005 | Canepa |
| 2005/0115152 A1 | 6/2005 | Levesque et al. |
| 2005/0115736 A1 | 6/2005 | Levesque et al. |
| 2005/0115737 A1 | 6/2005 | Levesque et al. |
| 2005/0116129 A1 * | 6/2005 | Boudreau ............ F16L 3/245 248/228.7 |
| 2005/0193530 A1 | 9/2005 | Boda |
| 2005/0221683 A1 | 10/2005 | McGrath et al. |
| 2005/0247650 A1 | 11/2005 | Vogel et al. |
| 2005/0259383 A1 | 11/2005 | Ewing |
| 2005/0283049 A1 | 12/2005 | Seki et al. |
| 2005/0284991 A1 | 12/2005 | Saez |
| 2006/0054336 A1 | 3/2006 | McNutt et al. |
| 2006/0059802 A1 | 3/2006 | McNutt et al. |
| 2006/0080933 A1 * | 4/2006 | Robicheau ............ F16L 3/24 52/712 |
| 2006/0091086 A1 | 5/2006 | Canty et al. |
| 2006/0162948 A1 | 7/2006 | Rinderer et al. |
| 2007/0072456 A1 | 3/2007 | Zweers |
| 2007/0114338 A1 * | 5/2007 | Boudreau ............ F16L 3/245 248/58 |
| 2007/0210679 A1 | 9/2007 | Adducci et al. |
| 2007/0210680 A1 | 9/2007 | Appino et al. |
| 2007/0210681 A1 | 9/2007 | Adducci et al. |
| 2007/0210683 A1 | 9/2007 | Adducci et al. |
| 2007/0210686 A1 | 9/2007 | Adducci et al. |

(56) References Cited

U.S. PATENT DOCUMENTS

| | | | |
|---|---|---|---|
| 2007/0212010 A1 | 9/2007 | Caveney et al. | |
| 2007/0221393 A1 | 9/2007 | Adducci et al. | |
| 2007/0230887 A1* | 10/2007 | Vongseng | G02B 6/4452 385/134 |
| 2007/0249237 A1 | 10/2007 | Follingstad et al. | |
| 2007/0257159 A1 | 11/2007 | Nelson et al. | |
| 2007/0293138 A1 | 12/2007 | Adducci et al. | |
| 2008/0035821 A1 | 2/2008 | Kameoka et al. | |
| 2008/0062654 A1 | 3/2008 | Mattlin et al. | |
| 2008/0067904 A1 | 3/2008 | Adducci et al. | |
| 2008/0074849 A1 | 3/2008 | Adducci et al. | |
| 2008/0130262 A1 | 6/2008 | Rinderer et al. | |
| 2008/0151524 A1 | 6/2008 | Kelly et al. | |
| 2008/0174217 A1 | 7/2008 | Walker | |
| 2008/0203241 A1* | 8/2008 | Boudreau | F16L 3/245 248/58 |
| 2008/0265106 A1* | 10/2008 | Boudreau | F16L 3/26 248/72 |
| 2008/0271918 A1 | 11/2008 | Caveney et al. | |
| 2009/0014614 A1 | 1/2009 | Warmoth et al. | |
| 2009/0090533 A1 | 4/2009 | Jones et al. | |
| 2009/0090538 A1 | 4/2009 | Jones et al. | |
| 2009/0093169 A1 | 4/2009 | McGrath et al. | |
| 2009/0165250 A1 | 7/2009 | Duan et al. | |
| 2009/0206217 A1 | 8/2009 | Wilson et al. | |
| 2009/0224110 A1 | 9/2009 | Donowho et al. | |
| 2009/0235494 A1 | 9/2009 | Browne et al. | |
| 2009/0236117 A1 | 9/2009 | Garza et al. | |
| 2009/0249590 A1 | 10/2009 | Maroso | |
| 2009/0273915 A1 | 11/2009 | Dean, Jr. et al. | |
| 2009/0283488 A1 | 11/2009 | McMillan, III et al. | |
| 2010/0101820 A1 | 4/2010 | Alaniz et al. | |
| 2010/0122830 A1 | 5/2010 | Garza et al. | |
| 2010/0126750 A1 | 5/2010 | Garza et al. | |
| 2010/0126751 A1 | 5/2010 | Garza et al. | |
| 2010/0193754 A1 | 8/2010 | Garza et al. | |
| 2010/0200707 A1 | 8/2010 | Garza et al. | |
| 2010/0236298 A1 | 9/2010 | James et al. | |
| 2011/0011612 A1 | 1/2011 | Sayres | |
| 2011/0056895 A1 | 3/2011 | Tichy | |
| 2011/0100668 A1 | 5/2011 | Syed | |
| 2011/0174534 A1 | 7/2011 | Krietzman et al. | |
| 2011/0180295 A1 | 7/2011 | Krietzman et al. | |
| 2011/0211328 A1 | 9/2011 | Dean, Jr. et al. | |
| 2011/0211329 A1 | 9/2011 | Dean, Jr. et al. | |
| 2011/0253647 A1 | 10/2011 | Yu et al. | |
| 2012/0080984 A1 | 4/2012 | Watts | |
| 2012/0145655 A1 | 6/2012 | McMillan, III et al. | |
| 2014/0097020 A1 | 4/2014 | Krietzman et al. | |
| 2014/0190721 A1 | 7/2014 | Krietzman et al. | |
| 2014/0196394 A1 | 7/2014 | Greeson et al. | |
| 2014/0242835 A1 | 8/2014 | Moran et al. | |
| 2014/0360752 A1 | 12/2014 | Sechrist et al. | |
| 2015/0008810 A1 | 1/2015 | Ivey et al. | |
| 2015/0030300 A1* | 1/2015 | Terry | G02B 6/4478 385/135 |
| 2015/0173253 A1 | 6/2015 | Lewis, II et al. | |
| 2015/0249326 A1 | 9/2015 | Krietzman et al. | |
| 2015/0264839 A1 | 9/2015 | Lewis, II et al. | |
| 2015/0282390 A1 | 10/2015 | Lewis, II et al. | |
| 2015/0282883 A1 | 10/2015 | Turturro et al. | |
| 2016/0088773 A1 | 3/2016 | Greeson et al. | |
| 2016/0174402 A1 | 6/2016 | Krietzman et al. | |
| 2016/0268788 A1 | 9/2016 | Krietzman et al. | |
| 2017/0127570 A1 | 5/2017 | Lewis, II et al. | |
| 2017/0150652 A1 | 5/2017 | Greeson et al. | |
| 2017/0155235 A1 | 6/2017 | Krietzman et al. | |
| 2018/0035570 A1 | 2/2018 | Greeson et al. | |
| 2018/0110153 A1 | 4/2018 | Hennrich et al. | |
| 2018/0166868 A1 | 6/2018 | Krietzman et al. | |
| 2018/0340333 A1 | 11/2018 | Hirth | |
| 2019/0098791 A1 | 3/2019 | Hennrich et al. | |
| 2019/0098792 A1 | 3/2019 | Hennrich et al. | |
| 2019/0162228 A1 | 5/2019 | Chen | |
| 2019/0296530 A1 | 9/2019 | Krietzman et al. | |
| 2019/0343023 A1 | 11/2019 | Lewis, II et al. | |
| 2019/0350108 A1 | 11/2019 | Davis | |
| 2019/0383431 A1 | 12/2019 | Magagna et al. | |
| 2020/0018334 A1 | 1/2020 | Le Mon et al. | |
| 2020/0077534 A1 | 3/2020 | Hennrich et al. | |
| 2020/0205317 A1 | 6/2020 | Davis | |
| 2020/0220303 A1 | 7/2020 | Utz et al. | |
| 2020/0288605 A1 | 9/2020 | Lewis, II et al. | |
| 2020/0367381 A1 | 11/2020 | Hennrich et al. | |
| 2020/0383230 A1 | 12/2020 | Hennrich et al. | |
| 2021/0329808 A1 | 10/2021 | Hennrich et al. | |
| 2021/0385976 A1 | 12/2021 | Lewis, II et al. | |

FOREIGN PATENT DOCUMENTS

| | | |
|---|---|---|
| CN | 102177633 A | 9/2011 |
| EC | 000968607-0001 | 7/2008 |
| GB | 2468823 A | 9/2010 |
| GB | 2468823 B | 10/2012 |
| IN | 216981 | 7/2009 |
| MX | 27994 | 4/2009 |
| SE | 535066 C2 | 4/2012 |
| WO | 2001074091 A2 | 10/2001 |
| WO | 2005112477 A1 | 11/2005 |
| WO | 2009089306 A1 | 7/2009 |
| WO | 2009089307 A2 | 7/2009 |
| WO | 2009143193 A2 | 11/2009 |
| WO | 2009089307 A3 | 12/2009 |
| WO | 2009143193 A3 | 3/2010 |
| WO | 2009089306 A4 | 6/2011 |
| WO | 2011088430 A2 | 7/2011 |
| WO | 2011088438 A2 | 7/2011 |
| WO | 2011088430 A3 | 11/2011 |
| WO | 2011088438 A3 | 11/2011 |
| WO | 2018022721 A1 | 2/2018 |

OTHER PUBLICATIONS

Information Disclosure Statement (IDS) Letter Regarding Common Patent Application(s), dated Sep. 8, 2020.

"International Search Report" and "Written Opinion of the International Search Authority" (Australian Patent Office) in Chatsworth Products, Inc. et al., International Patent Application Serial No. PCT/US2009/030368, dated Apr. 8, 2009 (20 pages).

"International Search Report" and "Written Opinion of the International Search Authority" (European Patent Office) in Corning Cable Systems LLC, International Patent Application Serial No. PCT/US2009/000075, dated Aug. 7, 2009 (21 pages).

"International Search Report" and "Written Opinion of the International Search Authority" (ISA/US) in Chatsworth Products, Inc., International Patent Application Serial No. PCT/US2017/043892, dated Nov. 16, 2017 (12 pages).

Rack Technologies Pty Ltd, Product Catalog, Internet Web Page <http://racktechnologies.com.au/files/rt2005.pdf>, Jun. 16, 2005, retrieved from Internet Archive Wayback Machine <http://web.archive.org/web/20050616212856/http://racktechnologies.com.au/files/rt2005.pdf> as reviewed as of Apr. 29, 2016 (73 pages).

"International Preliminary Report on Patentability" of the International Search Authority (ISA/US) in Chatsworth Products, Inc., International Patent Application Serial No. PCT/US2017/043892, dated Jan. 29, 2019 (8 pages).

Hewlett-Packard Development Company, LP, HP 10000 G2 42U Rack Air Duct Installation Guide, dated Aug. 2008 (23 pages).

Information Disclosure Statement (IDS) Letter Regarding Common Patent Application(s), dated Jul. 26, 2021.

Information Disclosure Statement (IDS) Letter Regarding Common Patent Application(s), dated Oct. 22, 2021.

Information Disclosure Statement (IDS) Letter Regarding Common Patent Application(s), dated Jan. 5, 2022.

\* cited by examiner

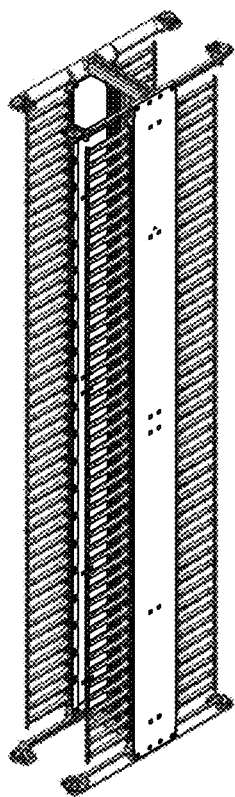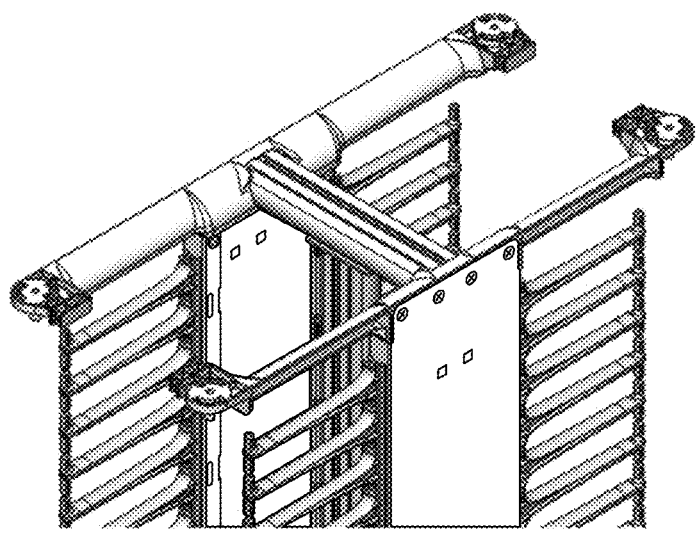
FIG. 4B
FIG. 4A

FEATURES FOR CABLE MANAGERS AND OTHER ELECTRONIC EQUIPMENT STRUCTURES

CROSS REFERENCE TO RELATED APPLICATIONS

The present application is a U.S. continuation patent application of, and claims priority under 35 U.S.C. § 120 to, U.S. nonprovisional patent application Ser. No. 16/203,050, filed Nov. 28, 2018, which '050 application published as U.S. Patent Application Publication No. US 2019/0098792 A1 on Mar. 28, 2019, which '050 application and the publication thereof are each incorporated herein by reference in their entirety, and which '050 application is a U.S. continuation patent application of, and claims priority under 35 U.S.C. § 120 to, U.S. nonprovisional patent application Ser. No. 15/843,879, filed Dec. 15, 2017, which '879 application published as U.S. Patent Application Publication No. US 2018/0110153 A1 on Apr. 19, 2018 and issued as U.S. Pat. No. 10,271,452 on Apr. 23, 2019, which '879 application, the publication thereof, and the patent issuing therefrom are each incorporated herein by reference in their entirety, and which '879 application is a U.S. continuation patent application of, and claims priority under 35 U.S.C. § 120 to, International Application No. PCT/US2017/043892, filed Jul. 26, 2017 and designating the U.S., which '892 application published as International Publication No. WO 2018/022721 A1 on Feb. 1, 2018, which '892 application and the application publication thereof are each incorporated herein by reference in their entirety, and which '892 application, for purposes of the United States, is a U.S. nonprovisional patent application of, and claims priority under 35 U.S.C. § 119(e) to, U.S. provisional patent application Ser. No. 62/366,900, filed Jul. 26, 2016 and entitled, "FEATURES FOR CABLE MANAGERS AND OTHER ELECTRONIC EQUIPMENT STRUCTURES," which '900 application is incorporated herein by reference in its entirety, and the '050 application is a U.S. continuation patent application of, and claims priority under 35 U.S.C. § 120 to, International Application No. PCT/US2017/043892, filed Jul. 26, 2017 and designating the U.S., which '892 application published as International Publication No. WO 2018/022721 A1 on Feb. 1, 2018, which '892 application and the application publication thereof are each incorporated herein by reference in their entirety, and which '892 application, for purposes of the United States, is a U.S. nonprovisional patent application of, and claims priority under 35 U.S.C. § 119(e) to, U.S. provisional patent application Ser. No. 62/366,900, filed Jul. 26, 2016 and entitled, "FEATURES FOR CABLE MANAGERS AND OTHER ELECTRONIC EQUIPMENT STRUCTURES," which '900 application is incorporated herein by reference in its entirety.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to cable managers and related electronic equipment structures, and, in particular, to flexible construction, cable accessories, and doors.

Background

Current and prior cable manager designs generally utilize a U-shaped chassis to which the peripheral parts of the frame are welded, riveted or otherwise attached. The chassis and other parts are usually constructed of sheet metal or injection-molded plastic with discrete patterns for attaching parts and accessories.

Current design methods use sheet metal, wire mesh or plastic parts to provide features for managing and/or supporting cabling and other cabling equipment or for attaching accessories that perform this function. Unfortunately, these features are generally provided in discrete patterns that limit the adjustability and flexibility often desired when managing cabling and other equipment within the manager. Using the features and accessories usually requires hardware and tools for installation, adjustment and/or removal. The chassis construction also makes it difficult to provide gentle cable entry and exit into the manager (i.e., for maintaining bend radii and proper support).

With regard to cable management accessories, current and prior cable manager designs generally utilize a sheet metal frame, sheet metal panel or bracket, or wire mesh with a grid pattern or other type of feature pattern. As a result, accessories are usually installed using hardware and tools and are only adjustable in incremental amounts along a pattern of features or holes within the frame or attachment surface, if at all. Some accessories do have toolless installation methods but are still limited in their application and installation location. Furthermore, much of the space in and around the manager is also wasted as accessories cannot be configured or installed to reach the entire space within the manager.

With regard to doors, particularly for cable managers, it is well known to provide doors that feature hinges at both left and right sides. However, conventional designs generally allow the door to swing on a single bearing surface. Unfortunately, doors that simply swing on a pivot point often sag. When such a door is closed, the bottom edges/surfaces of the door and/or hinge area often make contact with the door frame. As a result, such a door must be pushed, with some effort, back into its closed state. Some door designs address this issue with a ramp-style feature (usually made of plastic or sheet metal) to compensate for sag of the door, which may allow the door to be in an appropriate position for the latch mechanism to engage. However, known door designs maintain a certain level of interference and drag along the bottom of the door as it closes, regardless of whether they must be pushed into place by the user or ramped up into position. In such designs, the bottom of the door or hinge area drags or slides along the frame and creates a frictional force opposite the desired direction of motion.

For the foregoing reasons and/or other reasons, improvements in cable manager structures, accessories, and doors are needed.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

Broadly defined, the present invention according to one aspect is a cable manager frame design that increases flexibility, modularity and efficient use of the cable manager frame and space through the use of a track system.

Broadly defined, the present invention according to another aspect is a cable manager frame and accessory system design that allows easy installation, adjustment and removal of the accessories within a highly flexible and configurable space within and around the manager.

Broadly defined, the present invention according to another aspect is a door hinge set for cable managers, IT cabinets, and other enclosures that allows the door to open both left and right in the same manner and removes interference as the door closes to allow it to open and close smoothly and without drag or interference.

Broadly defined, the present invention according to another aspect is a cable manager. The cable manager includes a backbone assembly and at least one side wall extending from the backbone assembly. The at least one side wall optionally includes one or more cable finger units. The backbone assembly includes a spine member having an extruded construction. The spine member includes one or more channels extending substantially an entire length thereof to facilitate easy attachment, removal and/or repositioning of a structure relative to the spine member.

In a feature of this aspect, the backbone assembly may include a pair of lateral members, each having an extruded construction, to which the spine member is interconnected via a mounting bracket. In a further feature of this aspect, adjustment of a position of the spine member relative to the lateral members may be infinite along a length of the lateral members.

In another feature of this aspect, the structure may be an accessory rod that extends transversely away from the spine member. In further features of this aspect, the accessory rod may be part of an accessory rod assembly that includes a knob member threaded through a base member, wherein tightening of the knob member secures the accessory rod relative to the spine member; the accessory rod may be part of an accessory rod assembly that includes a cam mechanism for securing the accessory rod relative to the spine member; the accessory rod may have an extruded construction; the cable manager may further include at least one half-spool accessory, securable to the accessory rod or another structure via a snap mechanism, for routing and/or arranging cables relative to the cable manager; and/or the cable manager may further include at least one cable finger accessory, securable to the accessory rod or another structure via a cam and latch mechanism, for routing and/or arranging cables relative to the cable manager.

In another feature of this aspect, the cable manager may further include at least one strap/buckle accessory that includes a flexible strap for bundling cables, a buckle for accommodating the flexible strap and a buckle support that is securable within a channel of the spine member or another structure having an extruded construction. In a further feature of this aspect, the buckle may be rotatable.

In another feature of this aspect, the cable manager may further include a door assembly, wherein: the at least one side wall is a first side wall; a second side wall is disposed at an opposite end of the backbone assembly and extends from the backbone assembly in the same direction as the first side wall; the door assembly includes a door panel and a hinge set, at each side of the door panel, that hingedly secures the door panel to distal ends of the first and second side walls; and each hinge set includes a corresponding latch assembly that facilitates interference-free opening and closing of the door panel at either side. In a further feature of this aspect, the door assembly may be mounted between support arms disposed at upper and lower ends of each of the first and second side walls. In a further feature of this aspect, each latch assembly may include a latch, a gear mechanism, and a retractable bolt operationally connected to the gear mechanism, such that rotation of the latch retracts the bolt within a hinge body of the corresponding hinge set, thereby permitting the door panel to be opened. In a further features of this aspect, at the mounted side of the door assembly as the door panel is opened, a lifter disk disposed in the lower support arm may operate in conjunction with a torsion spring to interface with the hinge set at the mounted side of the door assembly, thereby facilitating interference-free opening and closing of the door panel. In a further feature of this aspect, as the door panel is opened, a hinge body of the hinge set at the mounted side of the door assembly is forced upward along a lifting ramp of the lifter disk until reaching a bearing surface, at which point the door panel is able to freely rotate. In a further feature of this aspect, as the door panel is closed, the hinge body may engage the lifter disk, causing the lifter disk to rotate with rotation of the door panel and against a bias in the corresponding torsion spring, thereby maintaining the door panel in a lifted state and facilitating interference-free closing of the door panel.

Broadly defined, the present invention according to another aspect is a cable manager substantially as shown and described.

Broadly defined, the present invention according to another aspect is an accessory rod, for installation within a cable manager, substantially as shown and described.

Broadly defined, the present invention according to another aspect is a half-spool accessory, for installation within a cable manager, substantially as shown and described.

Broadly defined, the present invention according to another aspect is a cable finger accessory, for installation within a cable manager, substantially as shown and described.

Broadly defined, the present invention according to another aspect is a strap/buckle accessory, for installation within a cable manager, substantially as shown and described.

Broadly defined, the present invention according to another aspect is a cable manager frame and accessory system substantially as shown and described.

Broadly defined, the present invention according to another aspect is a door hinge set substantially as shown and described.

Broadly defined, the present invention according to another aspect is a method of assembling and/or using a cable frame and accessory system substantially as shown and described.

Broadly defined, the present invention according to another aspect is a cable manager and accessory system. The cable manager and accessory system includes a backbone assembly, upper and lower support arms extending forwardly from the backbone assembly, and at least one side wall interconnected between the upper and lower support arms. The at least one side wall includes one or more cable finger units. The backbone assembly includes a spine member, having an extruded construction and a generally uniform cross-sectional shape. The spine member includes one or more channels extending along a length thereof to facilitate attachment, removal and/or repositioning of a structure relative to the spine member.

In a feature of this aspect, the spine member includes at least one curved surface to provide a bend radius for cables.

In another feature of this aspect, the backbone assembly further includes a lateral member, having an extruded construction and a generally uniform cross-sectional shape, to which the spine member is connected.

In another feature of this aspect, adjustment of a position of the spine member relative to the lateral member is infinite along a length of the lateral member.

In another feature of this aspect, each of the spine member and the lateral member utilize the same extruded construction such that the cross-sectional shape of the spine member is the same as the cross-sectional shape of the lateral member, and the lateral member includes one or more channels extending along a length thereof.

In another feature of this aspect, the one or more channels of each of the spine member and the lateral member include at least one T-slot channel capable of receiving a head of a fastener and at least one screw-in channel capable of receiving a screw-in fastener.

In another feature of this aspect, the lateral member is connected to an end of the spine member via a mounting bracket.

In another feature of this aspect, the mounting bracket includes a raised lip for alignment of the lateral member relative to the spine member.

In another feature of this aspect, a first fastener extends through a first aperture of the mounting bracket and is received longitudinally within the at least one screw-in channel of the spine member, and a second fastener extends through a second aperture of the mounting bracket and is received within the at least one T-slot channel of the lateral member.

In another feature of this aspect, the second fastener is braced within the T-slot channel of the lateral member with a spring nut seated within the T-slot channel.

In another feature of this aspect, the lateral member is a first lateral member arranged at a top of the spine member, the backbone assembly further includes a second lateral member arranged at a bottom of the spine member, the spine member is interconnected between the first and second lateral members, and adjustment of a position of the spine member relative to the first and second lateral members is infinite along lengths of the first and second lateral members.

In another feature of this aspect, the structure includes an accessory rod assembly having an accessory rod that extends transversely away from the spine member.

In another feature of this aspect, adjustment of a position of the accessory rod assembly relative to the spine member is infinite along a length of the spine member.

In another feature of this aspect, the accessory rod assembly includes a base member having at least one hook for placement against a ledge of one of the one or more channels of the spine member.

In another feature of this aspect, the accessory rod assembly further includes a rotatable knob having a threaded shaft that is received within a threaded portion of the base member, rotation of the rotatable knob in a selected direction positions a distal end of the threaded shaft against a wall of one of the one or more channels of the spine member, and positioning of the distal end of the threaded shaft against the wall, together with placement of the at least one hook against the ledge, clamps the accessory rod assembly to the spine member.

In another feature of this aspect, the accessory rod assembly further includes a rotatable cam lever mounted to the base member and having a toothed cam, rotation of the rotatable cam lever in a selected direction positions the toothed cam against a wall of one of the one or more channels of the spine member, and positioning of the toothed cam against the wall, together with placement of the at least one hook against the ledge, clamps the accessory rod assembly to the spine member.

In another feature of this aspect, the accessory rod has an extruded construction and a generally uniform cross-sectional shape, and the accessory rod includes one or more channels extending along a length thereof.

In another feature of this aspect, the cable manager and accessory system further includes at least one half-spool accessory mounted on the accessory rod for routing and/or arranging cables.

In another feature of this aspect, adjustment of a position of the at least one half-spool accessory relative to the accessory rod is infinite along a length of the accessory rod.

In another feature of this aspect, the at least one half-spool accessory includes a plurality of resilient snaps for retaining the at least one half-spool accessory on the accessory rod.

In another feature of this aspect, each resilient snap is engaged with a ledge of one of the one or more channels of the accessory rod.

In another feature of this aspect, the at least one half-spool accessory includes a curved central portion to provide a bend radius for cables.

In another feature of this aspect, the at least one half-spool accessory includes one or more end flanges for retaining cables against the curved central portion.

In another feature of this aspect, the at least one half-spool accessory includes one or more standoffs for positioning the at least one half-spool accessory against the accessory rod.

In another feature of this aspect, the at least one half-spool accessory is a first half-spool accessory mounted to an upper side of the accessory rod, the cable manager further includes a second half-spool accessory mounted to a lower side of the accessory rod, and the first and second half-spool accessories together define a generally cylindrical spool shape.

In another feature of this aspect, the one or more channels of the accessory rod include at least one T-slot channel for accommodating the head of a fastener to facilitate attachment of a separate structure to the accessory rod.

In another feature of this aspect, the one or more channels of the accessory rod include at least one screw-in channel.

In another feature of this aspect, the at least one screw-in channel is an extension of the at least one T-slot channel.

In another feature of this aspect, the one or more channels of the accessory rod include at least one grip channel.

In another feature of this aspect, the cable manager and accessory system further includes at least one cable finger accessory secured to the accessory rod for routing cables and/or accommodating other accessories.

In another feature of this aspect, the at least one cable finger accessory includes first and second clamp sections connected to one another via a first hinge and permitted to rotate relative to one another, a cable finger extending from at least one of the clamp sections, and a clamp mechanism that couples distal ends of the pair of clamp sections together around a section of the accessory rod, thereby clamping the at least one cable finger accessory to the accessory rod and arranging the at least one cable finger accessory in an installed configuration.

In another feature of this aspect, the clamp mechanism includes a cam lever link connected to the distal end of one of the first and second clamp sections via a second hinge, a cam lever connected to a distal end of the cam lever link via a third hinge, the cam lever having a cam structure at a proximal end thereof, and a cam trough extending from the distal end of the other of the first and second clamp sections.

In another feature of this aspect, in the installed configuration, the cam structure is received within the cam trough, and the cam lever is seated against the clamp section from which the cam trough extends.

In another feature of this aspect, the cam trough includes a notch for receiving the cam lever link when the at least one cable finger accessory is in the installed configuration.

In another feature of this aspect, in the installed configuration, a male snap structure extending from the cam lever is received within a female snap receptacle of the clamp section from which the cam trough extends.

In another feature of this aspect, one or both of the clamp sections include at least one locating rib that engages the accessory rod.

In another feature of this aspect, in the installed configuration, the at least one locating rib is seated in the at least one grip channel of the accessory rod to prevent free rotation of the at least one cable finger accessory.

In another feature of this aspect, the at least one cable finger accessory is rotatable to different positions on the accessory rod.

In another feature of this aspect, the cable finger includes one or more openings to accommodate a cable strap/buckle accessory.

In another feature of this aspect, a distal end of the cable finger includes an overhang to retain routed cables.

In another feature of this aspect, the cable manager and accessory system further includes a cable strap/buckle accessory, secured to one of the spine member or the lateral member, for bundling and/or retaining cables.

In another feature of this aspect, the cable strap/buckle accessory includes a buckle that is rotatably paired with a buckle support.

In another feature of this aspect, the buckle is rotatable relative to the buckle support in either a clockwise direction or a counterclockwise direction.

In another feature of this aspect, the cable strap/buckle accessory further includes a strap slidably engaged with the buckle.

In another feature of this aspect, ends of the strap are securable to one another with hook-and-loop fasteners.

In another feature of this aspect, the buckle includes a generally round socket, the buckle support may include a generally round snap, and the generally round snap is received within the socket by snap-fit to secure the buckle to the buckle support.

In another feature of this aspect, the snap is a split snap having at least a pair of snap sections that are deflectable toward one another to facilitate receipt of the split snap within the socket.

In another feature of this aspect, the buckle includes at least one arcuate boss that is generally coaxial with the generally round socket, the buckle support includes a trough that is generally coaxial with the generally round snap, when the buckle is secured to the buckle support, the at least one arcuate boss is received within the trough, and the at least one arcuate boss is slidable within the trough to facilitate rotation of the buckle relative to the buckle support.

In another feature of this aspect, the buckle support includes a mounting boss that is received within one of the one or more channels of the spine member or the lateral member.

In another feature of this aspect, the mounting boss is received within a T-slot channel and is rotated such that the mounting boss is blocked from passage through the T-slot channel, thereby securing the cable strap/buckle accessory to the backbone assembly.

In another feature of this aspect, the mounting boss includes a generally rectangular shape having two rounded corners disposed opposite from one another and two generally right-angle corners disposed opposite from one another, the rounded corners facilitate rotation of the mounting boss within the T-slot channel by approximately 90 degrees to a locked configuration, and the generally right-angle corners prevent rotation of the mounting boss within the T-slot channel beyond approximately 90 degrees to help retain the mounting boss in the locked configuration.

Broadly defined, the present invention according to another aspect is an accessory rod assembly for use in connection with a cable manager. The accessory rod assembly includes a base member and an accessory rod secured to and extending from the base member. The accessory rod has an extruded construction and a generally uniform cross-sectional shape along a length thereof. The base member is mountable to an extruded support member of the cable manager, and adjustment of a position of the base member relative to the extruded support member is infinite along a length of the extruded support member.

In a feature of this aspect, the base member includes at least one hook for placement against a ledge of a channel of the extruded support member, the base member further includes a rotatable knob having a threaded shaft that is received within a corresponding threaded portion, and the base member is securable to the extruded support member by rotation of the rotatable knob in a selected direction to position a distal end of the threaded shaft against a wall of the same or a different channel of the extruded support member, thereby clamping a portion of the extruded support member between the hook and the distal end of the threaded shaft.

In another feature of this aspect, the base member includes at least one hook for placement against a ledge of a channel of the extruded support member, the base member further includes a rotatable cam lever having a toothed cam, and the base member is securable to the extruded support member by rotation of the rotatable cam lever in a selected direction so as to position the toothed cam against a wall of the same or a different channel of the extruded support member, thereby clamping a portion of the extruded support member between the hook and the toothed cam.

In another feature of this aspect, the accessory rod includes one or more channels extending along a length thereof.

In another feature of this aspect, the one or more channels of the accessory rod include at least one T-slot channel for accommodating the head of a fastener to facilitate attachment of a separate structure to the accessory rod.

In another feature of this aspect, the one or more channels of the accessory rod include at least one screw-in channel.

In another feature of this aspect, the at least one screw-in channel is an extension of the at least one T-slot channel.

In another feature of this aspect, the one or more channels include at least one grip channel.

In another feature of this aspect, the accessory rod assembly further includes an end cap disposed at a distal end of the accessory rod.

Broadly defined, the present invention according to another aspect is a half-spool accessory for use in for routing and/or arranging cables in a cable manager. The half-spool accessory includes a curved support portion to provide a bend radius for cables, front and rear end flanges disposed at opposite ends of the curved support portion, and a plurality of resilient snaps extending downwardly from the curved support portion for retaining the half-spool accessory in a mounted configuration relative to an extruded support member of the cable manager.

In a feature of this aspect, each resilient snap is engaged with a ledge of a channel of the extruded support member that extends along a length thereof.

In another feature of this aspect, a position of the half-spool accessory relative to the extruded support member is infinitely adjustable along the length of the extruded support member.

In another feature of this aspect, the half-spool accessory further includes one or more standoffs extending downwardly from the curved support portion for positioning the half-spool accessory against the extruded support member.

In another feature of this aspect, the one or more standoffs each include a curved edge that interfaces with a corresponding curved surface of the extruded support member.

In another feature of this aspect, the curved support portion includes one or more notches along side edges thereof to provide finger grips for gripping the half-spool accessory.

Broadly defined, the present invention according to another aspect is a cable finger accessory for use in routing cables and/or accommodating other accessories in a cable manager. The cable finger accessory includes first and second clamp sections connected to one another via a first hinge and permitted to rotate relative to one another, a cable finger extending from at least one of the clamp sections, a cam lever link connected to the distal end of one of the first and second clamp sections via a second hinge, a cam lever connected to a distal end of the cam lever link via a third hinge, the cam lever having a cam structure at a proximal end thereof, and a cam trough extending from the distal end of the other of the first and second clamp sections. In an installed configuration, the pair of clamp sections is arranged around a section of an extruded support member of the cable manager, the cam structure is received within the cam trough, and the cam lever is seated against the clamp section from which the cam trough extends, thereby clamping the cable finger accessory to the extruded support member.

In a feature of this aspect, the cam trough includes a notch for receiving the cam lever link when the cable finger accessory is in the installed configuration.

In another feature of this aspect, in the installed configuration, a male snap structure extending from the cam lever is received within a female snap receptacle of the clamp section from which the cam trough extends.

In another feature of this aspect, one or both of the clamp sections include at least one locating rib that engages the extruded support member.

In another feature of this aspect, in the installed configuration, the at least one locating rib is seated in a channel of the extruded support member to prevent free rotation of the at least one cable finger accessory.

In another feature of this aspect, the cable finger includes one or more openings to accommodate a cable strap/buckle accessory.

In another feature of this aspect, a distal end of the cable finger includes an overhang to retain routed cables.

Broadly defined, the present invention according to another aspect is a cable strap/buckle accessory for bundling and/or retaining cables in a cable manager. The cable strap/buckle accessory includes a buckle having a generally round socket, a buckle support having a generally round snap, and a strap slidably engaged with the buckle for bundling a plurality of cables. The generally round snap is received within the socket by snap-fit to secure the buckle to the buckle support.

In a feature of this aspect, the buckle is rotatably paired with the buckle support.

In another feature of this aspect, the buckle is rotatable relative to the buckle support in either a clockwise direction or a counterclockwise direction.

In another feature of this aspect, ends of the strap are securable to one another with hook-and-loop fasteners.

In another feature of this aspect, the snap is a split snap having at least a pair of snap sections that are deflectable toward one another to facilitate receipt of the split snap within the socket.

In another feature of this aspect, the buckle includes at least one arcuate boss that is generally coaxial with the generally round socket, the buckle support includes a trough that is generally coaxial with the generally round snap, when the buckle is secured to the buckle support, the at least one arcuate boss is received within the trough, and the at least one arcuate boss is slidable within the trough to facilitate rotation of the buckle relative to the buckle support.

In another feature of this aspect, the buckle support includes a mounting boss that is receivable within a T-slot channel of an extruded support member of the cable manager.

In another feature of this aspect, the mounting boss is rotatable within the T-slot channel to facilitate the mounting boss being blocked from passage through the T-slot channel, thereby securing the cable strap/buckle accessory to the extruded support member.

In another feature of this aspect, the mounting boss includes a generally rectangular shape having two rounded corners disposed opposite from one another and two generally right-angle corners disposed opposite from one another, the rounded corners facilitate rotation of the mounting boss within the T-slot channel by approximately 90 degrees to a locked configuration, and the generally right-angle corners prevent rotation of the mounting boss within the T-slot channel beyond approximately 90 degrees to help retain the mounting boss in the locked configuration.

Broadly defined, the present invention according to another aspect is an extruded support member for implementation in a cable manager. The extruded support member includes an elongate body having a hollow interior and defining a plurality of channels extending along its length. The plurality of channels include a pair of screw-in channels that extend into the hollow interior of the elongate body at opposite sides thereof and a pair of T-slot channels extending away from opposed side walls of the elongate body. Each screw-in channel is sized and shaped to accommodate a threaded fastener received longitudinally at an end of the elongate body. Each T-slot channel is sized and shaped to receive and retain a boss of a separate fastener.

In a feature of this aspect, opposed sides of the elongate body are curved to provide a bend radius for cables.

In another feature of this aspect, the elongate body has a generally uniform cross-sectional shape along its length.

In another feature of this aspect, one or more ledges extend from side walls of the elongate body for aligning with and/or accommodating additional fasteners.

Broadly defined, the present invention according to another aspect is an extruded support member for implementation in a cable manager. The extruded support member includes an at least partially cylindrical elongate body that defines a pair of T-slot channels arranged at opposite sides thereof that extend along a length of the at least partially cylindrical elongate body and a pair of screw-in channels that extend along the length of the at least partially cylindrical elongate body. Each T-slot channel is sized and shaped to receive and retain a boss of a separate fastener. Each of the pair of screw-in channels is an extension of a respective one of the pair of T-slot channels, and each of the pair of screw-in channels is sized and shaped to accommodate a threaded fastener received longitudinally at an end of the at least partially cylindrical elongate body.

In a feature of this aspect, outward-facing sides of the at least partially cylindrical elongate body each include a plurality of grip channels for accommodating a separate structure snap-fit thereto.

In another feature of this aspect, the at least partially cylindrical elongate body has a generally uniform cross-sectional shape along its length.

Broadly defined, the present invention according to another aspect includes an IT enclosure with an easy-close door having a left side and a right side, including: a back assembly; a left side wall extending forward from the back assembly; a right side wall extending forward from the back assembly; a top left door support and a bottom left door support at a top front and a bottom front, respectively, of the left side wall; a top right door support and a bottom right door support at a top front and a bottom front, respectively, of the right side wall; a bottom cross member extending between the bottom left and right door supports; and a door assembly, including a door panel having a bottom edge, that is hingedly mounted between the top and bottom support members on the left side so as to rotate relative thereto, and that is hingedly mounted between the top and bottom support members on the right side so as to rotate relative thereto, wherein (1) the door assembly is mounted to the top support member on each respective side using a first hinge assembly and a first hinge mount, (2) the door assembly is mounted to the bottom support member on each respective side using a second hinge assembly and a second hinge mount, and (3) the first hinge mounts, the second hinge mounts, or both each include a lift-and-hold mechanism, and each corresponding hinge assembly includes a corresponding bearing structure; wherein (1) in a first state, which is a closed state, the door panel is closed along both the left and right sides thereof, the bottom edge of the door panel is in close proximity to the bottom cross member all the way across between the left and right sides, and the bottom edge of the door panel is at a first elevation, (2) in a second state, which is a first partially open state, the door panel has been opened along the left side or the right side and has been rotated to a point that engagement of the bearing structure with the lift-and-hold mechanism causes the door panel to be raised gradually as the door panel is rotated further open, thereby elevating the bottom edge of the door panel above the bottom cross member, (3) in a third state, which is a second partially open state, the door panel has been further opened, relative to the first partially open state, such that during further rotation the bottom edge of the door panel is held at a fixed elevated position above the bottom cross member, and (4) in a fourth state, which is a door closing state, the lift-and-hold mechanism interacts with the bearing structure to maintain the elevation of the bottom edge of the door panel above the bottom cross member during rotation of the door panel from the second partially open state back to the closed state, thereby avoiding interference between the bottom edge of the door panel and the bottom cross member.

In a feature of this aspect, the lift-and-hold mechanism includes a lifter disk that rotates about the axis of rotation of the door panel. In further features, the lifter disk is carried in a door support; the lifter disk is disposed in a lifter nest in an end of the door support; the lifter disk is carried in the door assembly; the lifter disk includes a lifting ramp that engages with the bearing structure to gradually raise the door panel as the door panel is being opened; the lifting ramp is a first lifting ramp, wherein the bearing structure includes a second lifting ramp, and wherein the first lifting ramp engages with the second lifting ramp to gradually raise the door panel as the door panel is being opened; the lifter disk further includes a first bearing surface and a second bearing surface, wherein the first and second bearing surfaces are at different elevations, wherein engagement of the bearing structure with the first bearing surface holds the bottom edge of the door panel at a lower elevation, and wherein engagement of the bearing structure with the second bearing surface maintains the elevation of the bottom edge of the door panel above the bottom cross member; and/or the lifter disk further includes a first engagement tooth, wherein the bearing structure further includes a second engagement tooth, and wherein engagement between the first and second engagement teeth causes the lifting disk to rotate with rotation of the door panel while the door panel is being closed, thereby maintaining the elevation of the bottom edge of the door panel above the bottom cross member.

In another feature of this aspect, the IT enclosure is implemented as a cable manager. In further features, the side walls include side wall finger units to provide routing options for cables; the door supports are integrated into the side wall finger units; and/or the door supports are integrated into support arms.

In another feature of this aspect, the IT enclosure is implemented as a cabinet.

In another feature of this aspect, each combination of a hinge assembly and a hinge mount implements a latch assembly. In a further feature, each latch assembly includes a spring-loaded structure that is temporarily pushed aside by closure of the door panel and returns to a previous position to the hold the door panel closed.

Broadly defined, the present invention according to another aspect includes a method of installing or arranging one or more cable management accessories in a cable manager. The method includes providing a cable manager having a backbone assembly constructed from a spine member and at least one lateral member, each of which has a generally uniform cross-sectional shape. Each of the spine member and the at least one lateral member includes one or more channels that extend along respective lengths thereof. A position of the spine member relative to the at least one lateral member is infinitely adjustable along the length of the lateral member. The method further includes securing an accessory rod assembly to the spine member so that an accessory rod of the accessory rod assembly extends transversely away from the spine member. A position of the accessory rod assembly relative to the spine member is infinitely adjustable along a length of the spine member.

In a feature of this aspect, the cross-sectional shape of the spine member is the same as the cross-sectional shape of the at least one lateral member.

In another feature of this aspect, the accessory rod assembly includes a base member, having at least one hook, and a rotatable knob having a threaded shaft that is received within a threaded portion of the base member.

In another feature of this aspect, securing the accessory rod assembly to the spine member includes: positioning the at least one hook against a ledge of one of the one or more channels of the spine member; and rotating the rotatable knob to position a distal end of the threaded shaft against a wall of the same or a different one of the one or more channels of the spine member, thereby clamping the accessory rod assembly to the spine member.

In another feature of this aspect, the accessory rod assembly includes a base member, having at least one hook, and a rotatable cam lever mounted to the base member, the rotatable cam lever including a toothed cam.

In another feature of this aspect, securing the accessory rod assembly to the spine member includes: positioning the at least one hook against a ledge of one of the one or more channels of the spine member; and rotating the rotatable cam lever to position the toothed cam against a wall of the same or a different one of the one or more channels of the spine member, thereby clamping the accessory rod assembly to the spine member.

In another feature of this aspect, the accessory rod has a generally uniform cross-sectional shape and one or more channels that extend along a length thereof.

In another feature of this aspect, the method further includes mounting a half-spool accessory to the accessory rod.

In another feature of this aspect, mounting the half-spool accessory to the accessory rod includes: positioning a first resilient snap of the half-spool accessory to be seated beneath a ledge of a first one of the one or more channels of the accessory rod; rotating the half-spool accessory toward the accessory rod; engaging a second resilient snap of the half-spool accessory against a ledge of a second one of the one or channels of the accessory rod; and applying a force to the half-spool accessory such that the second resilient snap is sufficiently deflected to permit the second resilient snap to be seated beneath the ledge of the second one of the one or more channels of the accessory rod.

In another feature of this aspect, a position of the half-spool accessory relative to the accessory rod is infinitely adjustable along the length of the accessory rod.

In another feature of this aspect, the method further includes removing the half-spool accessory from the accessory rod.

In another feature of this aspect, removing the half-spool accessory from the accessory rod includes pulling the half-spool accessory off from a distal end of the accessory rod.

In another feature of this aspect, removing the half-spool accessory from the accessory rod includes applying a force to the half-spool accessory to sufficiently deflect at least one of the first and second resilient snaps so that such resilient snap is no longer seated beneath the corresponding ledge of the accessory rod.

In another feature of this aspect, the method further includes securing a cable finger accessory to the accessory rod.

In another feature of this aspect, the cable finger accessory includes first and second clamp sections connected to one another via a first hinge and permitted to rotate relative to one another, a cable finger extending from at least one of the first and second clamp sections, a cam lever link connected to the distal end of the first clamp section via a second hinge, a cam lever connected to a distal end of the cam lever link via a third hinge, the cam lever having a cam structure at a proximal end thereof, and a cam trough extending from the distal end of the second clamp section.

In another feature of this aspect, securing the cable finger accessory to the accessory rod includes: positioning the first clamp section against the accessory rod; rotating the second clamp section toward the accessory rod so that the accessory rod is disposed between the first and second clamp sections; rotating the cam lever link toward the second clamp section; positioning the cam structure of the cam lever to be seated in the cam trough; and rotating the cam lever toward the second clamp section to clamp the first and second clamp sections together around the accessory rod with the cable finger extending in a first direction.

In another feature of this aspect, the one or more channels of the accessory rod includes a grip channel, and positioning the first clamp section against the accessory rod includes positioning a rib of the first clamp section within the grip channel of the accessory rod.

In another feature of this aspect, the method further includes fitting a portion of the cam lever link within a notch in the cam trough.

In another feature of this aspect, the method further includes fitting a male snap structure on the cam lever within a female snap receptacle on the second clamp section.

In another feature of this aspect, the method further includes repositioning the cable finger accessory so that the cable finger extends in a second direction.

In another feature of this aspect, repositioning the cable finger accessory includes: rotating the cam lever away from the second clamp section to loosen the grip of the first and second clamp sections against the accessory rod; rotating the cable finger accessory relative to the accessory rod so that the cable finger extends in the second direction; and rotating the cam lever toward the second clamp section to clamp the first and second clamp sections together around the accessory rod with the cable finger extending in the second direction.

In another feature of this aspect, the method further includes securing a cable strap/buckle accessory to a cable finger of the cable finger accessory.

In another feature of this aspect, securing the cable strap/buckle accessory includes: positioning a mounting boss, extending from a buckle support of the cable strap/buckle accessory, through a generally rectangular opening of the cable finger; and rotating the mounting boss so that sides of the mounting boss extend transversely across the generally rectangular opening, thereby blocking the mounting boss from passing back out from the opening.

In another feature of this aspect, the method further includes securing a cable strap/buckle accessory to one of the spine member or the at least one lateral member.

In another feature of this aspect, securing the cable strap/buckle accessory includes: positioning a mounting boss, extending from a buckle support of the cable strap/buckle accessory, into a T-shaped one of the one or more channels of either the spine member or the at least one lateral member; and rotating the mounting boss so that sides of the mounting boss extend transversely into the T-shaped channel, thereby blocking the mounting boss from passing back out from the T-shaped channel.

In another feature of this aspect, the method further includes fitting a generally round snap on the buckle support through a generally round socket of a buckle of the cable strap/buckle accessory.

In another feature of this aspect, the buckle is capable of free rotation relative to the buckle support.

In another feature of this aspect, securing the cable strap/buckle accessory includes positioning an arcuate boss on the buckle within a corresponding trough on the buckle support.

In another feature of this aspect, the arcuate boss on the buckle is generally coaxial with the generally round socket, and the trough on the buckle support is generally coaxial with the generally round snap.

In another feature of this aspect, the arcuate boss is slidable within the trough.

In another feature of this aspect, the snap is a split snap having at least a pair of snap sections that are deflectable toward one another to facilitate receipt of the split snap within the socket.

In another feature of this aspect, the method further includes fitting a strap through one or more slots in the buckle.

Broadly defined, the present invention according to another aspect includes a method of installing a cable management accessory on an extruded support member having a generally uniform cross-sectional shape. The method includes: providing an extruded support member having at least one T-slot channel that extends along a length thereof; and securing an accessory rod assembly to the extruded support member, by clamping a base member of the accessory rod assembly to the at least one T-slot channel, so that an accessory rod of the accessory rod assembly extends transversely away from the extruded support member. A position of the accessory rod assembly relative to the extruded support member is infinitely adjustable along the length of the extruded support member.

In a feature of this aspect, the base member has at least one hook and a rotatable knob having a threaded shaft that is received within a threaded portion of the base member.

In another feature of this aspect, securing the accessory rod assembly to the extruded support member includes: positioning the at least one hook against a ledge of the at least one T-slot channel of the extruded support member; and rotating the rotatable knob to position a distal end of the threaded shaft against a wall of the at least one T-slot channel of the extruded support member, thereby clamping the accessory rod assembly to the extruded support member.

In another feature of this aspect, the base member has at least one hook and a rotatable cam lever mounted to the base member, the rotatable cam lever including a toothed cam.

In another feature of this aspect, securing the accessory rod assembly to the extruded support member includes: positioning the at least one hook against a ledge of the at least one T-slot channel of the extruded support member; and rotating the rotatable cam lever to position the toothed cam against a wall of the at least one T-slot channel of the extruded support member, thereby clamping the accessory rod assembly to the extruded support member.

In another feature of this aspect, the accessory rod has a generally uniform cross-sectional shape and one or more channels that extend along a length thereof.

In another feature of this aspect, the method further includes mounting a half-spool accessory to the accessory rod.

In another feature of this aspect, mounting the half-spool accessory to the accessory rod includes: positioning a first resilient snap of the half-spool accessory to be seated beneath a ledge of a first one of the one or more channels of the accessory rod; rotating the half-spool accessory toward the accessory rod; engaging a second resilient snap of the half-spool accessory against a ledge of a second one of the one or channels of the accessory rod; and applying a force to the half-spool accessory such that the second resilient snap is sufficiently deflected to permit the second resilient snap to be seated beneath the ledge of the second one of the one or more channels of the accessory rod.

In another feature of this aspect, a position of the half-spool accessory relative to the accessory rod is infinitely adjustable along the length of the accessory rod.

In another feature of this aspect, the method further includes removing the half-spool accessory from the accessory rod.

In another feature of this aspect, removing the half-spool accessory from the accessory rod includes pulling the half-spool accessory off from a distal end of the accessory rod.

In another feature of this aspect, removing the half-spool accessory from the accessory rod includes applying a force to the half-spool accessory to sufficiently deflect at least one of the first and second resilient snaps so that such resilient snap is no longer seated beneath the corresponding ledge of the accessory rod.

In another feature of this aspect, the method further includes securing a cable finger accessory to the accessory rod.

In another feature of this aspect, the cable finger accessory includes: first and second clamp sections connected to one another via a first hinge and permitted to rotate relative to one another; a cable finger extending from at least one of the first and second clamp sections; a cam lever link connected to the distal end of the first clamp section via a second hinge; a cam lever connected to a distal end of the cam lever link via a third hinge, the cam lever having a cam structure at a proximal end thereof; and a cam trough extending from the distal end of the second clamp section.

In another feature of this aspect, securing the cable finger accessory to the accessory rod includes: positioning the first clamp section against the accessory rod; rotating the second clamp section toward the accessory rod so that the accessory rod is disposed between the first and second clamp sections; rotating the cam lever link toward the second clamp section; positioning the cam structure of the cam lever to be seated in the cam trough; and rotating the cam lever toward the second clamp section to clamp the first and second clamp sections together around the accessory rod with the cable finger extending in a first direction.

In another feature of this aspect, the one or more channels of the accessory rod includes a grip channel, and positioning the first clamp section against the accessory rod includes positioning a rib of the first clamp section within the grip channel of the accessory rod.

In another feature of this aspect, the method further includes fitting a portion of the cam lever link within a notch in the cam trough.

In another feature of this aspect, the method further includes fitting a male snap structure on the cam lever within a female snap receptacle on the second clamp section.

In another feature of this aspect, the method further includes repositioning the cable finger accessory so that the cable finger extends in a second direction.

In another feature of this aspect, repositioning the cable finger accessory includes: rotating the cam lever away from the second clamp section to loosen the grip of the first and second clamp sections against the accessory rod; rotating the cable finger accessory relative to the accessory rod so that the cable finger extends in the second direction; and rotating the cam lever toward the second clamp section to clamp the first and second clamp sections together around the accessory rod with the cable finger extending in the second direction.

In another feature of this aspect, the method further includes securing a cable strap/buckle accessory to a cable finger of the cable finger accessory.

In another feature of this aspect, securing the cable strap/buckle accessory includes: positioning a mounting boss, extending from a buckle support of the cable strap/buckle accessory, through a generally rectangular opening of the cable finger; and rotating the mounting boss so that sides of the mounting boss extend transversely across the generally rectangular opening, thereby blocking the mounting boss from passing back out from the opening.

Broadly defined, the present invention according to another aspect includes a method of installing a cable strap/buckle accessory on an extruded support member having a generally uniform cross-sectional shape. The method includes: providing an extruded support member that defines at least one T-slot channel that extends along a length thereof; positioning a mounting boss, extending from a buckle support of the cable strap/buckle accessory, into the at least one T-shaped channel; and rotating the mounting boss so that sides of the mounting boss extend transversely into the T-shaped channel, thereby blocking the mounting boss from passing back out from the at least one T-shaped channel.

In another feature of this aspect, the method further includes fitting a generally round snap on the buckle support through a generally round socket of a buckle of the cable strap/buckle accessory.

In another feature of this aspect, the buckle is capable of free rotation relative to the buckle support.

In another feature of this aspect, securing the cable strap/buckle accessory includes positioning an arcuate boss on the buckle within a corresponding trough on the buckle support.

In another feature of this aspect, wherein the arcuate boss on the buckle is generally coaxial with the generally round socket, and the trough on the buckle support is generally coaxial with the generally round snap.

In another feature of this aspect, the arcuate boss is slidable within the trough.

In another feature of this aspect, the snap is a split snap having at least a pair of snap sections that are deflectable toward one another to facilitate receipt of the split snap within the socket.

In another feature of this aspect, the method further includes fitting a strap through one or more slots in the buckle.

Broadly defined, the present invention according to another aspect includes a cable manager with an easy-close door having a left side and a right side, including: a back assembly; a left side wall extending forward from the back assembly; a right side wall extending forward from the back assembly; a top left door support and a bottom left door support at a top front and a bottom front, respectively, of the left side wall; a top right door support and a bottom right door support at a top front and a bottom front, respectively, of the right side wall; a bottom cross member extending between the bottom left and right door supports; a door assembly, including a door panel having a bottom edge, that is mounted between the top and bottom support members on the left side via one or more hinge-latch mechanisms and that is likewise mounted between the top and bottom support members on the right side via one or more hinge-latch mechanisms such that the one or more hinge-latch mechanisms on the right side may be released to permit the door panel to be rotated relative to the one or more hinge-latch mechanism on the left side and such that the one or more hinge-latch mechanisms on the left side may be alternatively released to permit the door panel to be rotated relative to the one or more hinge-latch mechanism on the right side; a lift-and-hold mechanism and a bearing structure, one of which is supported by and carried on the rotatable door panel and the other of which is supported by a static portion of the cable manager, wherein the lift-and-hold mechanism and bearing structure are jointly adapted to support the door panel during some or all of a process of hingedly opening and closing the door panel from the left side, the right side, or both, wherein the lift-and-hold mechanism is movable relative to the structure on which it is carried, and wherein the lift-and-hold mechanism includes a plurality of surface features for interaction with the bearing structure as the door panel is rotated opened and closed about an axis of rotation, the structures including a first bearing surface that supports the door panel at a first elevation in an initial closed state, a lifting surface that makes contact with the door panel while the door panel is being hinged opened and, through such contact, lifts the door panel to a second elevation as the door panel is opened further, the second elevation being higher than the first elevation, and a second bearing surface that subsequently supports the door panel at the second elevation once the door panel is opened still further, and continues supporting the door panel at the second elevation while the door is subsequently being rotated from the still further opened state back to the closed state, thereby avoiding interference between the bottom edge of the door panel and the bottom cross member while the door panel is being closed.

In a feature of this aspect, as the door is being rotated from the still further opened state back to the closed state, at least a portion of the lift-and-hold mechanism moves, relative to the structure on which the lift-and-hold mechanism is carried, while continuing to support the door panel on the second bearing surface. In further features, the lift-and-hold mechanism further includes an engagement structure that engages the door panel after the door panel is lifted to the second elevation by the lifting surface, wherein such engagement causes the movable portion of the lift-and-hold mechanism to move when the door panel is moved; the door panel includes a corresponding engagement structure that is engaged by the engagement structure of the lift-and-hold mechanism; the engagement structure of the lift-and-hold mechanism is an engagement tooth; the engagement tooth is a first engagement tooth, wherein the bearing structure includes a second engagement tooth, and wherein engagement between the first and second engagement teeth causes the movable portion of the lift-and-hold mechanism to move with the door panel when the door panel is moved, thereby holding the door panel on the second bearing surface and maintaining the elevation of the bottom edge of the door panel above the bottom cross member; the lifting surface includes a ramp that engages with the bearing structure to gradually raise the door panel as the door panel is being opened; the ramp initially, as the door panel is being opened, lifts the door panel to a third elevation that is higher than the second elevation, and wherein as the door panel is further opened, the door panel is dropped from the third elevation down to the second elevation; the ramp is a first ramp, wherein the bearing structure includes a second ramp, and wherein the first ramp engages with the second ramp to gradually raise the door panel as the door panel is being opened; the movable portion of the lift-and-hold mechanism rotates about the axis of rotation of the door panel; the movable portion of the lift-and-hold mechanism includes a lifter disk; the lifter disk is disposed in a lifter nest; the lift-and-hold mechanism is supported and carried by a first of the door supports, and wherein the lift-and-hold mechanism is movable relative to the first door support; the lift-and-hold mechanism includes a lifter disk that is disposed in a lifter nest in an end of the first door support; the lift-and-hold mechanism is supported and carried by the door panel, and wherein the lift-and-hold mechanism is movable relative to the door panel; the hinge-latch mechanism includes a hinge mount having a hinge pin, and wherein movable portion of the lift-and-hold mechanism rotates around the hinge pin; the lift-and-hold mechanism includes a spring that biases the movable portion of the lift-and-hold mechanism; when the bearing structure is disengaged, by a user, from the second bearing surface, the spring returns to the movable portion of the lift-and-hold mechanism to an initial state; the movable portion of the lift-and-hold mechanism slides transversely along a front of the cable manager; the movable portion of the lift-and-hold mechanism includes a sliding lifter arm; and/or the bearing structure is incorporated into the hinge-latch mechanism.

In another feature of this aspect, the side walls include side wall finger units to provide routing options for cables. In a further feature, the door supports are integrated into the side wall finger units.

In another feature of this aspect, the door supports are integrated into support arms.

In another feature of this aspect, the hinge-latch mechanism includes a hinge assembly and a hinge mount. In further features, each combination of a hinge assembly and a hinge mount implements a latch assembly; each latch assembly includes a spring-loaded structure that is temporarily pushed aside by closure of the door panel and returns to a previous position to the hold the door panel closed; the bearing structure is incorporated into the hinge assembly; and/or the lift-and-hold mechanism is incorporated into the hinge mount.

Broadly defined, the present invention according to another aspect includes an IT enclosure with an easy-close door having a left side and a right side, including: a back assembly; a left side wall extending forward from the back assembly; a right side wall extending forward from the back assembly; a top left door support and a bottom left door support at a top front and a bottom front, respectively, of the left side wall; a top right door support and a bottom right door support at a top front and a bottom front, respectively, of the right side wall; a bottom cross member extending between the bottom left and right door supports; a door assembly, including a door panel having a bottom edge, that is mounted between the top and bottom support members on the left side via one or more hinge-latch mechanisms and that is likewise mounted between the top and bottom support members on the right side via one or more hinge-latch mechanisms such that the one or more hinge-latch mechanisms on the right side may be released to permit the door panel to be rotated relative to the one or more hinge-latch mechanism on the left side and such that the one or more hinge-latch mechanisms on the left side may be alternatively released to permit the door panel to be rotated relative to the one or more hinge-latch mechanism on the right side; a lift-and-hold mechanism and a bearing structure, one of which is supported by and carried on the rotatable door panel and the other of which is supported by a static portion of the IT enclosure, wherein the lift-and-hold mechanism and bearing structure are jointly adapted to support the door panel during some or all of a process of hingedly opening and closing the door panel from the left side, the right side, or both, wherein the lift-and-hold mechanism is movable relative to the structure on which it is carried, and wherein the lift-and-hold mechanism includes a plurality of surface features for interaction with the bearing structure as the door panel is rotated opened and closed about an axis of rotation, the structures including a first bearing surface that supports the door panel at a first elevation in an initial closed state, a lifting surface that makes contact with the door panel while the door panel is being hinged opened and, through such contact, lifts the door panel to a second elevation as the door panel is opened further, the second elevation being higher than the first elevation, and a second bearing surface that subsequently supports the door panel at the second elevation once the door panel is opened still further, and continues supporting the door panel at the second elevation while the door is subsequently being rotated from the still further opened state back to the closed state, thereby avoiding interference between the bottom edge of the door panel and the bottom cross member while the door panel is being closed Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIG. 4A is an isometric view of a double-sided cable manager in accordance with a preferred embodiment of the present invention;

FIG. 4B is an isometric close-up partial view of the double-sided cable manager of FIG. 4A;

DETAILED DESCRIPTION

Figure 1:
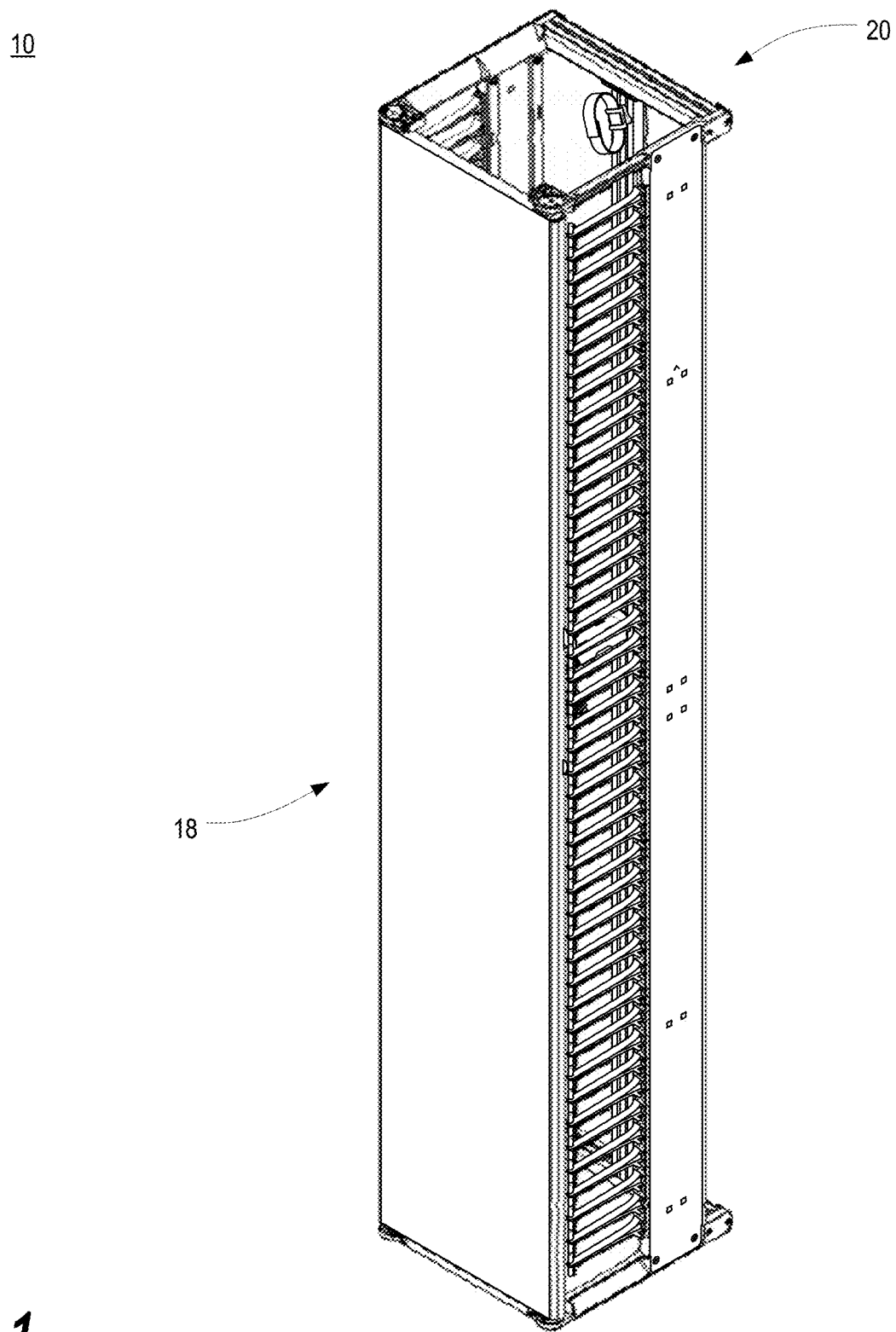
FIG. 1 is a front isometric view of a cable manager in accordance with a preferred embodiment of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

Figure 2:
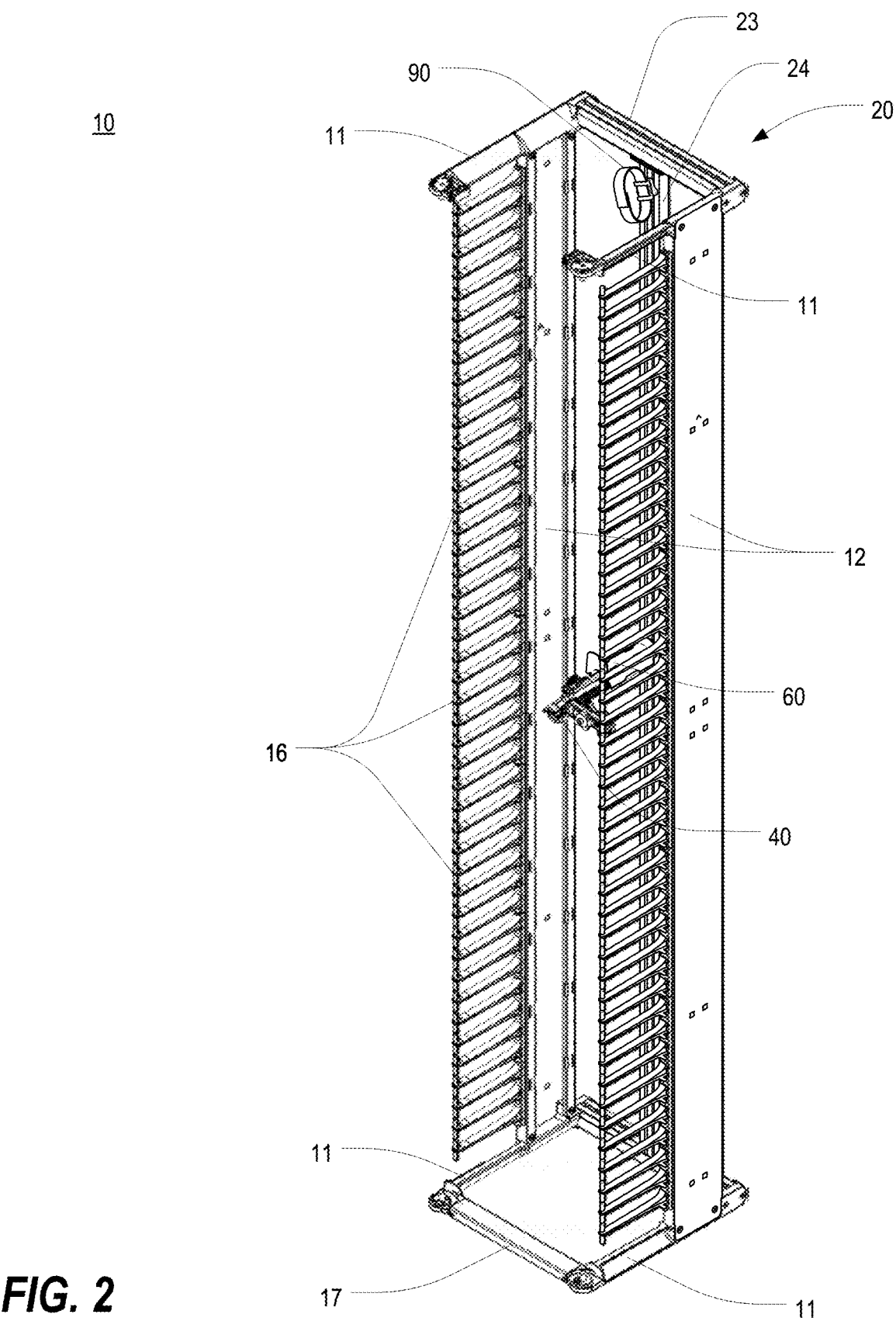
FIG. 2 is a front isometric view of the cable manager of FIG. 1, shown with a cover removed to reveal a backbone assembly and an accessory rod assembly.

FIG. 1 is a front isometric view of a cable manager 10 in accordance with a preferred embodiment of the present invention, and FIG. 2 is a front isometric view of the cable manager 10 of FIG. 1, shown with a cover removed to reveal a backbone assembly 20 and an accessory rod assembly 40. As shown, elements of the cable manager 10 include, or may include, a backbone assembly 20, side walls 12, side wall cable finger units 16, support arms 11, at least one cross bar 17, and a door assembly 18. In some embodiments, the cable manager 10 also includes, or may include, various cable management accessories, which may include one or more accessory rod assemblies 40, one or more half spools 60, one or more repositionable cable finger accessories 70, and/or one or more cable strap/buckle accessories 90, as well as other accessories.

Figure 3:
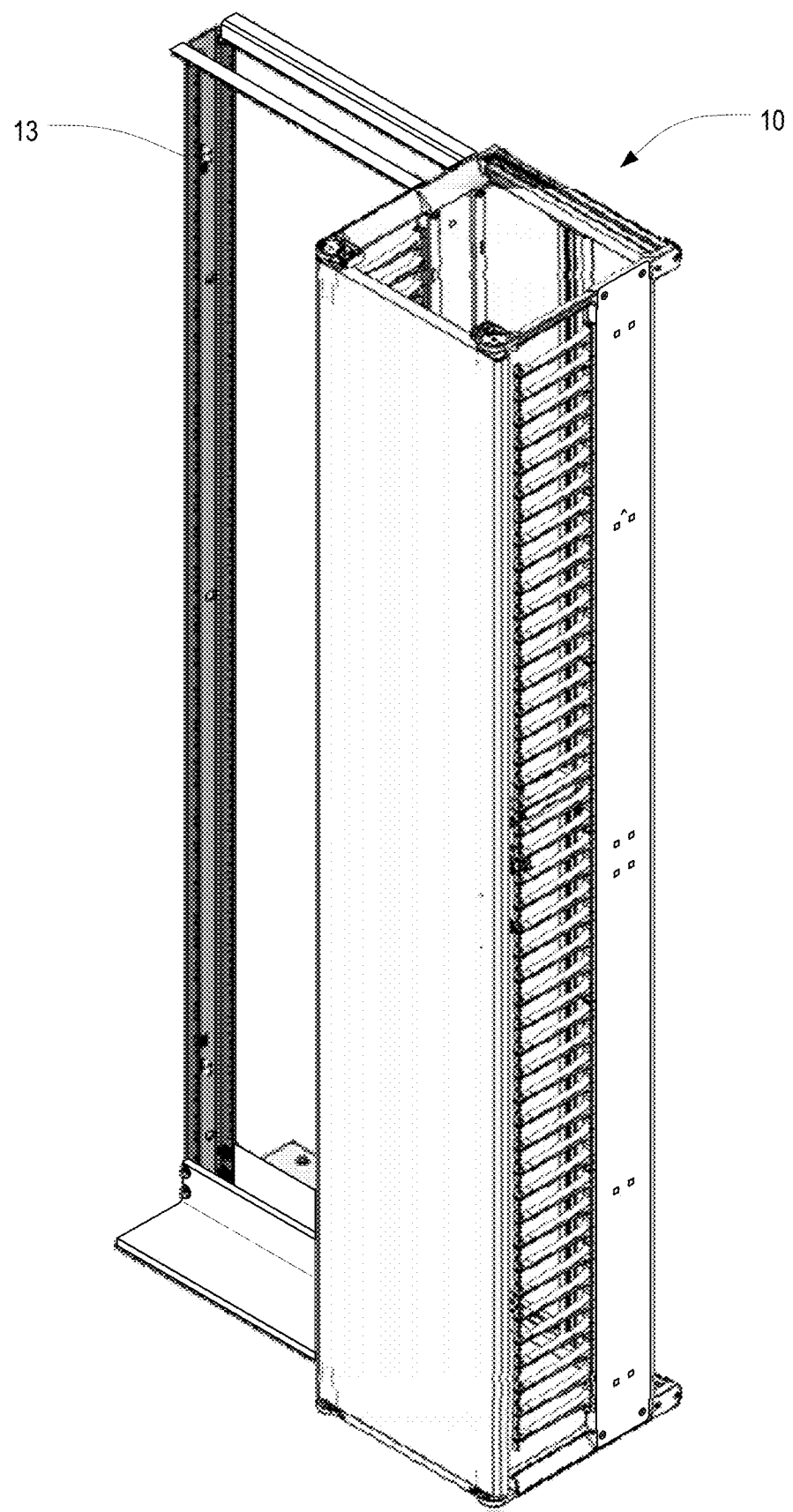
FIG. 3 is a front isometric view of the cable manager of FIG. 1, shown attached to a two-post mounting rack.

The cable manager 10 of FIGS. 1 and 2 is often used with racks, enclosures, and other equipment to address the needs of cable routing to, from, and around such equipment. In this regard, FIG. 3 is a front isometric view of the cable manager 10 of FIG. 1, shown attached to a two-post mounting rack 13. It will be appreciated, however, that the cable manager 10 may be used with other equipment or in some cases even without any other adjacent equipment. Furthermore, it will be appreciated that many of the features of the cable manager 10 may be incorporated into other IT structures, such as electronic equipment enclosures, and even into some non-IT structures.

It will be also appreciated that many or all of the features of the cable manager 10 of FIGS. 1 and 2 may be incorporated into double-sided cable managers and other structures. For example, FIG. 4A is an isometric view of a double-sided cable manager 210 in accordance with a preferred embodiment of the present invention, and FIG. 4B is an isometric close-up partial view of the double-sided cable manager 210 of FIG. 4A.

Figure 5:
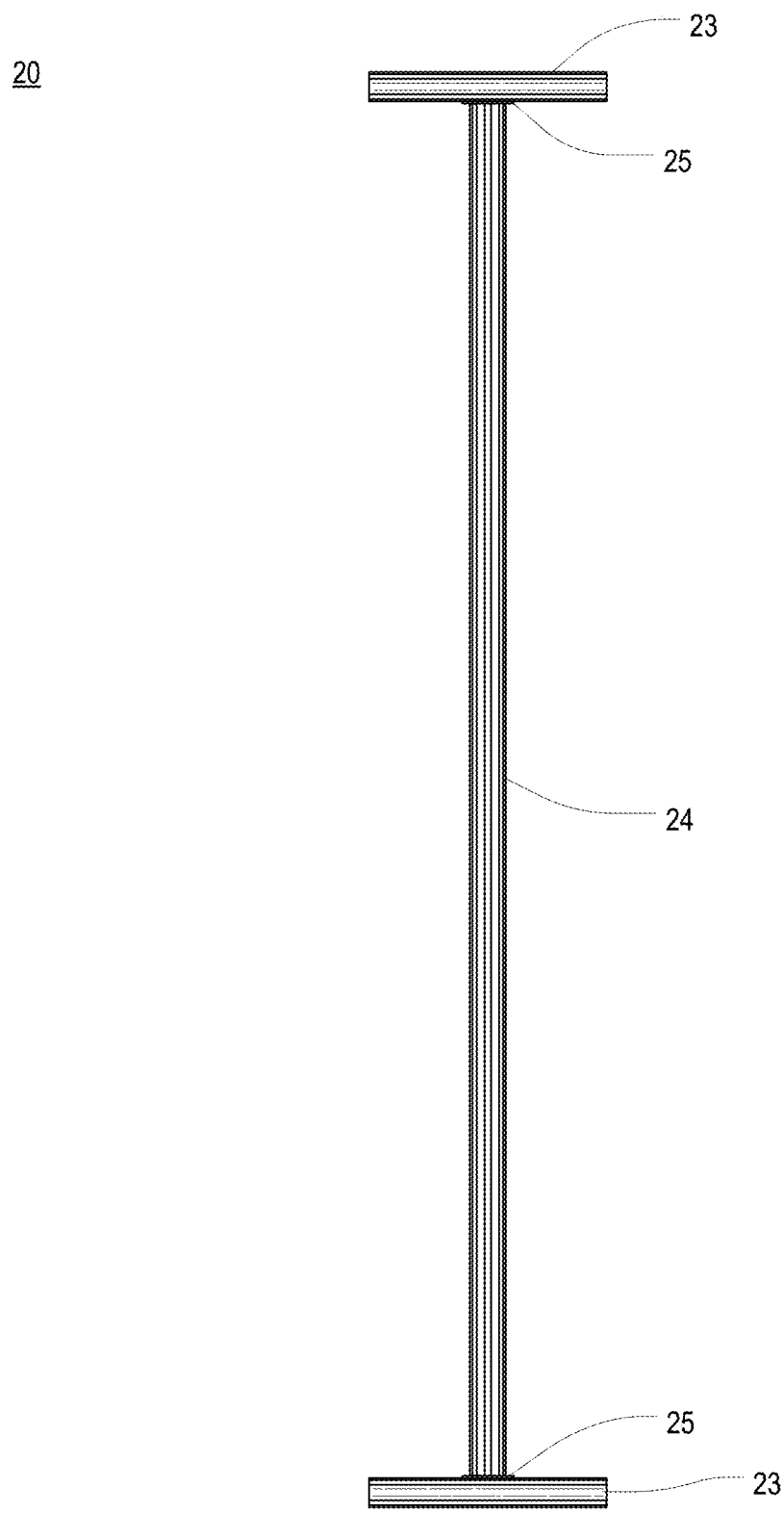
FIG. 5 is a front elevation view of the backbone assembly of FIG. 2.
Figure 6:
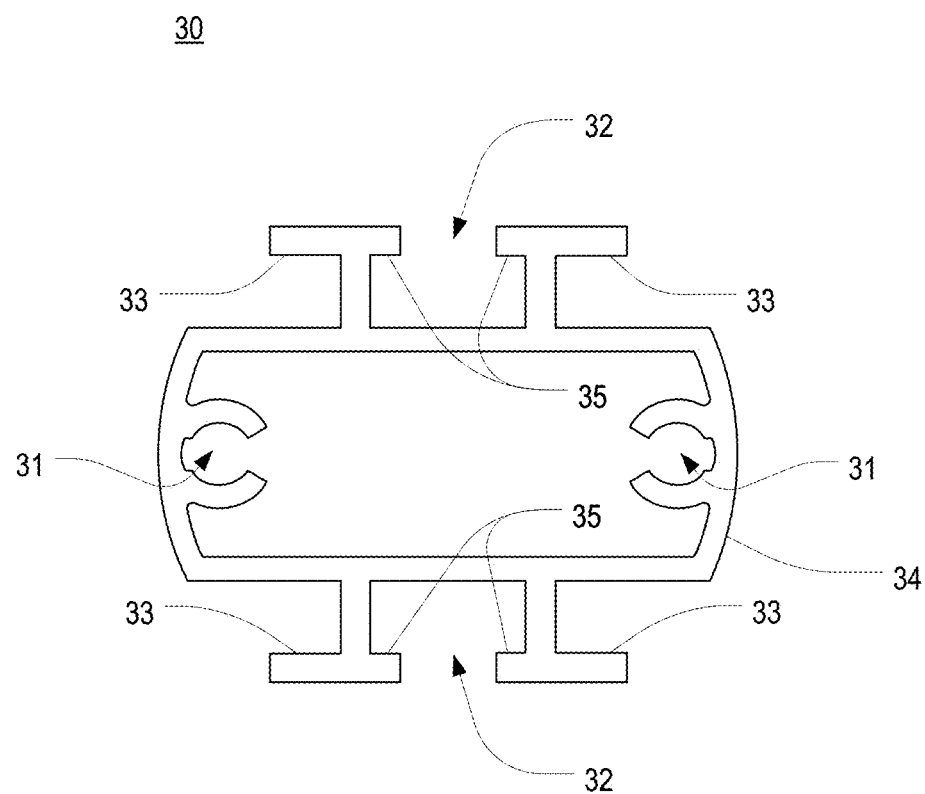
FIG. 6 is an end view of an extrusion used for the spine member and lateral members of the backbone assembly of FIG. 5.

FIG. 5 is a front elevation view of the backbone assembly 20 of FIG. 2. As shown therein, the backbone assembly 20 includes a spine member 24 and a plurality of lateral members 23. In at least some embodiments, each spine member 24 and lateral member 23 utilizes an extruded construction, and in at least some of these embodiments, each spine member 24 and lateral member 23 utilize the same cross-section. In this regard, FIG. 6 is an end view of an extrusion 30 used for the spine member 24 and lateral members 23 of FIG. 5. The extrusion 30 includes one or more fastener screw-in channels 31, one or more T-slot channels 32 with internal ledges 35, one or more additional ledges 33, and opposed sides having curvature of a minimum radius 34. The screw-in channels 31 are able to receive and retain screw-in fasteners, while the T-slot channels 32 are able to receive and retain the head of a bolt or other fastener, and/or, in a preferred embodiment, are able to receive and retain a drop-in nut or the like. In the illustrated embodiment (and with further reference to FIG. 7, discussed below), spring nuts 21 are received in the T-slot channels 32 and positioned in their desired locations along such channels 32 with the spring portion of the spring nuts helping to hold them in place via interference fit.

Figure 7:
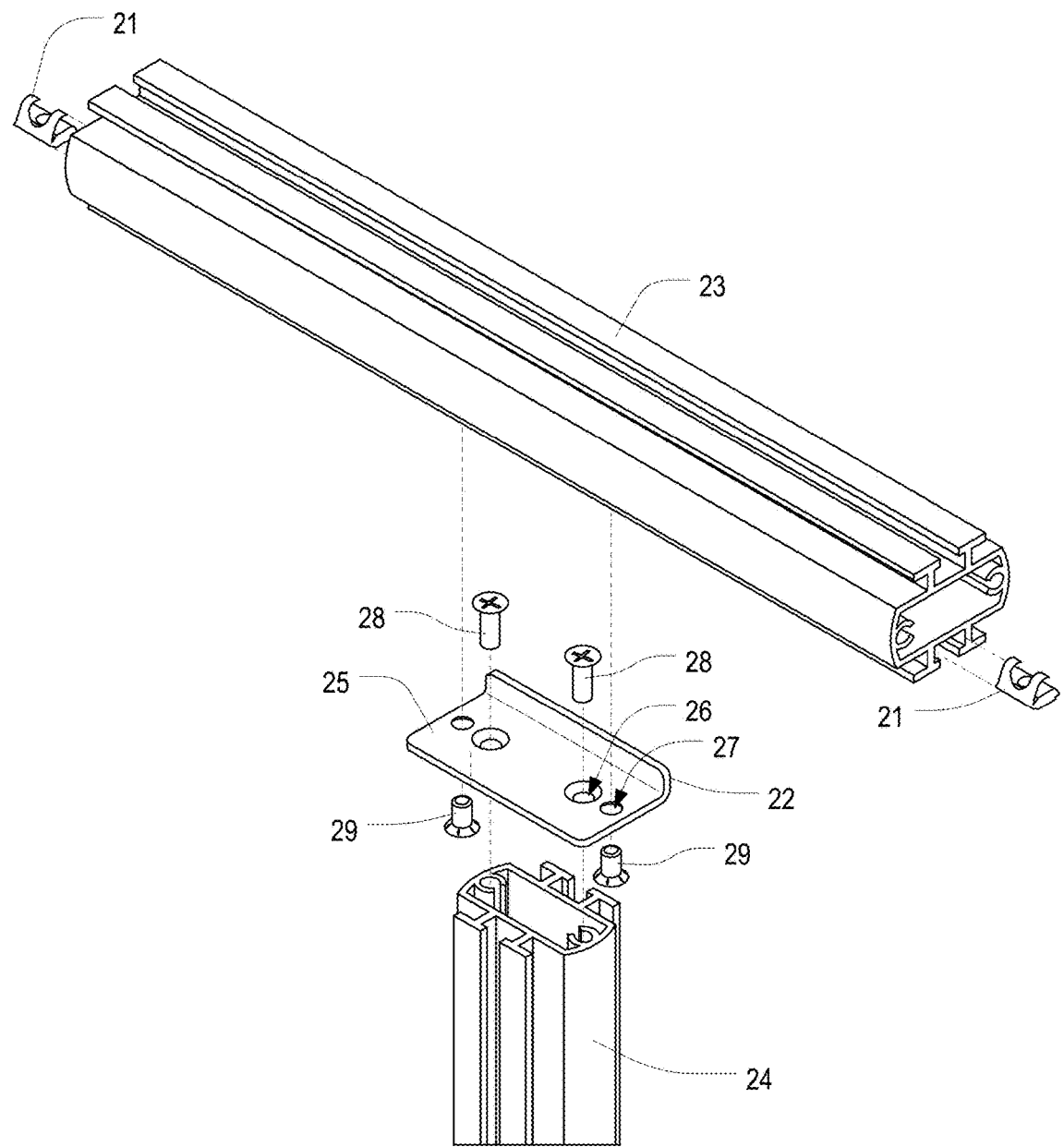
FIG. 7 is an exploded fragmentary orthogonal view of upper portions of the backbone assembly of FIG. 5.

Interconnection between each lateral member 23 and spine member 24 may be facilitated using a mounting bracket 25. In this regard, FIG. 7 is an exploded fragmentary orthogonal view of upper portions of the backbone assembly 20 of FIG. 5. The mounting bracket 25, which may be made of sheet metal, preferably includes a raised lip 22, apertures 26,27, and corresponding fasteners 28,29. The raised lip 22 may help align the bracket 25 along a side of lateral member 23 (and/or along an end of the spine member 24). A first set of fasteners 28 extend through corresponding apertures 26 and into the screw-in channels 31 in the extrusion 30, while a second set of fasteners 29 extend through corresponding apertures 27 and into the spring nuts 21 located in a T-slot channel 32 of the lateral member 23.

Figure 8:
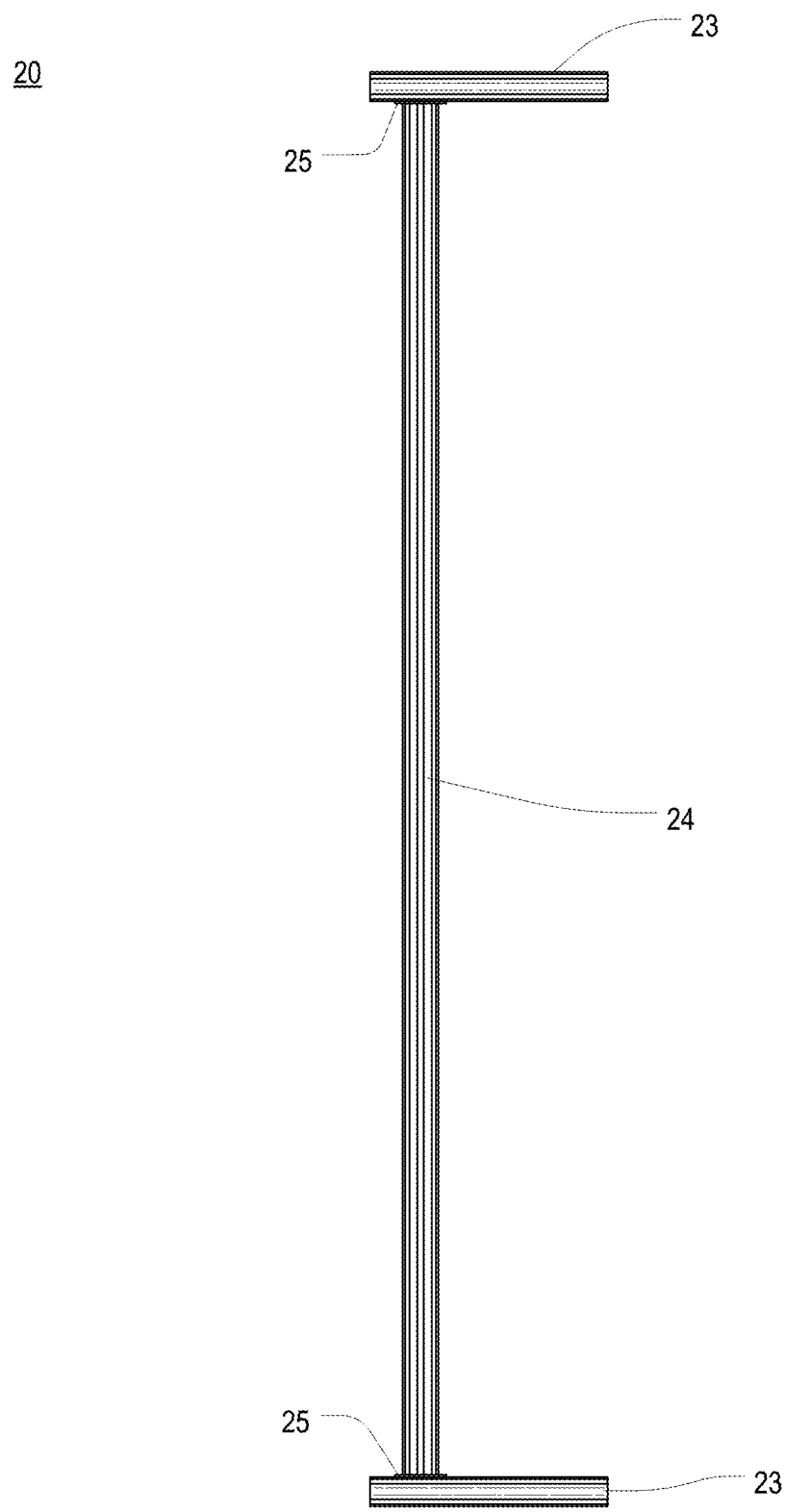
FIG. 8 is a front elevation view of the backbone assembly of FIG. 2, shown with the spine member disposed toward a side thereof.
Figure 9:
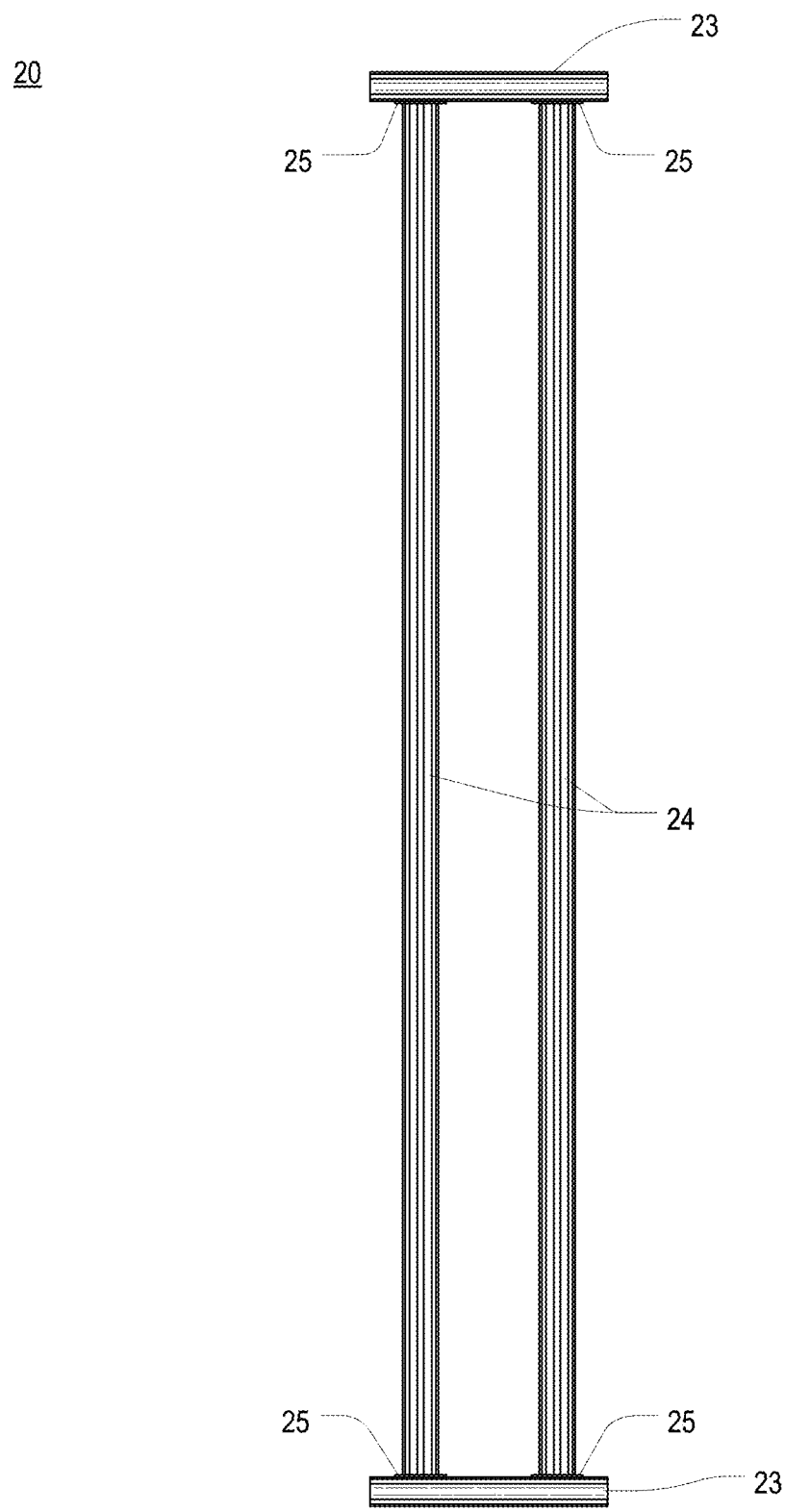
FIG. 9 is a front elevation view of the backbone assembly of FIG. 8, shown with two spine members installed between the top and bottom lateral members.

By using an extruded construction, the end of a spine member 24 may be positioned at any desired location along the length of the lateral member 23, with adjustment of such position being infinite along the length. Thus, although the spine member 24 in FIG. 5 is shown as being centered between the top and bottom lateral members 23, it will be appreciated that the spine member 24 may be installed or repositioned elsewhere. For example, FIG. 8 is a front elevation view of the backbone assembly 20 of FIG. 2, shown with the spine member 24 disposed toward a side thereof. Furthermore, additional spine members 24 may be added if desired. For example, FIG. 9 is a front elevation view of the backbone assembly 20 of FIG. 8, shown with two spine members 24 installed between the top and bottom lateral members 23.

Figure 10:
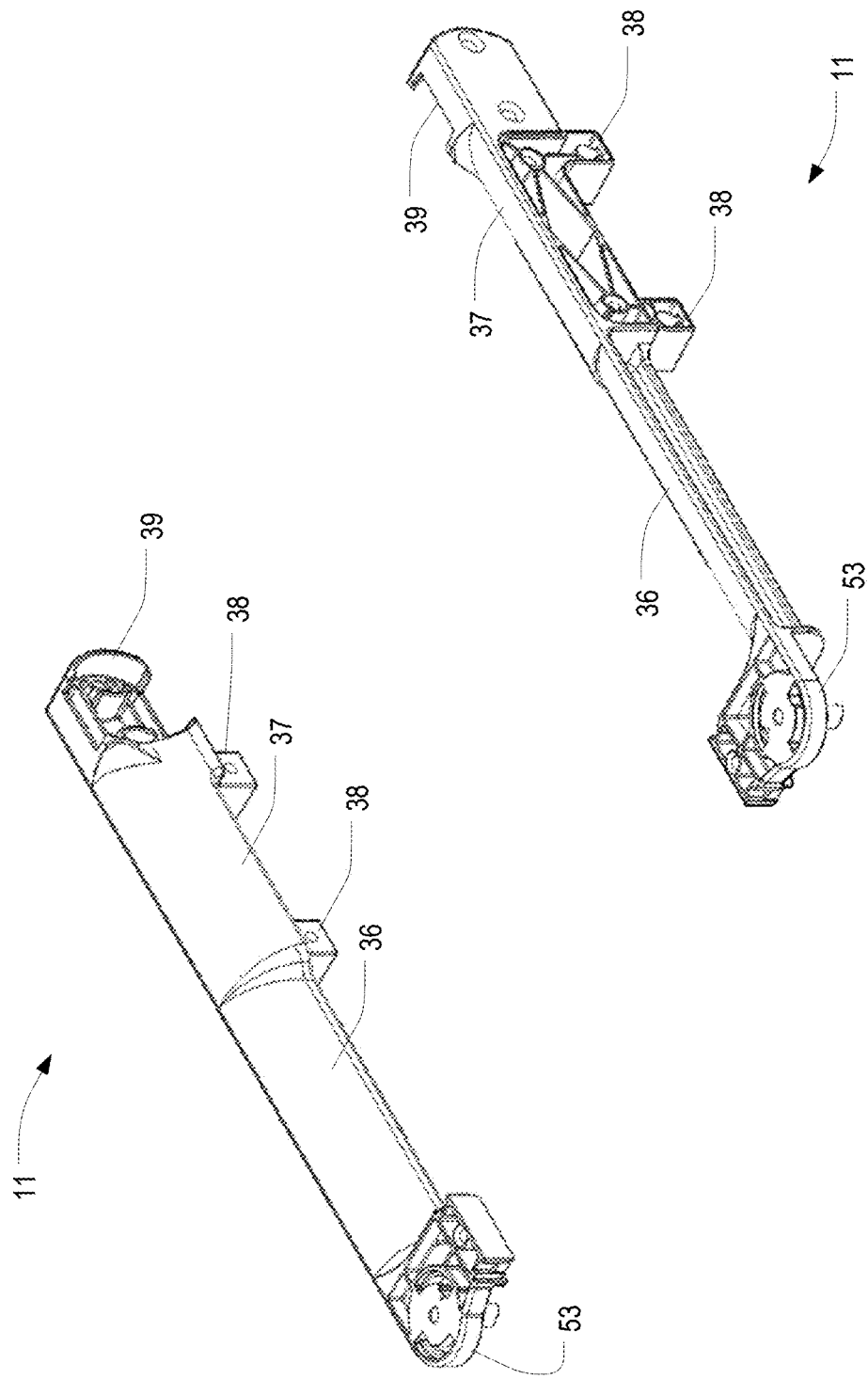
FIG. 10 is an orthogonal view of a pair of support arms of the cable manager of FIG. 1.

FIG. 10 is an orthogonal view of a pair of support arms 11 of the cable manager 10 of FIG. 1. The support arms 11 include first and second radiused surfaces 36,37, fittings 38 for connection to the side walls 12, a lateral member interface 39, and a door support 53. The radiused surfaces 36,37 provide proper curvature for cables routed out of the top (or bottom) of the cable manager 10. The lateral member interface 38 may be connected to an end of a lateral member 23 via fasteners (not shown) inserted into the screw-in channels 31 thereof. Details of the door supports 53, which interface with hinge assemblies 130 on the door assembly 18, are provided below.

Advantageously, various embodiments of the cable manager design of the present invention use a combination of extruded, die-cast, injection-molded and sheet-metal parts to provide tracks for attaching accessories and other parts or equipment. This allows "infinite" installation and adjustment of accessories along the track and facilitates the use of clamps or other attachment methods that can eliminate the need for hardware. Features for maintaining bend radii, attaching accessories, doors and other peripheral parts can be integrated into the extruded, die-cast or injection-molded parts of the frame to further increase the functionality and flexibility of the manager when compared to sheet-metal designs. The arms and extrusions further provide gentle cable entry and exit guides to maintain cable bend radii and support. These parts and features can also be applied in a double-sided configuration where cable or equipment management is desired within or around both the front and rear portions of the manager.

Figure 11:
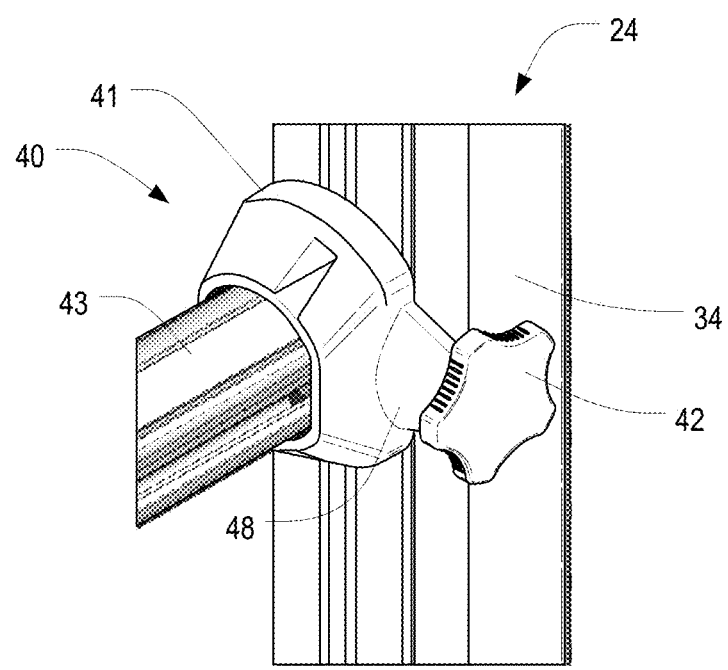
FIG. 11 is an enlarged orthogonal view of a portion of the accessory rod assembly of FIG. 2, shown mounted on a spine member of the backbone assembly.
Figure 12:
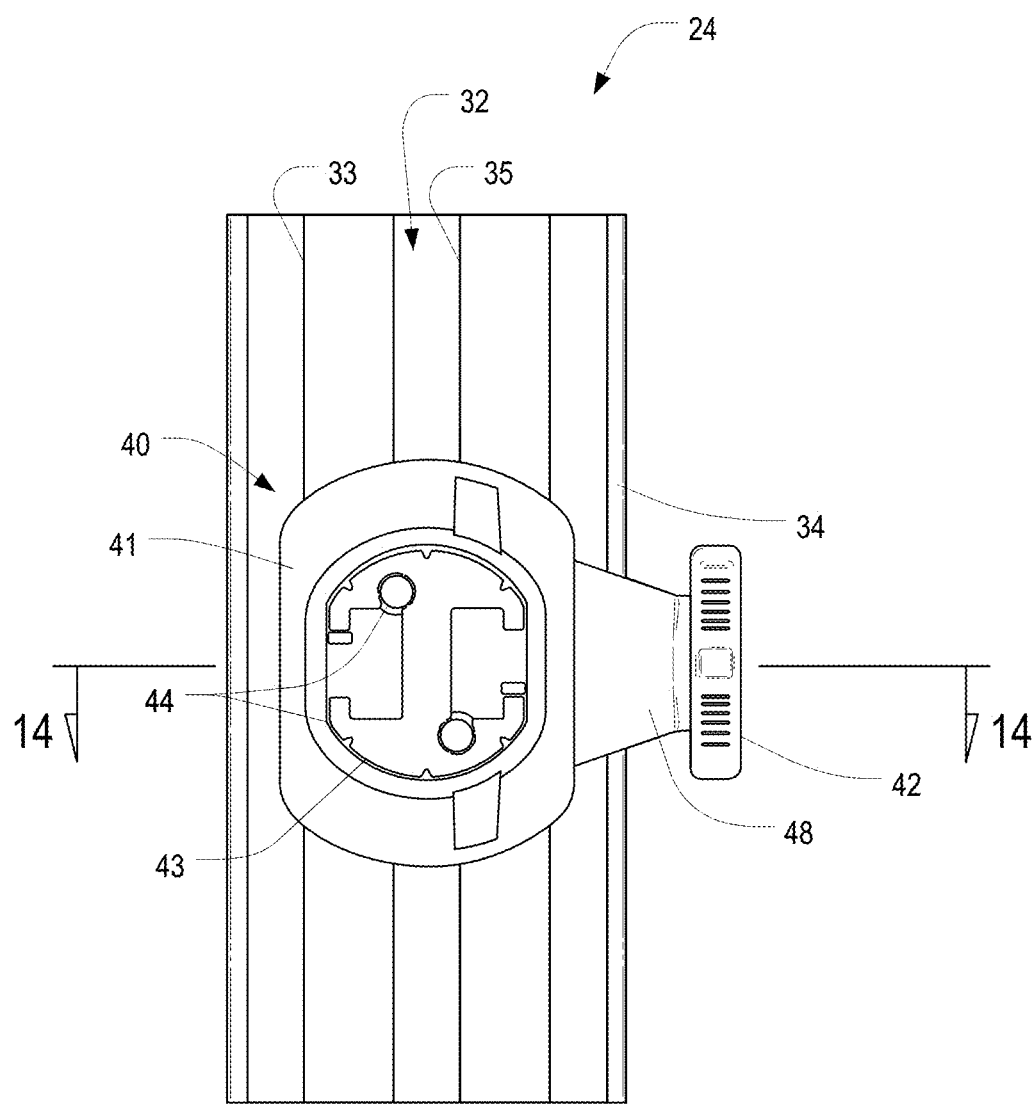
FIG. 12 is a front view of the accessory rod assembly of FIG. 11, shown with the end cap removed.
Figure 13:
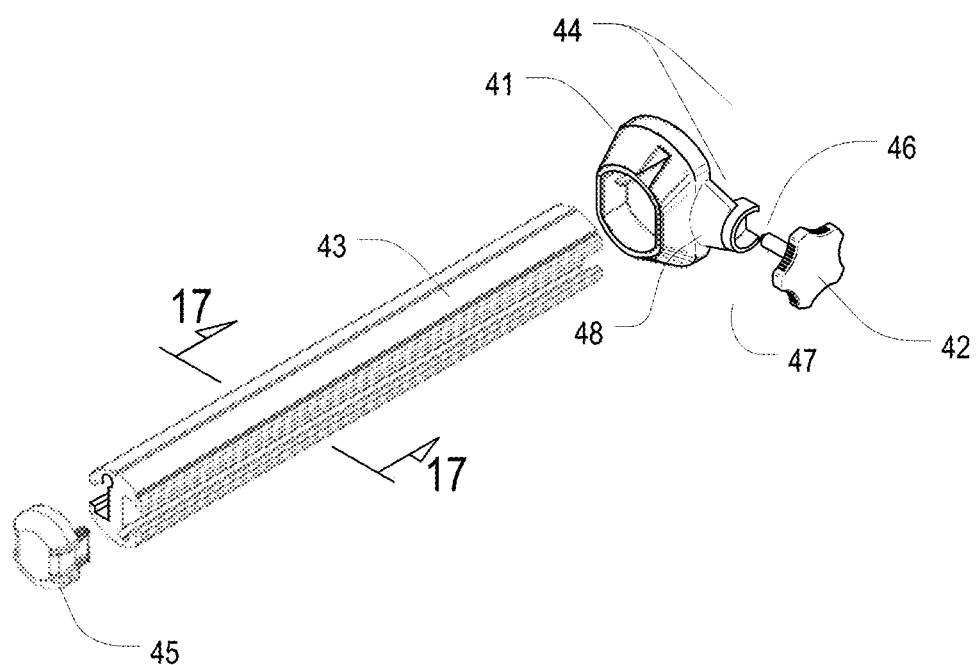
FIG. 13 is an exploded orthogonal view of the accessory rod assembly of FIG. 11, shown in isolation.

FIG. 11 is an enlarged orthogonal view of a portion of the accessory rod assembly 40 of FIG. 2, shown mounted on a spine member 24 of the backbone assembly 20, while FIG. 12 is a front view of the accessory rod assembly 40 of FIG. 11, shown with the end cap 45 removed, and FIG. 13 is an exploded orthogonal view of the accessory rod assembly 40 of FIG. 11, shown in isolation. As shown in FIGS. 11, 12, and 13, the accessory rod assembly 40 includes a base member 41, a knob 42, a rod 43, one or more fasteners 44, and an end cap 45. The knob 42 is threaded into the base member 41 such that a distal end 46 of the threaded portion 47 of the knob 42 can be tightened against a corresponding portion of a spine member 24 or other structure. The threaded portion 48 of the base member 41 has a tapered, angled exterior surface to provide minimum curvature in the area where the knob 42 connects to the base member 41, and a shroud 49 is provided to interface with the underside of the knob 42 so as to shield cables (not shown) from being abraded or being pinched or caught by the knob threads. The function and operation of the knob 42 are described below.

Figure 14:
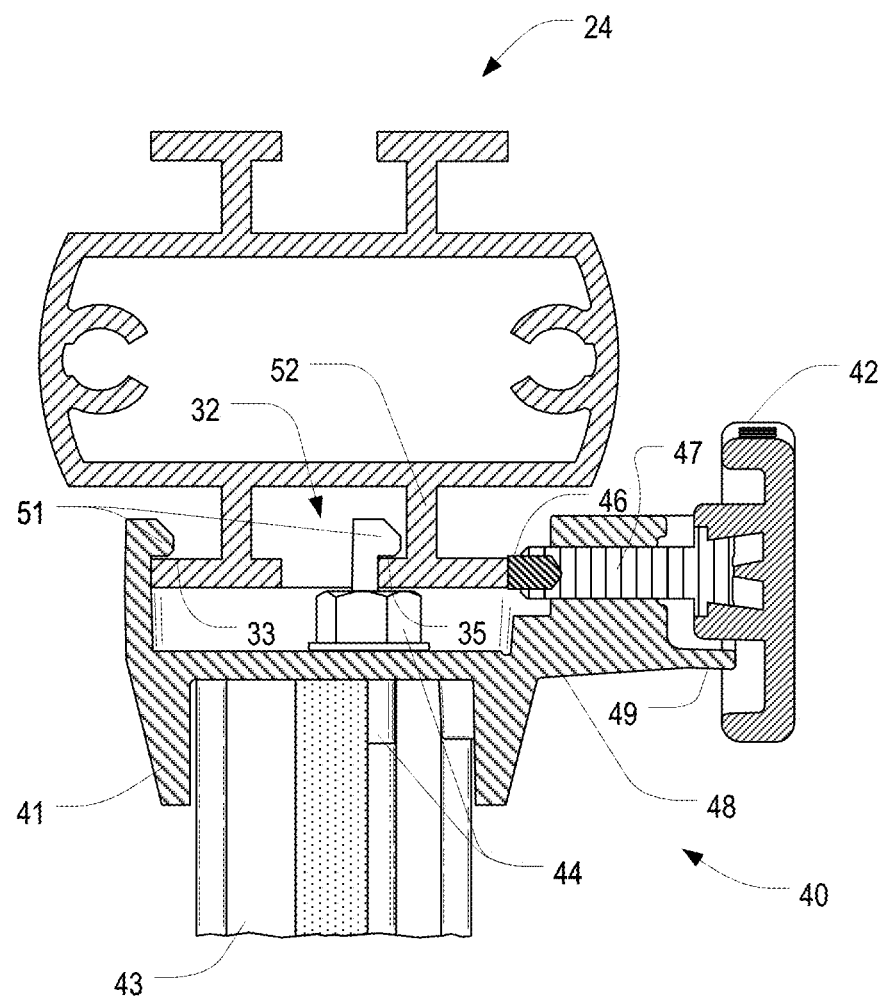
FIG. 14 is a fragmentary top cross-sectional view of the accessory rod assembly and spine member of FIG. 12, taken along line 14-14.

FIG. 14 is a fragmentary top cross-sectional view of the accessory rod assembly 40 and spine member 24 of FIG. 12, taken along line 14-14. As shown therein, the base member 41 is held in place on the spine member 24 via hooks 51 extending from the rear of the base member 41 and by the distal end 46 of the knob 42. The hooks 51 fit around ledges 33,35 of the spine member 24, while the distal end 46 of the knob 42 is pressed against a wall 52 of the T-slot channel 32, thus holding the hooks 51 in place. Although not specifically illustrated, the accessory rod assembly 40 may likewise be mounted on a lateral member 23 of the backbone assembly 20.

Figure 15:
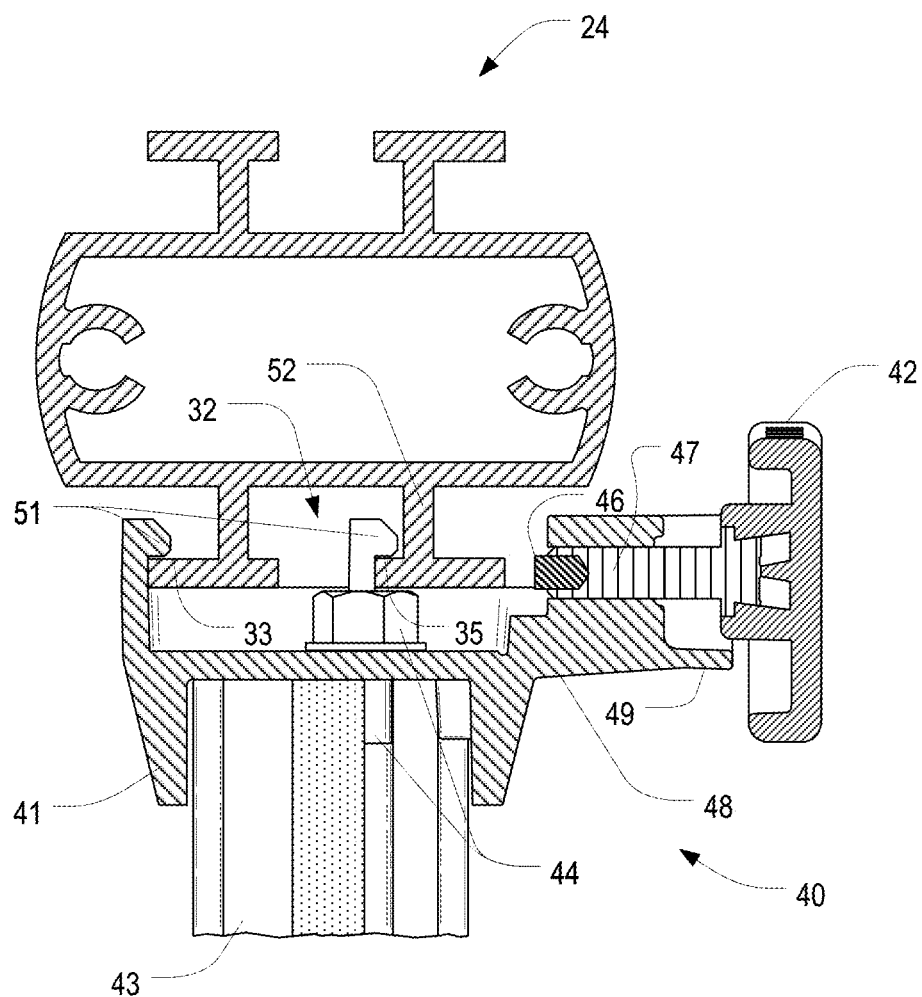
FIG. 15 is a fragmentary top cross-sectional view similar to that of FIG. 14, but with the cam lever rotated upward to remove the bearing surface of the cam teeth from the T-slot channel wall.
Figure 16:
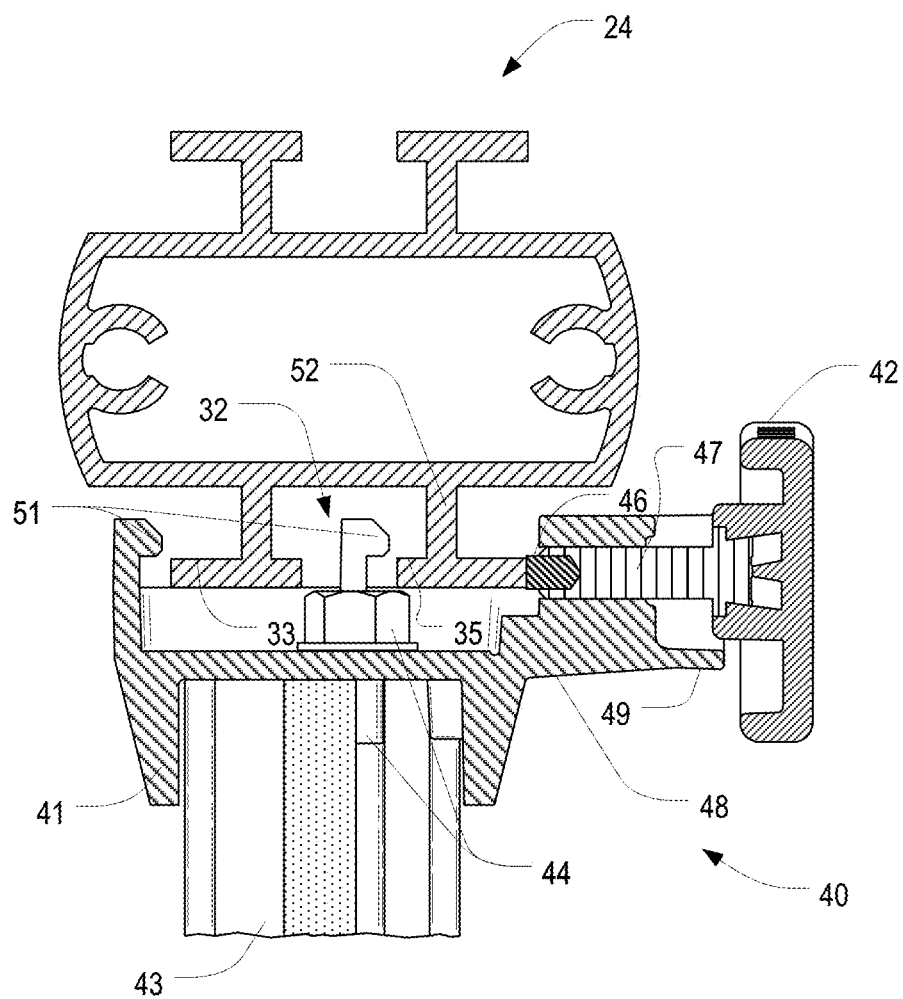
FIG. 16 is a fragmentary top cross-sectional view similar to that of FIG. 15, but with the accessory rod assembly shifted sideways to permit removal or movement thereof.

Advantageously, the knob 42 facilitates the easy attachment, removal, and/or repositioning of the accessory rod assembly 40 to or on the spine member 24. In this regard, FIG. 15 is a fragmentary top cross-sectional view similar to that of FIG. 14, but with the knob 42 unscrewed to remove the bearing surface of the distal end 46 from the T-slot channel wall 52, and FIG. 16 is a fragmentary top cross-sectional view similar to that of FIG. 15, but with the entire accessory rod assembly 40 shifted sideways to permit removal or movement thereof. Once the accessory rod assembly 40 is in the desired located along the spine member 24 or lateral member 23, it may be installed by reversing the process of FIGS. 14-16 such that the hooks 51 are engaged on the ledges 33,35 and the knob 42 screwed inward until the distal end 46 bears against the T-slot channel wall 52.

Figure 17:
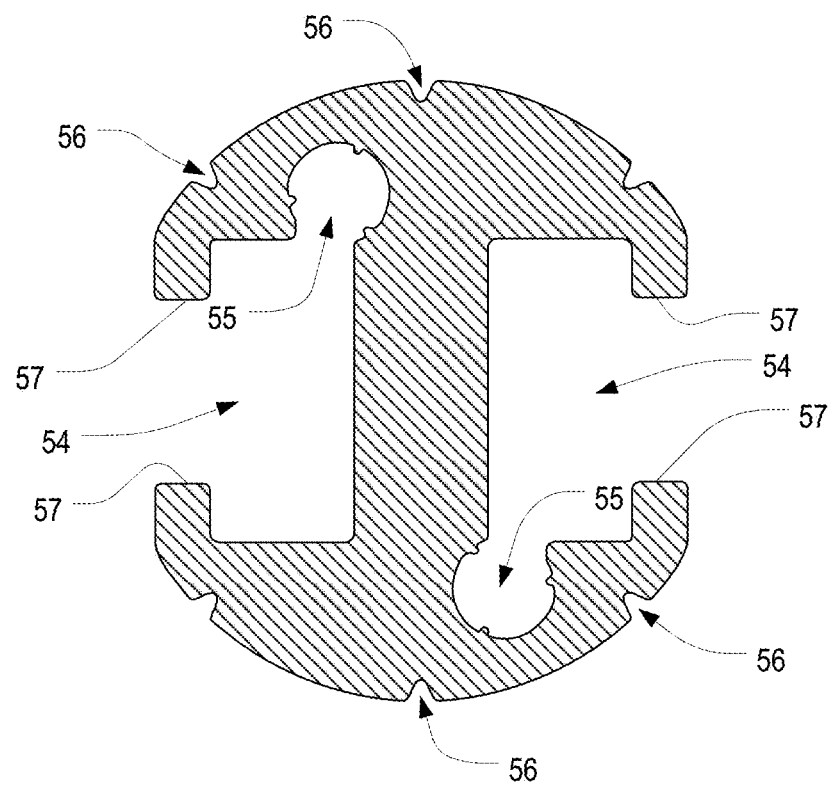
FIG. 17 is a front cross-sectional view of the accessory rod of FIG. 13, taken along line 17-17, shown in isolation.

In at least some embodiments, the rod 43 utilizes an extruded construction. In this regard, FIG. 17 is a front cross-sectional view of the accessory rod 43 of FIG. 13, taken along line 17-17, shown in isolation. As shown therein, the rod 43 has a generally uniform cross-section and includes a partially cylindrical overall profile, one or more drop-in T-slot channels 54 formed by ledges 57, one or more fastener screw-in channels 55 that may or may not be extensions of the T-slot channels 54, and a plurality of grip channels 56. The fastener screw-in channels 55 are used to attach the rod 43 to the base member 41 via fasteners 44, while the T-slot channels 54 and grip channels 56 may be utilized to attach other structures to the rods 43. The T-slot channels 54 may be utilized conventionally, wherein structures are attached to the rod 43 using fasteners (not shown) where either the head of a fastener, or a threaded nut or similar structure that receives a fastener, is inserted into a T-slot channel 54 and tightened. However, various accessories are known or may be designed to utilize the T-slot channels 54 and/or grip channels 56 in novel ways. Some such examples of various accessories are further described below.

Figure 18:
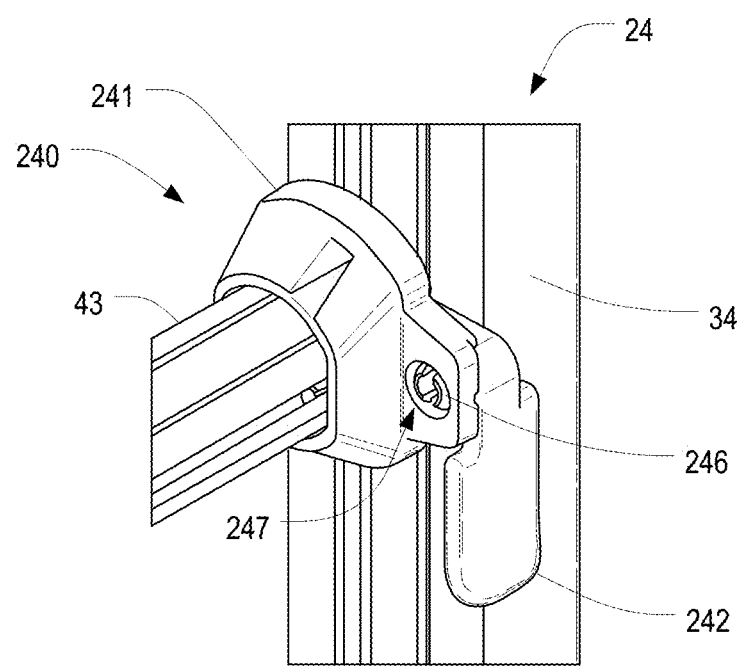
FIG. 18 is an enlarged orthogonal view of a portion of an alternative accessory rod assembly, for use in the cable manager of FIG. 2, shown mounted on a spine member of the backbone assembly.
Figure 19:
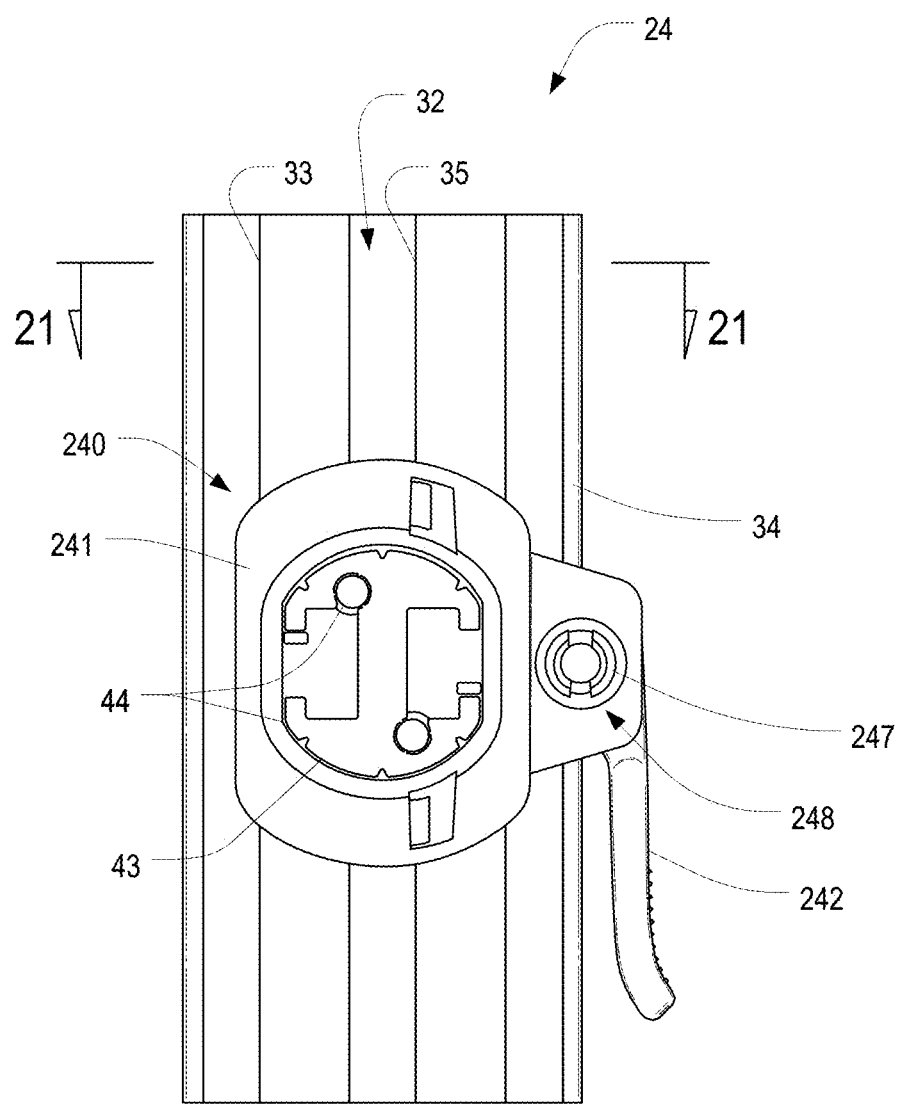
FIG. 19 is a front view of the accessory rod assembly of FIG. 18, shown with the end cap removed.
Figure 20:
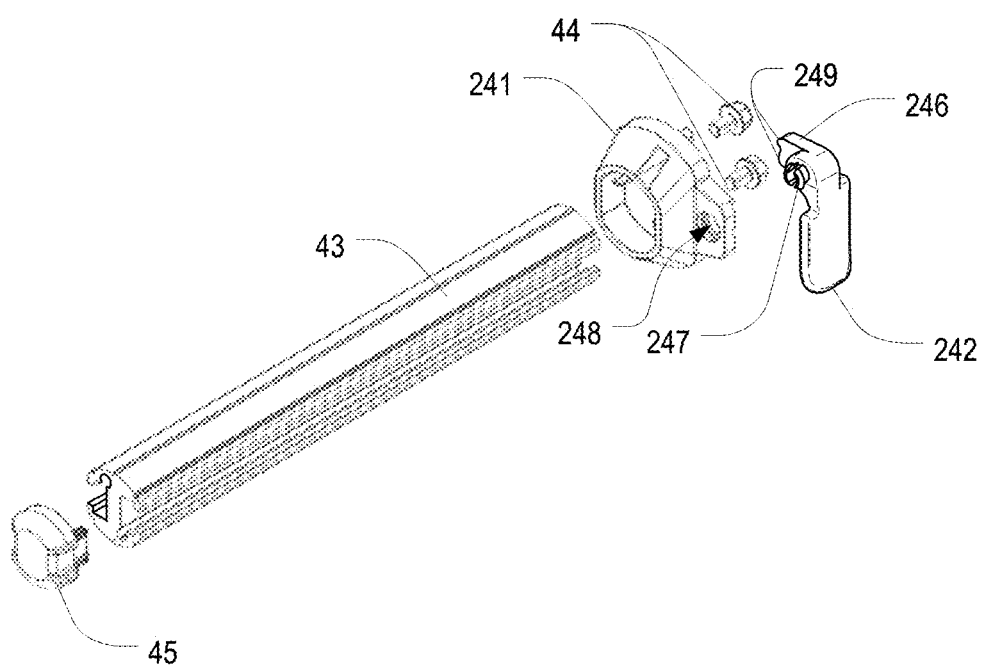
FIG. 20 is an exploded orthogonal view of the accessory rod assembly of FIG. 18, shown in isolation.

FIG. 18 is an enlarged orthogonal view of a portion of an alternative accessory rod assembly 240, for use in the cable manager 10 of FIG. 2, shown mounted on a spine member 24 of the backbone assembly 20, while FIG. 19 is a front view of the accessory rod assembly 240 of FIG. 18, shown with the end cap 45 removed, and FIG. 20 is an exploded orthogonal view of the accessory rod assembly 240 of FIG. 18, shown in isolation. As shown in FIGS. 18, 19, and 20, the accessory rod assembly 240 includes a base member 241, a cam lever 242, a rod 43, one or more fasteners 44, and an end cap 45. The cam lever 242 includes a cam 246 and a snap feature 247, and the base member 241 includes a snap receptacle 248. The snap feature 247 is installed in, and rotates within, the snap receptacle 248, thus allowing rotation of the cam lever 242 relative to the base member 241. However, other attachment means may be used instead of the snap feature 247 and snap receptacle 248 (so long as they allow rotation). The function and operation of the cam lever 242 are described below.

Figure 21:
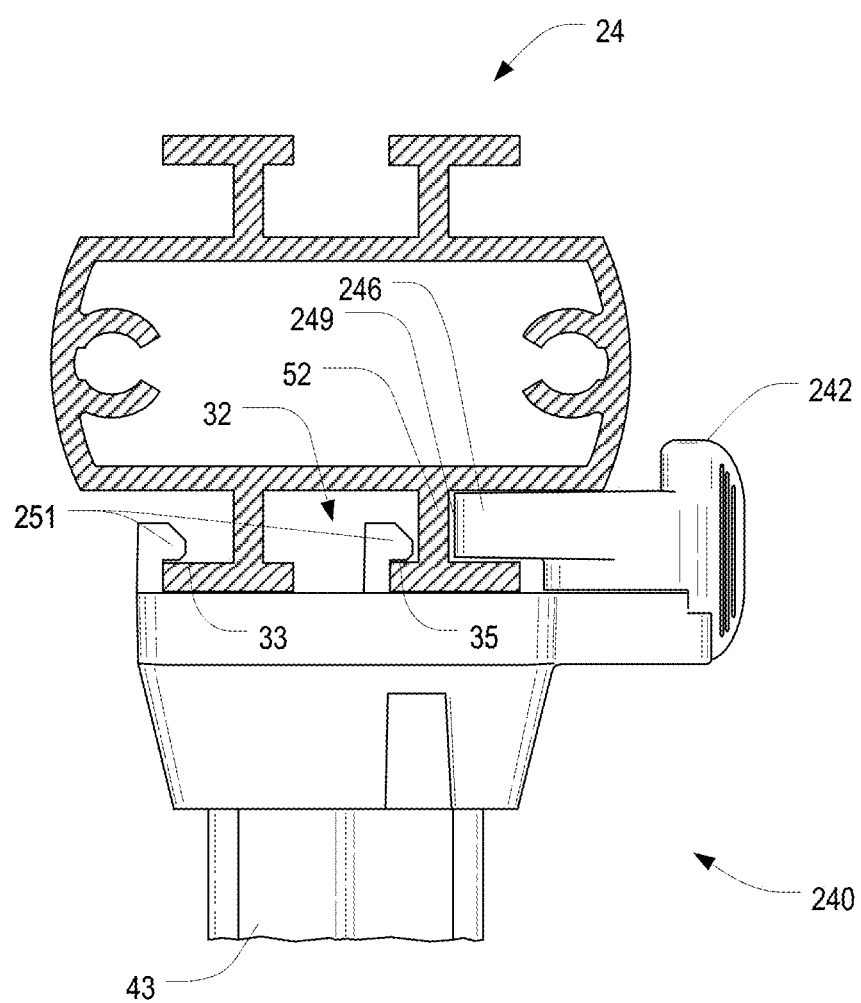
FIG. 21 is a fragmentary top cross-sectional view of the accessory rod assembly and spine member of FIG. 19, taken along line 21-21.

FIG. 21 is a fragmentary top cross-sectional view of the accessory rod assembly 240 and spine member 24 of FIG. 19, taken along line 21-21. As shown therein, the base member 241 is held in place on the spine member 24 via hooks 251 extending from the rear of the base member 241 and by the cam 246. The hooks 251 fit around ledges 33,35 of the spine member 24, while one or both cam teeth 249 of the cam 246 are pressed against a wall 52 of the T-slot channel 32, thus holding the hooks 251 in place. Although not specifically illustrated, the accessory rod assembly 240 may likewise be mounted on a lateral member 23 of the backbone assembly 20.

Figure 22:
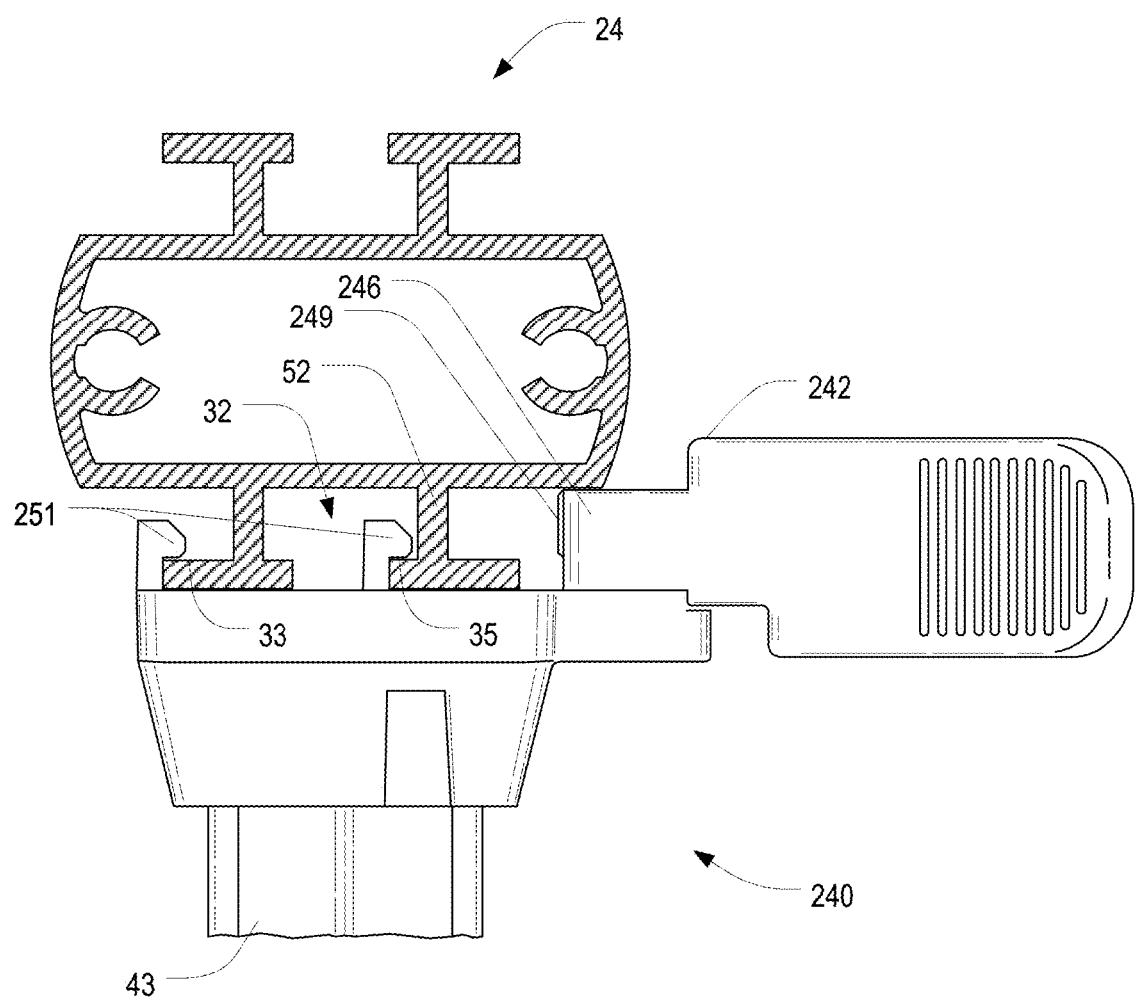
FIG. 22 is a fragmentary top cross-sectional view similar to that of FIG. 21, but with the cam lever rotated upward to remove the bearing surface of the cam teeth from the T-slot channel wall.
Figure 23:
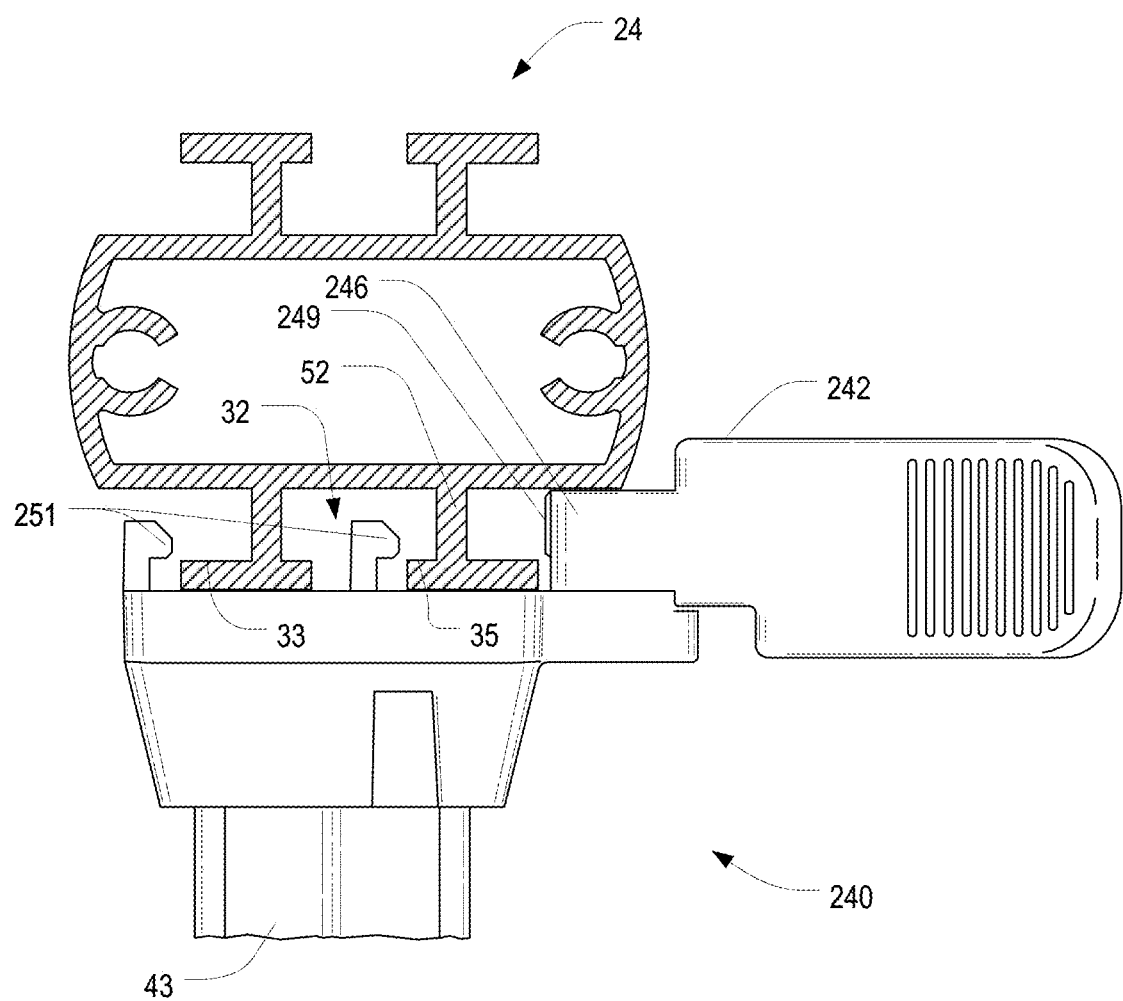
FIG. 23 is a fragmentary top cross-sectional view similar to that of FIG. 22, but with the accessory rod assembly shifted sideways to permit removal or movement thereof.

Advantageously, the cam lever 242 facilitates the easy attachment, removal, and/or repositioning of the accessory rod assembly 240 to or on the spine member 24. In this regard, FIG. 22 is a fragmentary top cross-sectional view similar to that of FIG. 21, but with the cam lever rotated upward to remove the bearing surface of the cam teeth 249 from the T-slot channel wall 52, and FIG. 23 is a fragmentary top cross-sectional view similar to that of FIG. 22, but with the entire accessory rod assembly 240 shifted sideways to permit removal or movement thereof. Once the accessory rod assembly 240 is in the desired located along the spine member 24 or lateral member 23, it may be installed by reversing the process of FIGS. 21-23 such that the hooks 251 are engaged on the ledges 33,35 and the cam lever 242 rotated until the cam teeth 249 bear against the T-slot channel wall 52.

Figure 24:
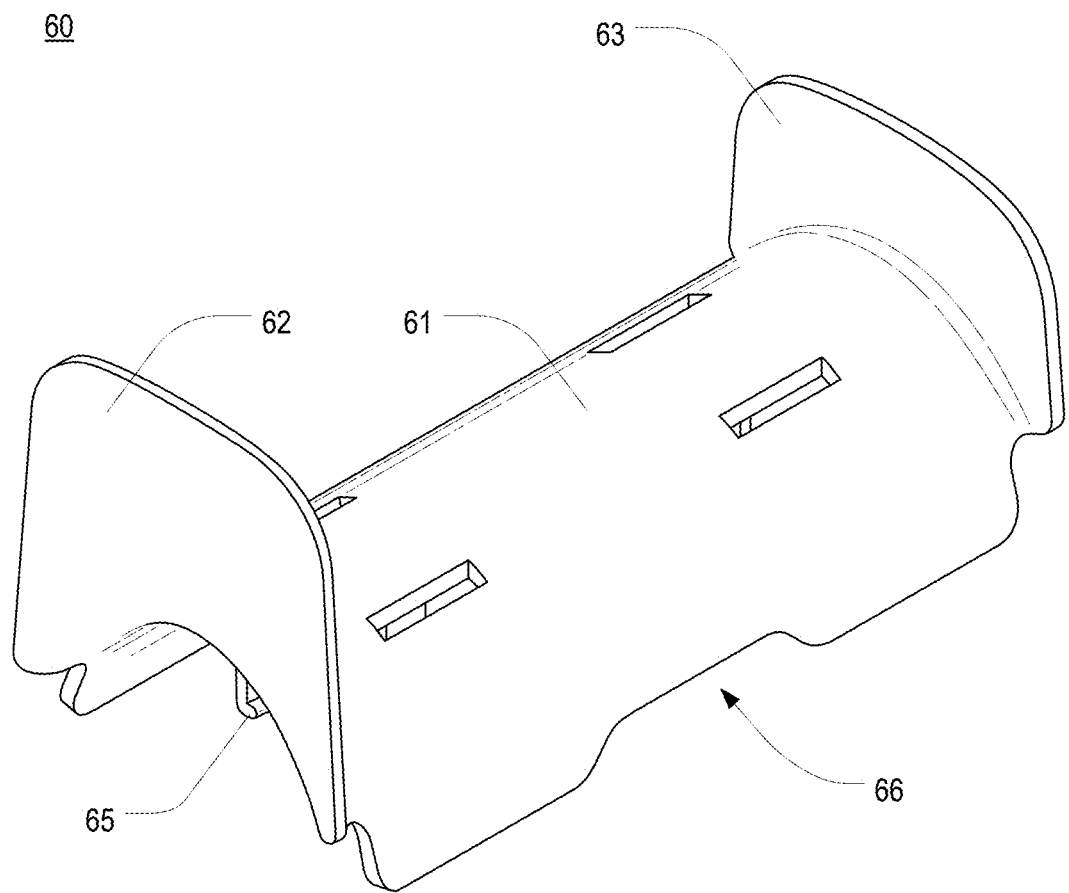
FIG. 24 is a top front isometric view of the half-spool accessory of FIG. 2.
Figure 25:
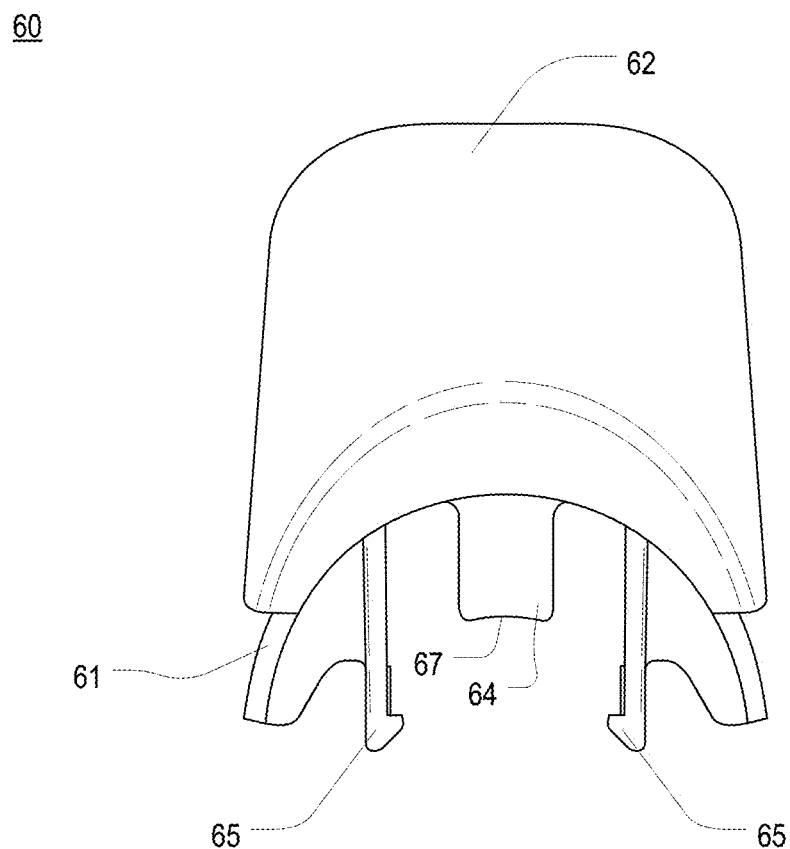
FIG. 25 is a front elevation view of the half-spool accessory of FIG. 2.

FIGS. 24 and 25 are a top front isometric view and a front elevation view, respectively, of the half-spool accessory 60 of FIG. 2. This accessory, which may be particularly suitable for routing large numbers of cables within the cable manager 10, includes a central portion 61 for carrying cables, front and rear end flanges 62,63 to help retain cables around or within the central spool portion 61, one or more standoffs 64, a plurality of resilient snaps 65, and one or more finger grips 66. The standoffs 64 (one shown in FIG. 25, but there may be more than one) help position the accessory 60 against the rod 43 of the accessory rod assembly 40, and may include a correspondingly curved surface 67 to provide a better fit against the surface of the rod 43. The resilient snaps 65 retain the accessory 60 on the rod 43, while the finger grips 66 provide a more convenient surface or edge for a user to grasp in order to remove the accessory 60 from the rod 43, all as further described below. The central portion 61 is preferably cylindrical (i.e., forms a portion of a cylinder) and conforms to industry cable bend radius standards. The joints between the central portion 61 and the arcuate flanges 62,63 are preferably also arcuate.

Figure 26:
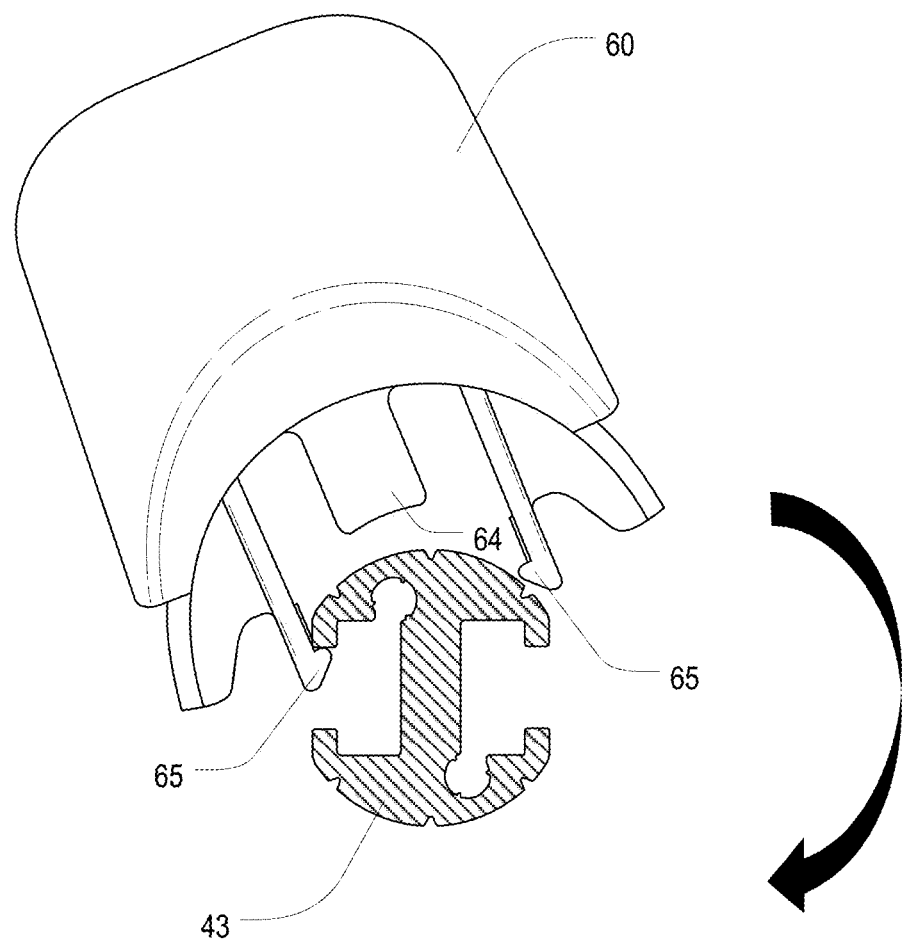
FIGS. 26-28 are front views illustrating the installation of half-spool accessories on a rod, for example of the accessory rod assembly, which is shown in isolation and in cross-section.
Figure 27:
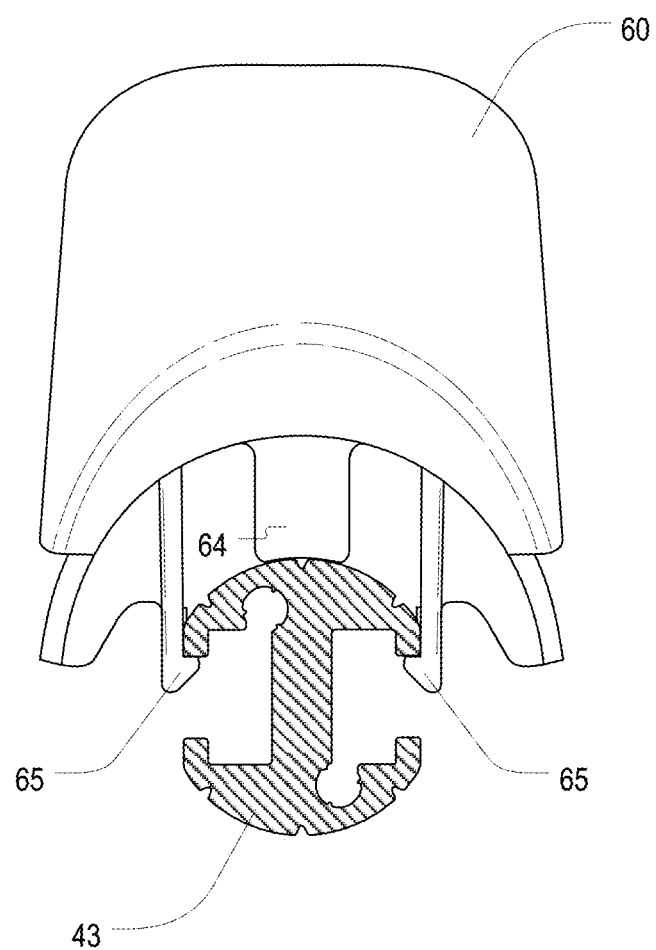
Figure 28:
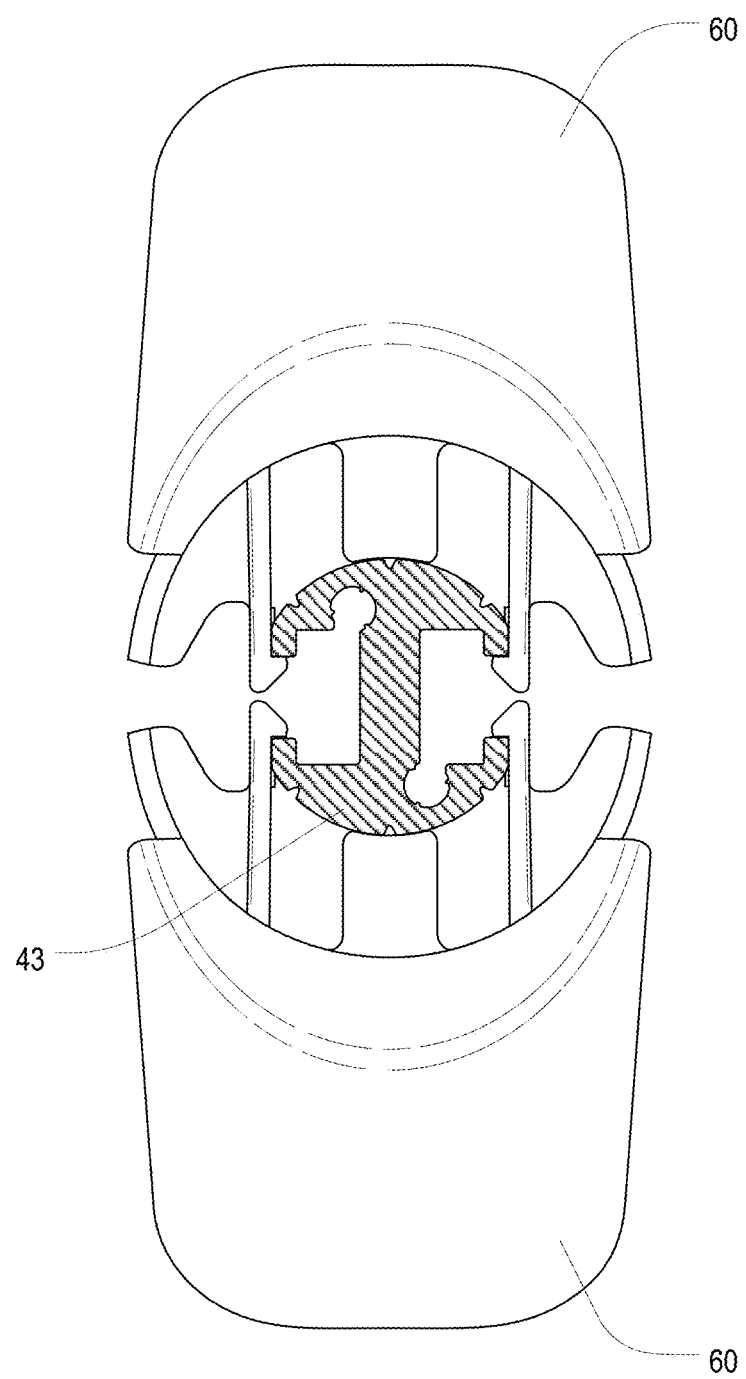

FIGS. 26-28 are front views illustrating the installation of half-spool accessories 60 on a rod 43, for example of the accessory rod assembly 40, which is shown in isolation and in cross-section. In FIG. 26, a first half-spool 60 is shown angled so that the snap(s) 65 along one side thereof can be hooked underneath a ledge 57 of the T-shaped channel 54 of the rod 43. With the first snap(s) 65 positioned, the accessory 60 may be rotated in the direction of the arrow until the snap(s) 65 along the other side are deflected sufficiently to allow them to latch into place around a ledge 57 on the opposite side of the rod 43, as shown in FIG. 27. A second accessory 60 can be installed in the same manner, as shown in FIG. 28, thereby allowing the creation of a nearly-complete cylinder through the combination of the respective central portions 61 in close proximity to one another.

Each half-spool accessory 60 may be removed in at least two ways. First, by gripping the accessory 60, such as via the finger grips 66, and pulling and/or twisting with sufficient force to deflect the snaps 65 along at least one side of the accessory 60, the accessory may be removed by reversing the steps used to attach it. Second, because the rod 43 is of extruded construction, the accessory 60 may be removed by pulling it along the length of the rod 43 until it slips off the end thereof. In some embodiments, the end cap 45 of the accessory rod assembly 40 may be detached to facilitate such removal, while in other embodiments, the shape of the end cap 45 is selected such that the snaps 65 can be pulled off the rod 43 without removal of the end cap 45.

Figure 29A:
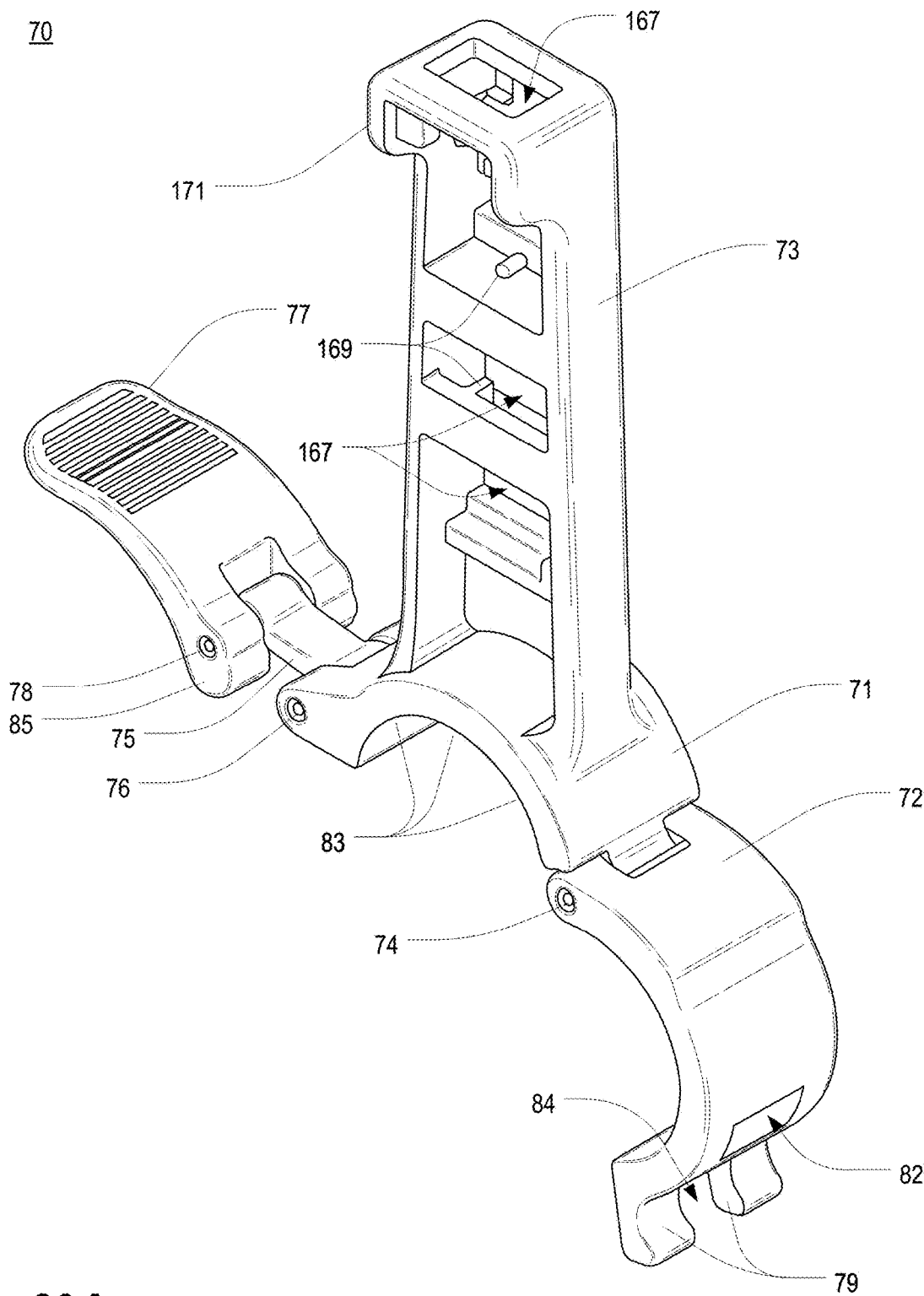
FIGS. 29A and 29B are a top front isometric view and a front elevation view, respectively, of the cable finger accessory of FIG. 2, shown in an open, unclamped state.
Figure 29B:
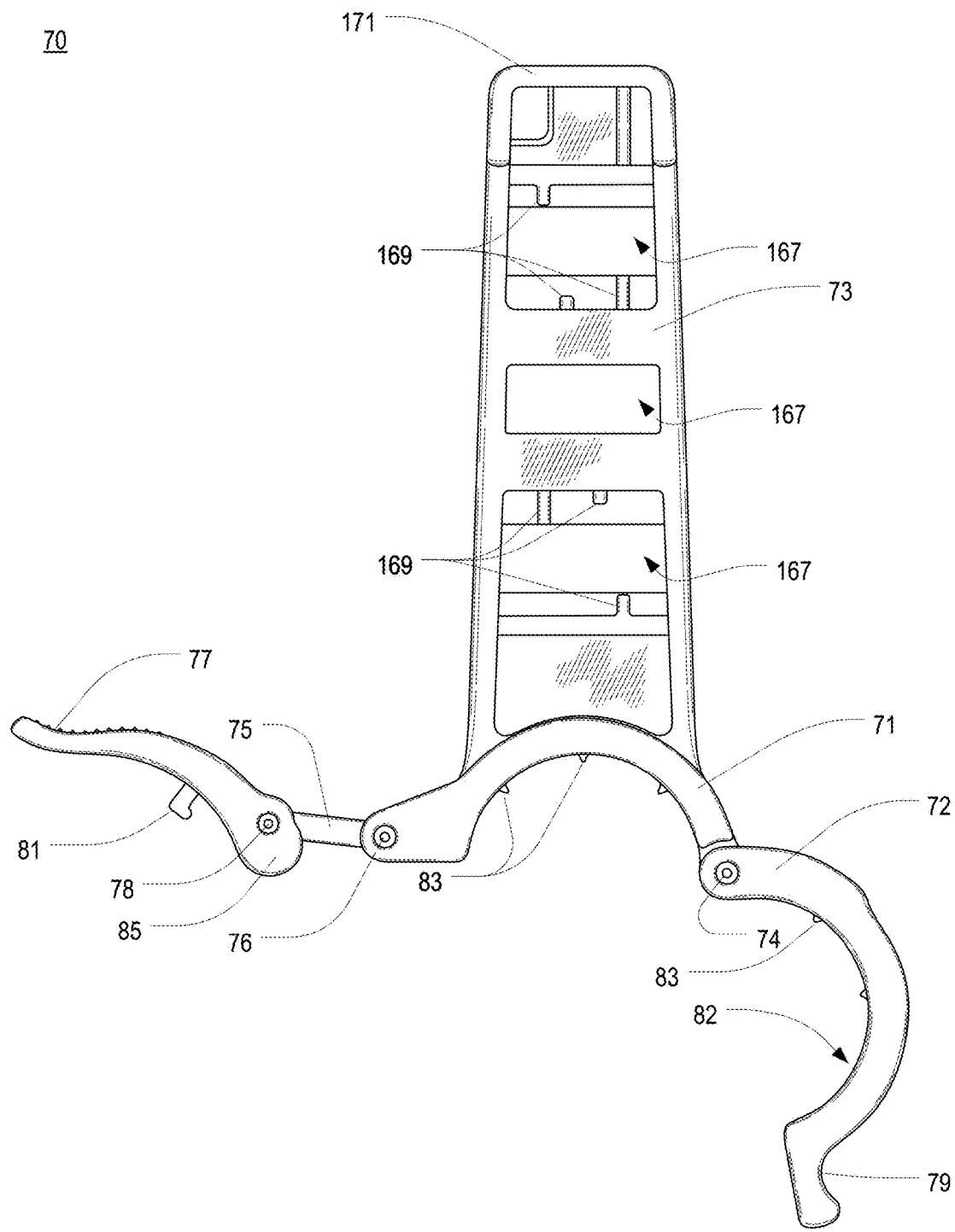

FIGS. 29A and 29B are a top front isometric view and a front elevation view, respectively, of the cable finger accessory 70 of FIG. 2, shown in an open, unclamped state. This accessory 70, which may be particularly suitable as a stable structure to which smaller numbers of cables may be attached in a variety of ways, includes a plurality of semi-arcuate clamp sections 71,72, at least one of which has a finger 73 extending therefrom, that are connected together via a hinge 74 so as to rotate relative to one another. The accessory further includes a clamp mechanism that includes a cam lever link 75 connected to the distal end of one of the clamp sections 71 via another hinge 76, a cam lever 77, including a cam structure 85, connected to the distal end of the cam lever link 75 by a third hinge 78, and a cam trough 79 extending from the distal end of the other clamp section 72. As shown in FIG. 29A, the cam trough 79 preferably includes a notch 84 for receiving the cam lever link 75 as further described below. A latch mechanism, which may for example include a male snap structure 81 on the cam lever 77 and a female snap receptacle 82 on one of the clamp sections 72, is preferably provided to assist in holding the accessory 70 in place. Furthermore, locating ribs or other structures 83 may be provided to help prevent rotation of the accessory 70 when clamped in place. In at least some embodiments, each hinge 74,76,78 used a steel hinge spring pin seated in apertures in the respective structures, but other hinge designs and materials may alternatively be utilized. In at least some embodiments, the other components are all made of injection-molded PC/ABS, but other thermoplastic polymers and other materials may additionally or alternatively be utilized.

Figure 30:
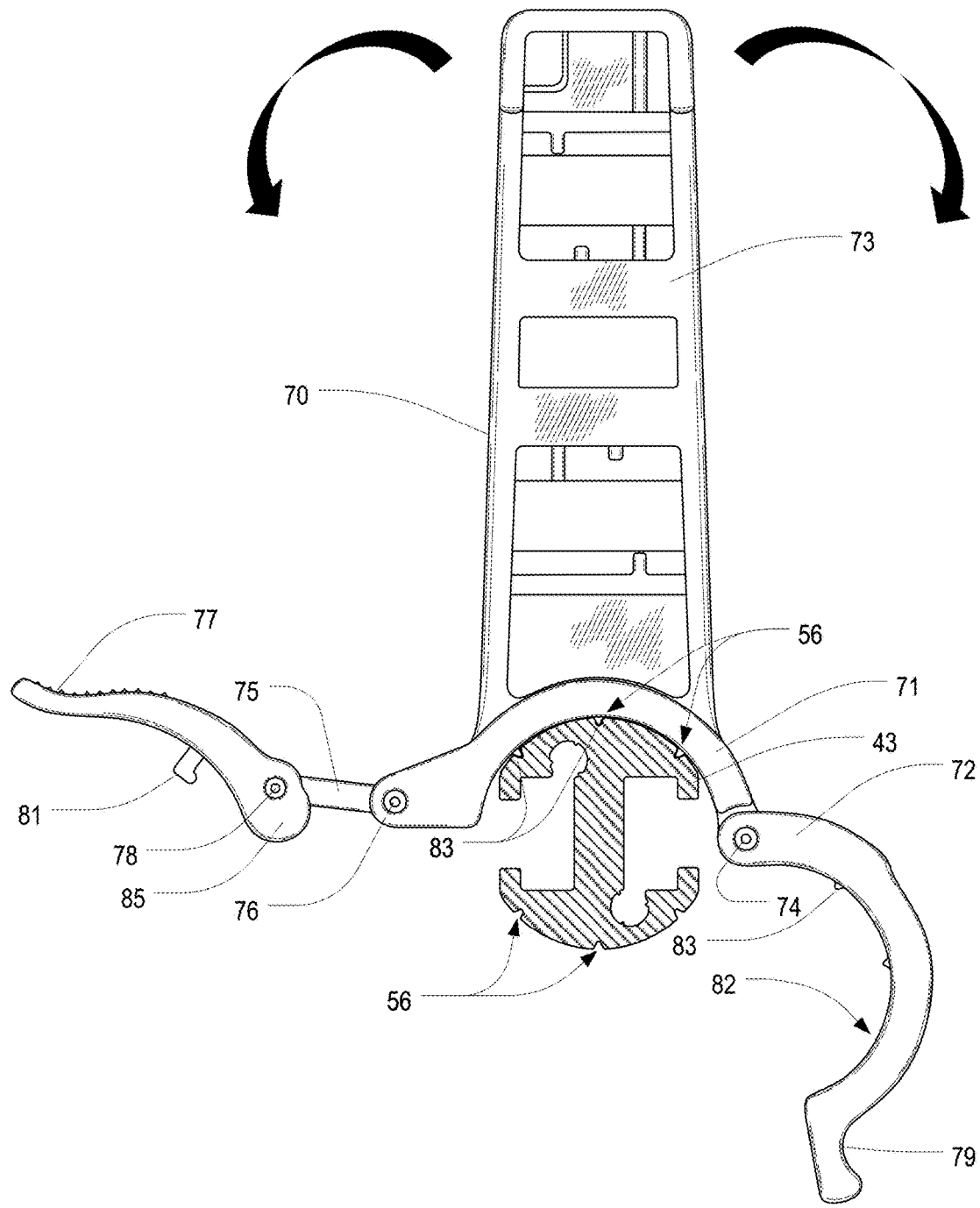
FIGS. 30-33 are front views illustrating the installation of a cable finger accessory on a rod, for example of the accessory rod assembly, which is shown in isolation and in cross-section.
Figure 31:
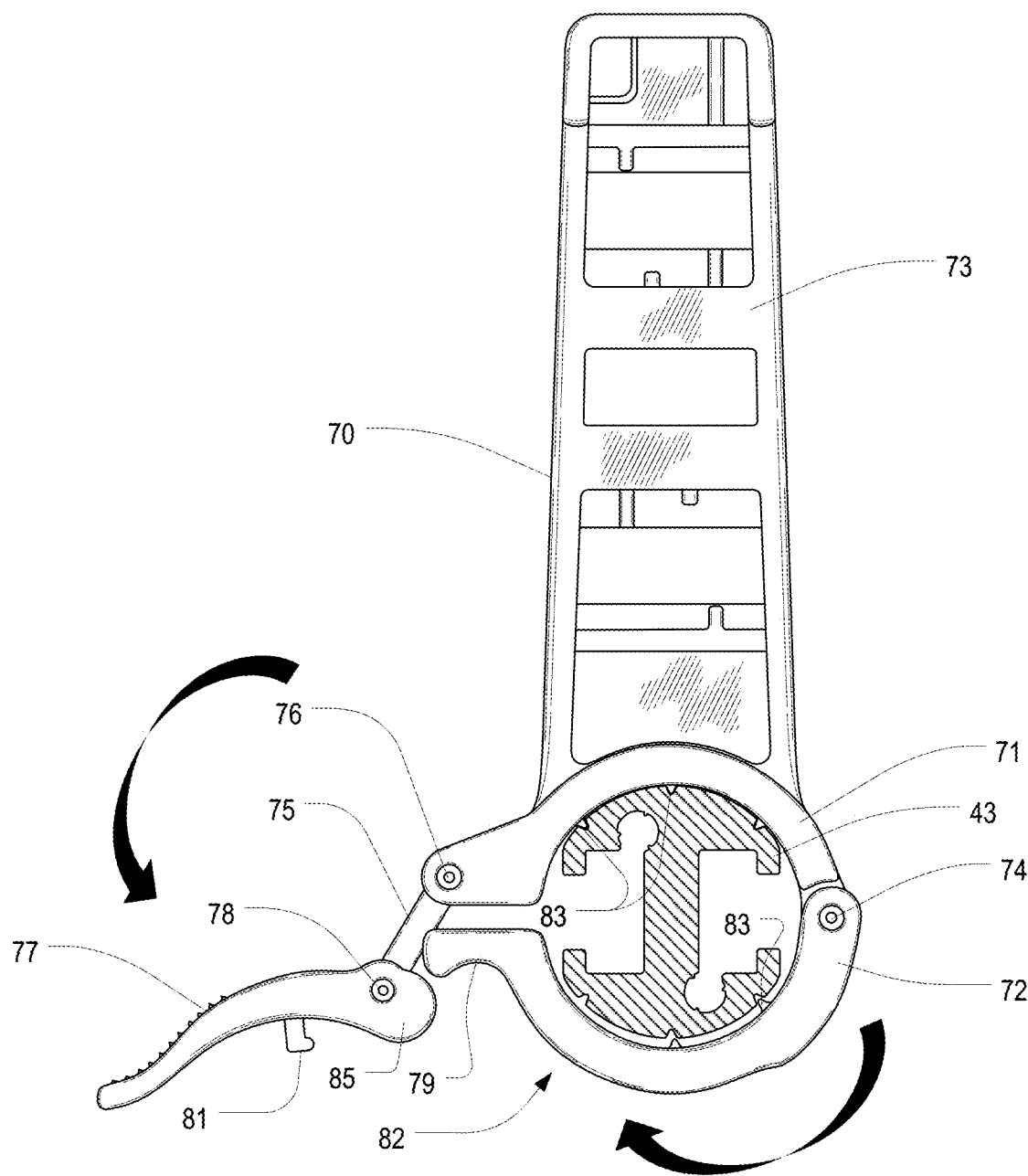
Figure 32:
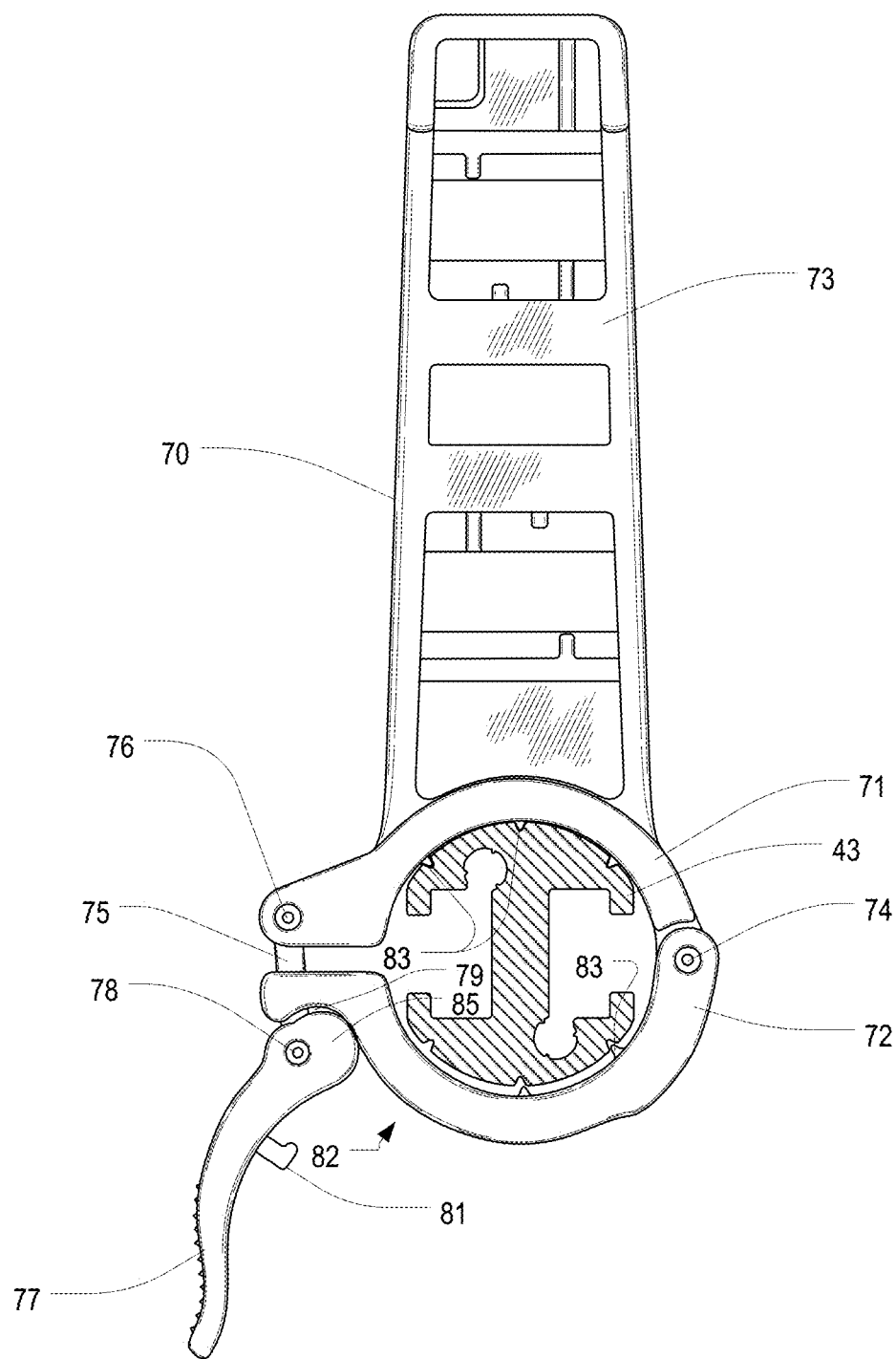
Figure 33:
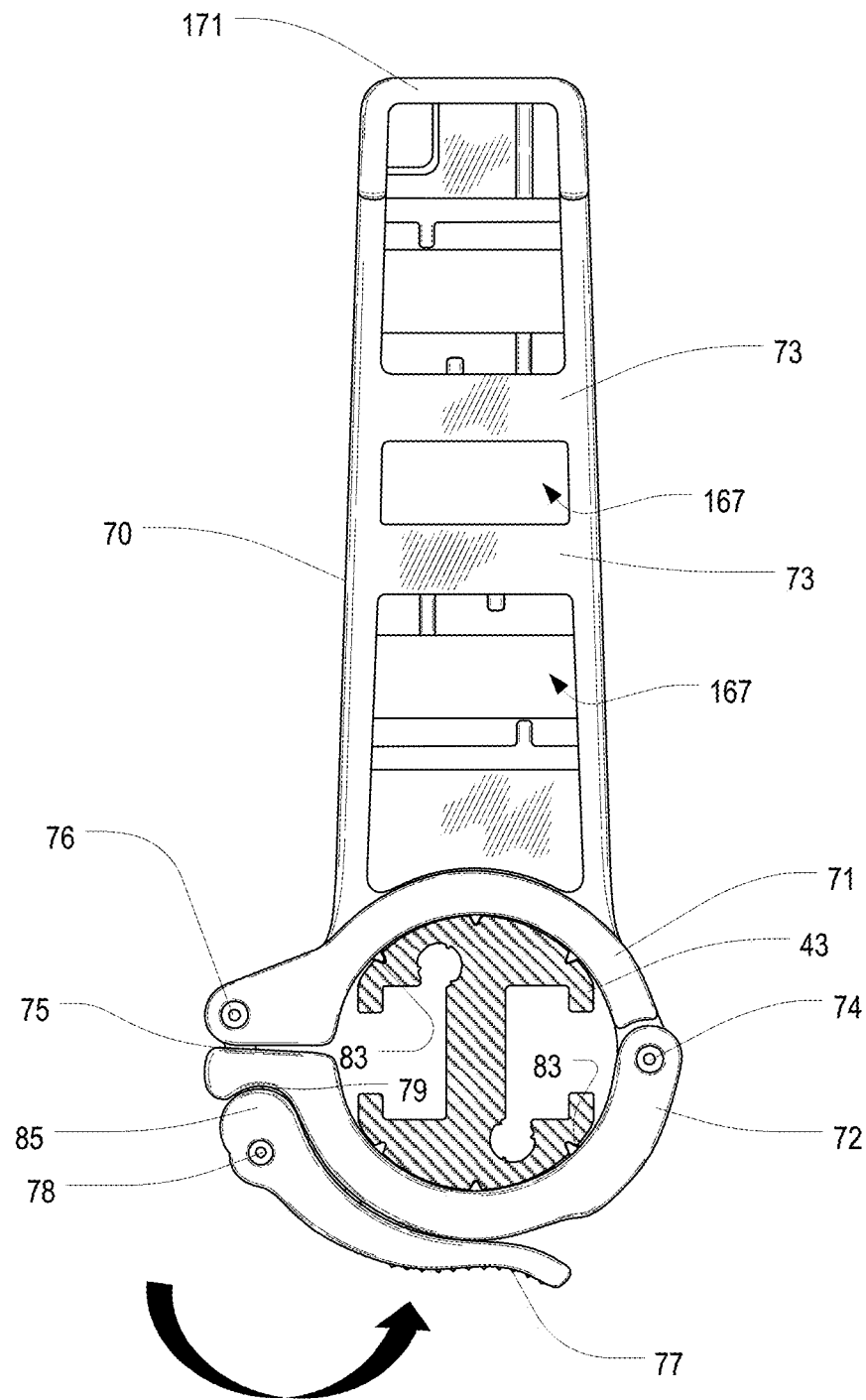

FIGS. 30-33 are front views illustrating the installation of a cable finger accessory 70 on a rod 43, for example of the accessory rod assembly 40, which is shown in isolation and in cross-section. In FIG. 30, the open, unclamped accessory 70 is shown being positioned on the rod 43. As indicated by the arrows, the accessory 70 may be rotated around the rod 43 until the desired orientation is achieved. The ribs 83 on the first clamp 71 are seated in corresponding grip channels 56 in the rod 43. Subsequent or simultaneous with positioning the accessory 70, the second section can be rotated toward the rod 43 (counterclockwise in FIG. 21) and the cam lever 77 and lever link 75 can be rotated in the opposite direction (clockwise in FIG. 21), as indicated by the arrows. As shown in FIG. 32, once the proximal end of the lever 77 is close enough to the cam trough 79 on the second clamp section 72, the lever link 75 fits into the notch 84 in the cam trough 79, the proximal end of the lever 77 is received in the cam trough 79 itself. With the proximal end of the lever 77 seated in the trough 79, the cam lever 77 may be rotated further toward the second clamp section 78, as shown by the arrow in FIG. 33. Rotation of the cam lever 77 causes the cam structure 85 to rotate within the trough 79, thereby causing camming action by the cam 85 against the trough and forcing the second clamp section 78 against the rod 43. As this happens, the male snap structure 81 is forced into the female snap receptacle 82 until it latches into place. When the lever 77 is fully seated against the second clamp section 72, the clamp section will be pressed against the rod 43 with the locating ribs 83 on the clamp section 72 pressed into the corresponding grip channels 56 in the rod 43. In this state, the cable finger accessory 70 is fully clamped on the rod 43, with the cam structure 85 and latch mechanism holding the accessory 70 around the clamp and the locating ribs 83 preventing the accessory 70 from being further rotated unintentionally. The accessory 70 may then be removed or repositioned by releasing the latch mechanism and loosening the cam lever 77 until the accessory 70 can be moved accordingly.

The cable finger 73 includes a plurality of apertures 167. In the illustrated embodiment, apertures 167 are spaced apart along the length of the cable finger 73, and another aperture 167 is disposed at the distal end the cable finger 73. These apertures 167 may be particularly useful as mounting locations. For example, as described in greater detail below, it is contemplated that the cable finger accessory 70 is equipped to accommodate a cable strap/buckle accessory 90 (or another accessory) at multiple positions along the length of the cable finger 73 (at either side thereof) or at the distal end of the cable finger 73. Further control may be provided by an overhang 171 at the distal end of the cable finger 73, which may help prevent cables or groups of cables from becoming inadvertently tangled or removed by sliding off the distal end of the cable finger 73.

Figure 34:
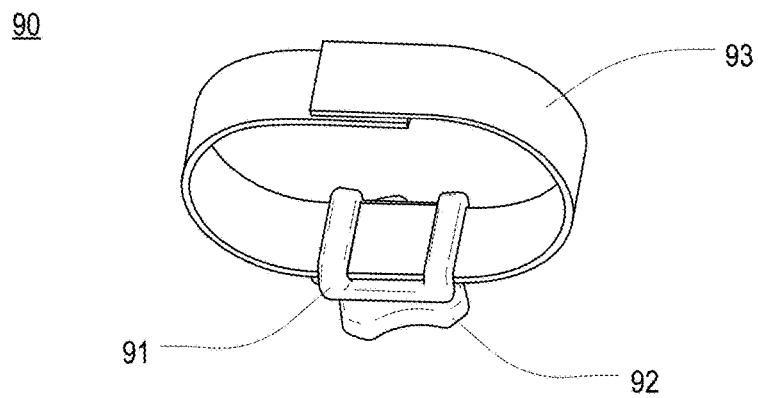
FIG. 34 is a perspective view of the cable strap/buckle accessory of FIG. 2.
Figure 35:
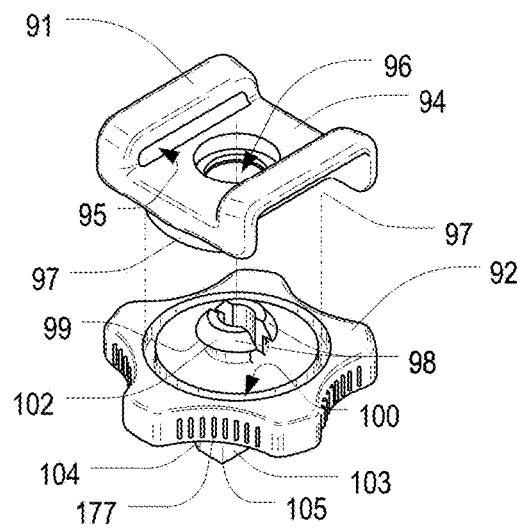
FIG. 35 is an exploded top isometric view of a cable strap/buckle accessory of FIG. 2.
Figure 36:
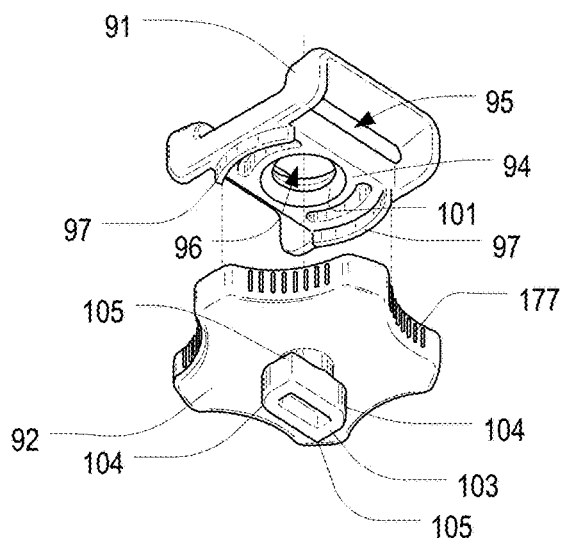
FIG. 36 is an exploded bottom isometric view of a cable strap/buckle accessory of FIG. 2.
Figure 37:
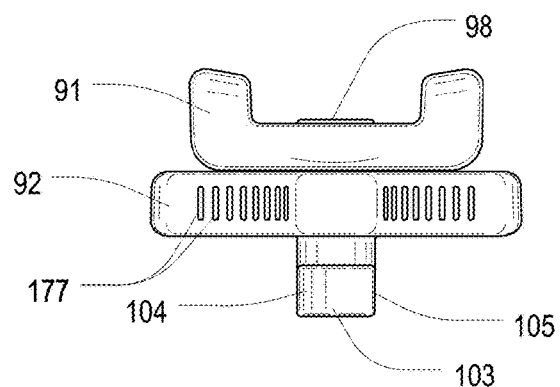
FIG. 37 is an elevation view of a cable strap/buckle accessory of FIG. 2.

FIG. 34 is a perspective view of the cable strap/buckle accessory 90 of FIG. 2. This accessory 90, which may be particularly suitable as a flexibly-located, quickly-installed structure for holding bundles of cables, includes a buckle 91, a buckle support 92, and a strap 93. The strap 93 may be any conventional strap, such as a hook-and-loop (e.g., Velcro®) strap, zip tie, or the like. FIGS. 35-37 are an exploded top isometric view, an exploded bottom isometric view, and an elevation view, respectively, of a cable strap/buckle accessory 90 of FIG. 2. As shown therein, the buckle 91 includes a base 94 and two raised slots 95. The base 94 is penetrated by a round socket 96, and two coaxial arcuate bosses 97 extend from the bottom of the base 94. The buckle support 92 includes a mounting boss 103 (described below), and a round, resilient snap 98, which is preferably a split snap, that corresponds in size to the socket 96 of the buckle 91. The snap 98 may be snapped or latched into the socket 96 by aligning them and applying sufficient force to deflect the split snap sections inward an amount sufficient to let them pass through the socket 96. Angled surfaces 102 on the top of the snap 98 and similarly-angled surfaces 101 on the underside of the buckle base 94 make this easier. Once the snap 98 penetrates the socket 96 sufficiently, ledges 99 on the underside of the snap sections 98 retain the snap in place. Ridges 177 arranged along side edges of the buckle support 92 provide a surface that is easier to grip or manipulate during installation or use. FIG. 37 is a side elevation view of the buckle 91 and buckle support 92 of FIGS. 34-36, shown in an assembled state.

Figure 38A:
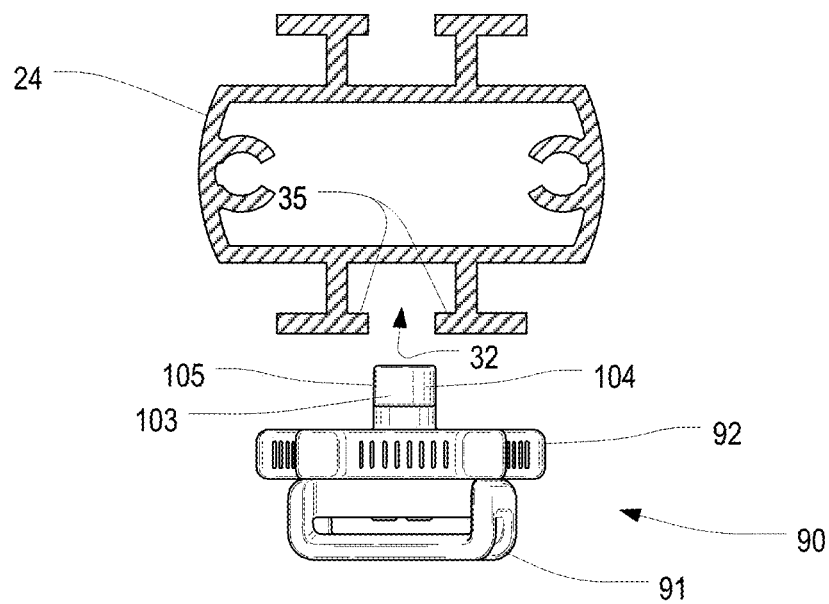
FIGS. 38A and 38B are top views illustrating the installation of a cable strap/buckle accessory on the spine member of FIG. 2, which is shown in isolation and in cross-section.
Figure 38B:
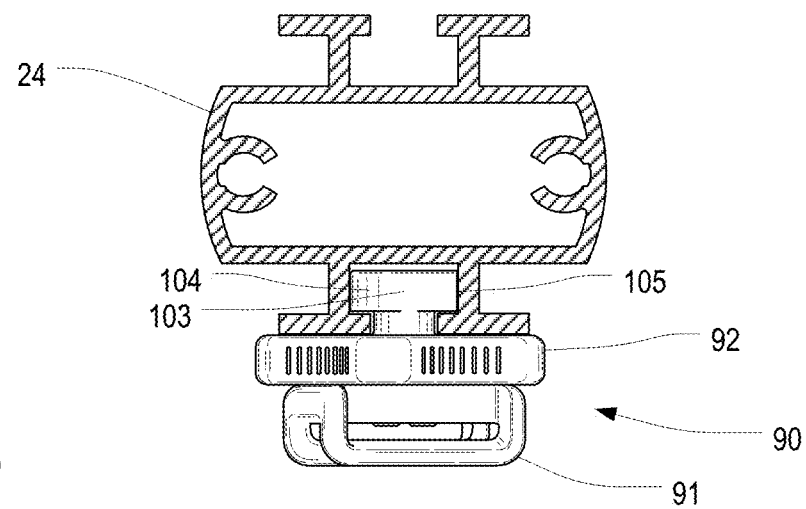

The accessory 90 may be installed in any of a variety of locations in the cable manager 10 or other location. For example, FIGS. 38A and 38B are top views illustrating the installation of a cable strap/buckle accessory 90 on the spine member 24 of FIG. 2, which is shown in isolation and in cross-section. As perhaps best shown in FIG. 36, the mounting boss 103 is a four-sided rectangular structure with two round corners 104 and two generally square, or right-angle, corners 105. When oriented with the narrow portion of the rectangular mounting boss 103 along the T-slot channel 32 in the spine member 24, the mounting boss 103 may be inserted into the channel 32 (or into a similar structure in a lateral member 23 or other member, or into other channels, openings, or the like), as shown in FIG. 38A. Once inserted, the buckle support 92 may be rotated approximately 90 degrees, preferably in a clockwise direction, such that the wide portion of the rectangular mounting boss 103 is held in place (blocked from removal) by the ledges 35 of the channels 32, as shown in FIG. 38B. Such rotation and subsequent "locking in place" is facilitated by the round corners 104 (which make it easy to turn the buckle support 92 in the preferred direction) and the square corners 105 prevent further rotation and help hold the mounting boss 103 in place. The accessory 90 may then be removed by reversing the direction of rotation of the buckle support 92 in the opposite direction. The round corners 104 of the mounting boss 103 permit such rotation to occur, and when the narrow portion of the mounting boss 103 is once again aligned with the opening of the channel 32, the accessory can be removed.

Figure 39:
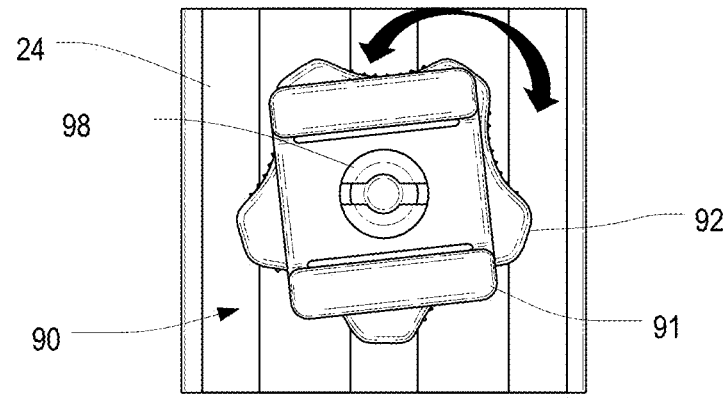
FIG. 39 is a fragmentary front view of the accessory and spine member of FIG. 38B.

It will also be appreciated that the round snap 98 and socket 96, as well as coaxial arcuate bosses 97 and trough or slot 100, allow rotation of the buckle 91 relative to the buckle support 92. In some embodiments such rotation can occur whether the buckle support 92 is installed, while in some embodiments, such rotation can occur only when it is installed, and in some embodiments such rotation can occur only when it is not installed. Rotation is possible because the arcuate bosses 97 are coaxial with the socket 96, and the trough or slot 100 is coaxial with the snap 98, such that latching the snap and socket together also causes the arcuate bosses 97 to be located in the trough or slot 100. Once assembled into the state shown in FIG. 37, the buckle 91 may be rotated relative to the buckle support 92 by rotating the buckle base 94 around the snap 98 as the arcuate bosses 97 move within the circular trough or slot 100. An example of such rotation is shown in FIG. 39, which is a fragmentary front view of the accessory 90 and spine member 24 of FIG. 38B. As indicated by the arrow, the buckle 91 may be rotated either clockwise or counterclockwise about the snap 98 of the buckle support 92.

Figure 40A:
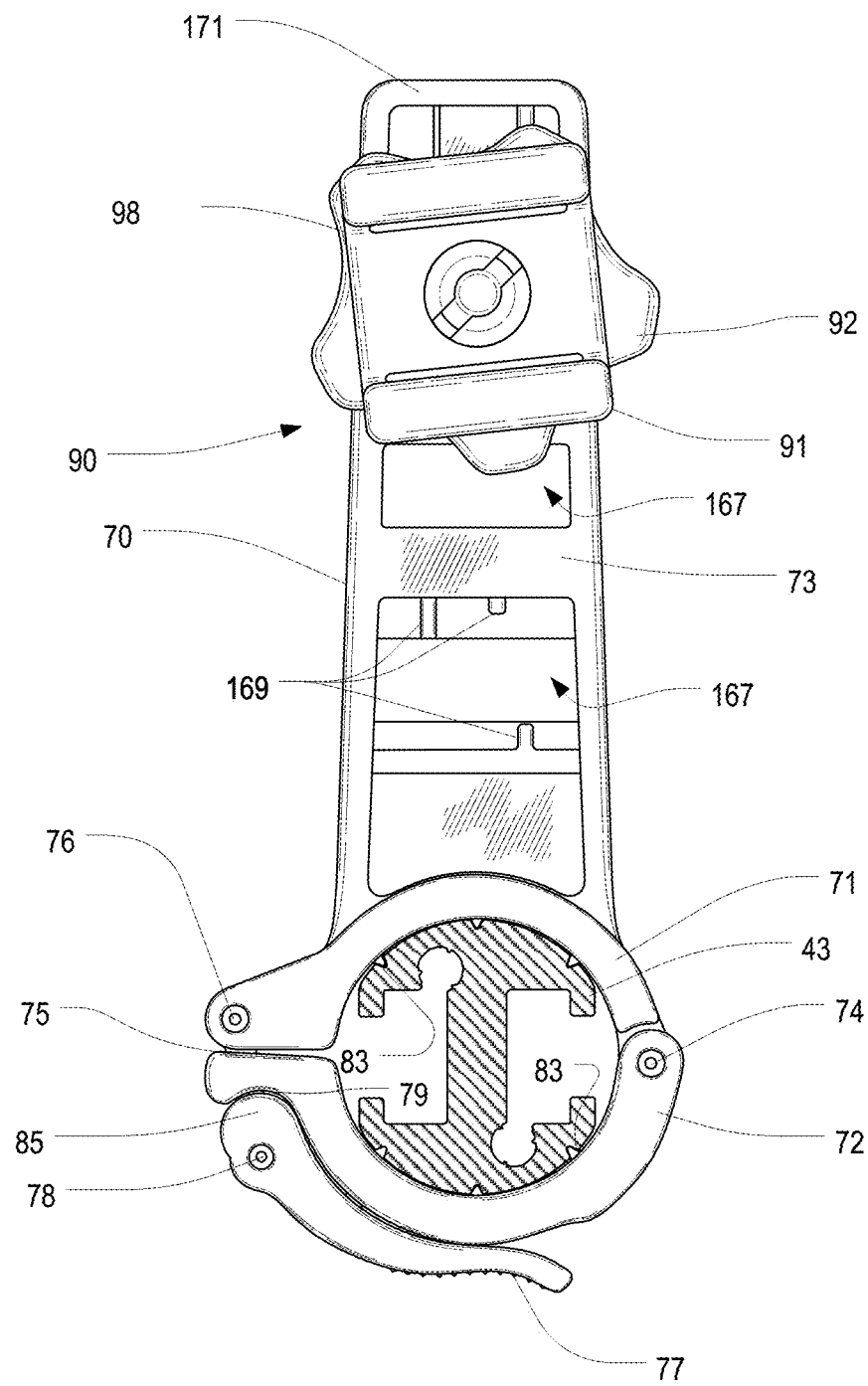
FIGS. 40A and 40B are front views of a cable strap/buckle accessory being mounted on the cable finger accessory and rod of FIG. 33.
Figure 40B:
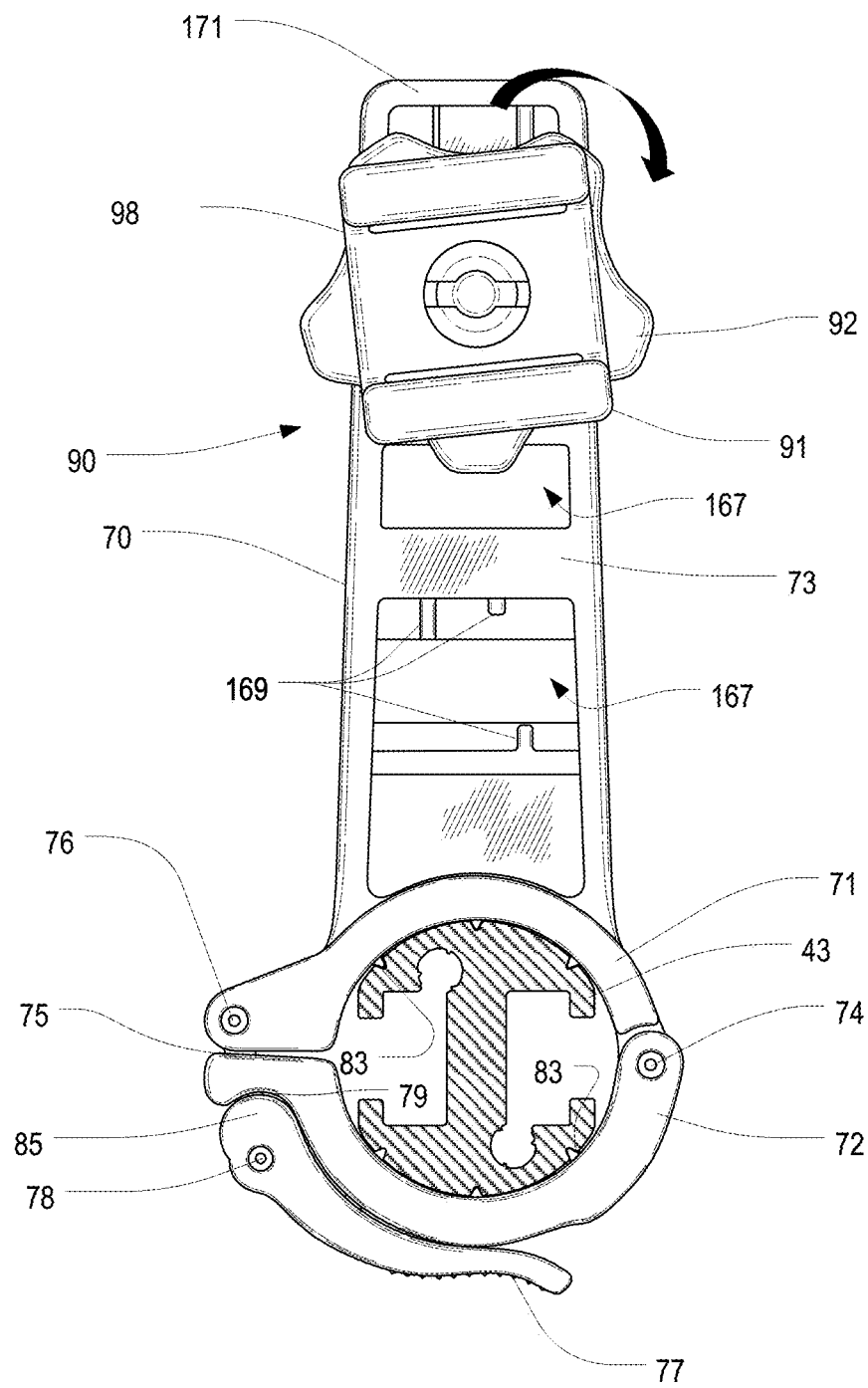

The accessory 90 may also be installed and used in a variety of different locations on the cable finger accessory 70 of FIGS. 29A-33. For example, FIGS. 40A and 40B are front views of a cable strap/buckle accessory 90 being mounted on the cable finger accessory 70 and rod 43 of FIG. 33. As noted previously, the cable finger 73 includes a plurality of apertures 167 spaced apart along the length of the cable finger 73, and another aperture 167 disposed at the distal end the cable finger 73. Each of the apertures 167 can be used to secure a cable strap/buckle accessory 90 to the cable finger accessory 70. Depending on the position and spacing of the apertures 167, some or all of the apertures 167 may be used at once. The apertures 167 are depicted as generally rectangular-shaped apertures, but other shapes are likewise contemplated. In at least some embodiments, a set of locating ribs 169 is disposed adjacent each aperture on one side of the cable finger 73 or the other; these ribs 169 can be used to align a fastener or some other mounting structure in order to facilitate securement of a separate cable strap/buckle accessory 90 to the cable finger accessory 70. In some embodiments, such ribs 169 are provided on both sides (front and rear) of the cable finger 73; in other embodiments, no ribs are provided at all. In at least some embodiments, a cable strap/buckle accessory 90 may be installed on either side of each aperture 167 based on the preference of the user, each aperture 167 may be used only from one side or the other.

When installed on a cable finger accessory 70, the cable strap/buckle accessory 90 makes it easier to retain and manage bundles of cables. In particular, when oriented properly, the mounting boss 103 of the buckle support 92 can be received within one of the apertures 167 of the cable finger 73, as shown in FIG. 40A. Once received within an aperture 167, the mounting boss 103 is rotatable in one direction (preferably clockwise), as shown in FIG. 40B, so that the boss 103 is seated between locating ribs 169 at either side thereof, thereby providing a fixed position for the boss 103 between the ribs 169 and also frictionally clamping the boss 103 and buckle support 92 around the cable finger 73. Removal of the cable strap/buckle accessory 90 can be accomplished by reversing the process so that the mounting boss 103 is aligned with the shape of the aperture 167 to permit it to be removed therefrom. As can be seen in FIG. 29A, apertures 167 are spaced apart along the length of the cable finger 73, and another aperture 167 is disposed at the distal end the cable finger 73. In this regard, it is contemplated that the cable finger accessory 70 is equipped to accommodate a cable strap/buckle accessory 90 (or another accessory) at multiple positions along the length of the cable finger 73 (at either side thereof) or at the distal end of the cable finger 73.

Figure 41:
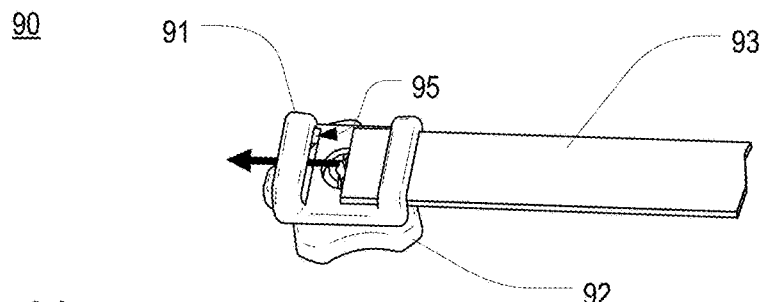
FIGS. 41-43 are perspective views of the cable strap/buckle accessory of FIG. 34 illustrating the attachment of the strap to the buckle.
Figure 42:
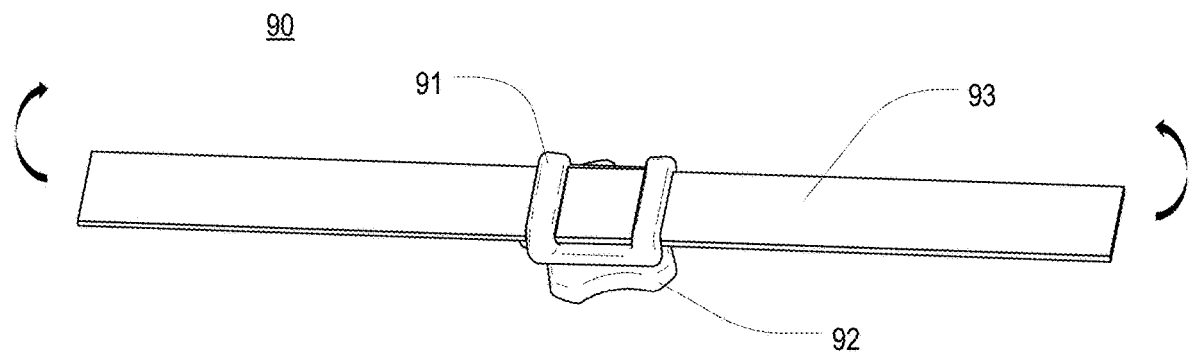
Figure 43:
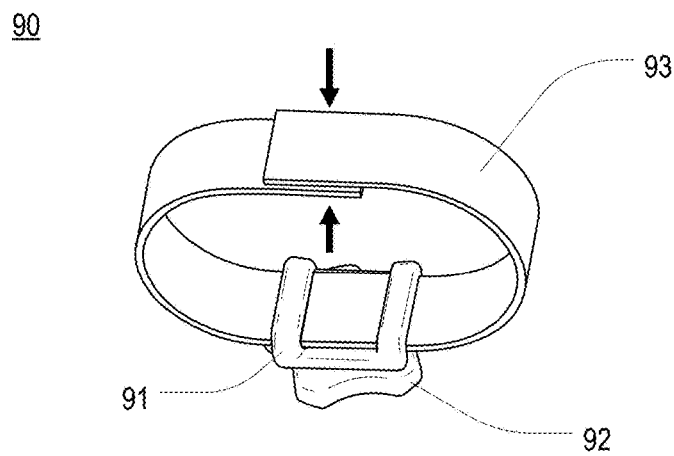

FIGS. 41-43 are perspective views of the cable strap/buckle accessory 90 of FIG. 34 illustrating the attachment of the strap 93 to the buckle 91. As shown in FIG. 41, an end of the strap 93 may be inserted through the two raised slots 95. Once the strap 93 is fully inserted through the slots 95 and positioned as desired, as shown in FIG. 42, the ends may be pulled up, out, back, or the like and closed together, as shown in FIG. 43. Hook-and-loop fasteners or the like may be provided to facilitate the strap ends being fastened together, or other devices may be utilized. Such a strap 93 is very useful for holding a bundle of cables together.

Figure 44:
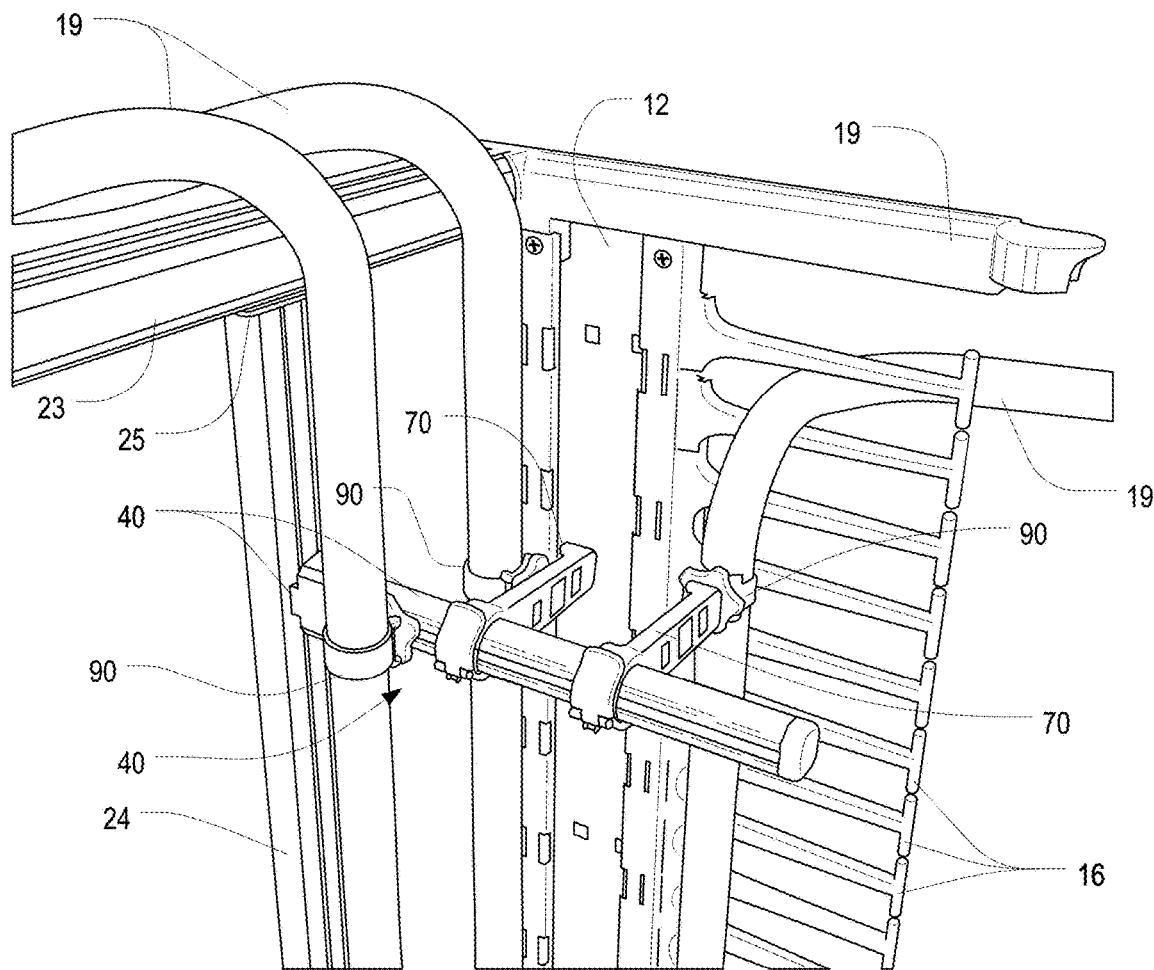
FIG. 44 is a fragmentary perspective view of an upper corner of a cable manager like that shown in FIG. 2 but with various accessories and cable bundles installed therein.

FIG. 44 is a fragmentary perspective view of an upper corner of a cable manager 10 like that shown in FIG. 2 but with various accessories and cable bundles 19 installed therein. The accessories include an accessory rod assembly 40, two cable finger accessories 70, and three cable strap/buckle accessories 90.

Advantageously, various embodiments of the cable manager design of the present invention use a series of extrusions to allow toolless installation, adjustment and removal of cable manager accessories. Accessories can be "infinitely" adjusted along the extrusions so they can reach a much larger portion of the space in and around the manager. The extrusions themselves can also be adjusted within the manager to any desired location. The invention includes several different accessories that may be toollessly installed, adjusted, and removed and corresponding methods with which they may be used. The toolless installation of these accessories improves usability and makes installation, adjustment and removal much faster and easier.

Figure 45:
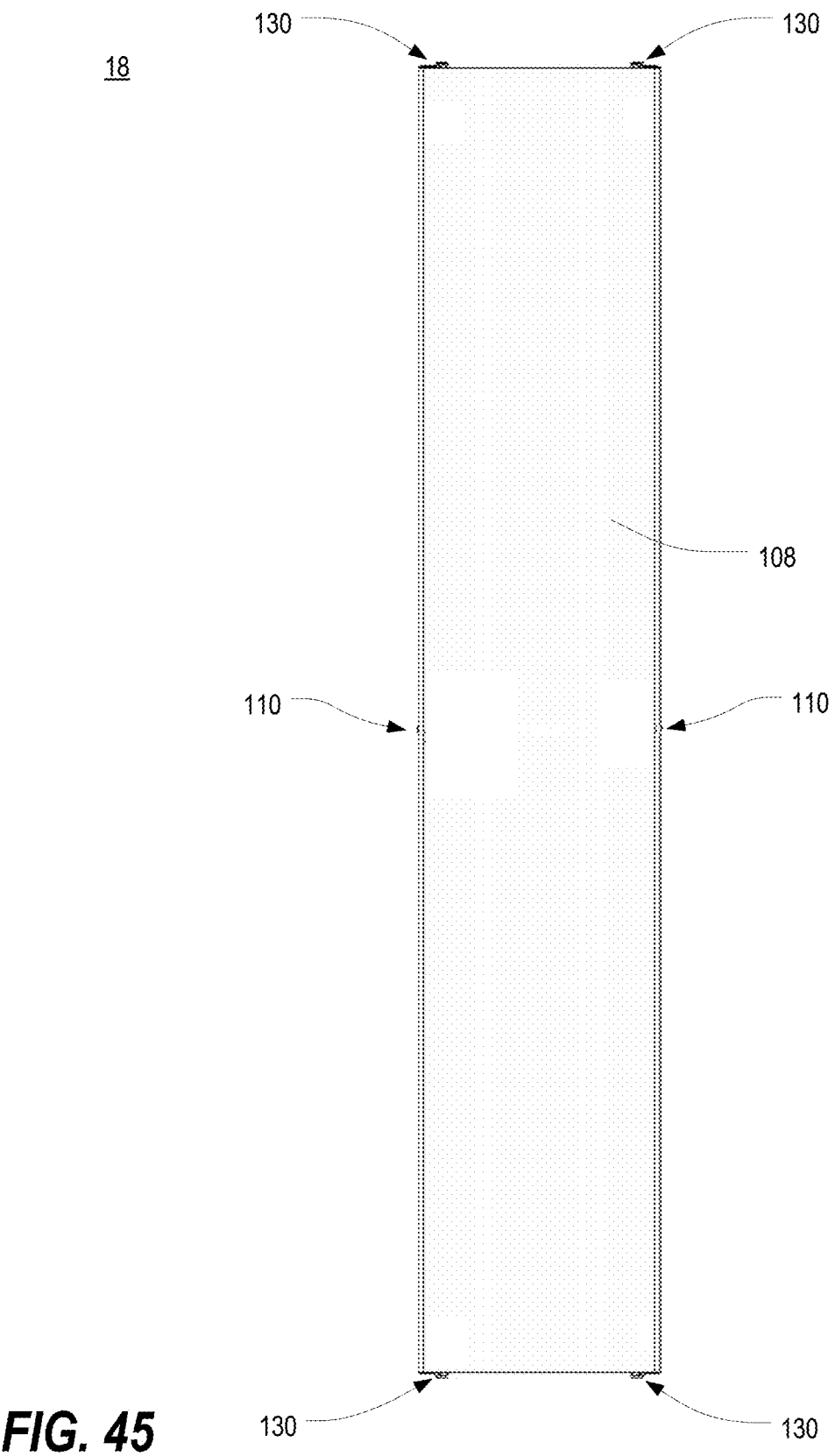
FIG. 45 is a front elevation view of the door assembly of FIG. 1.
Figure 46:
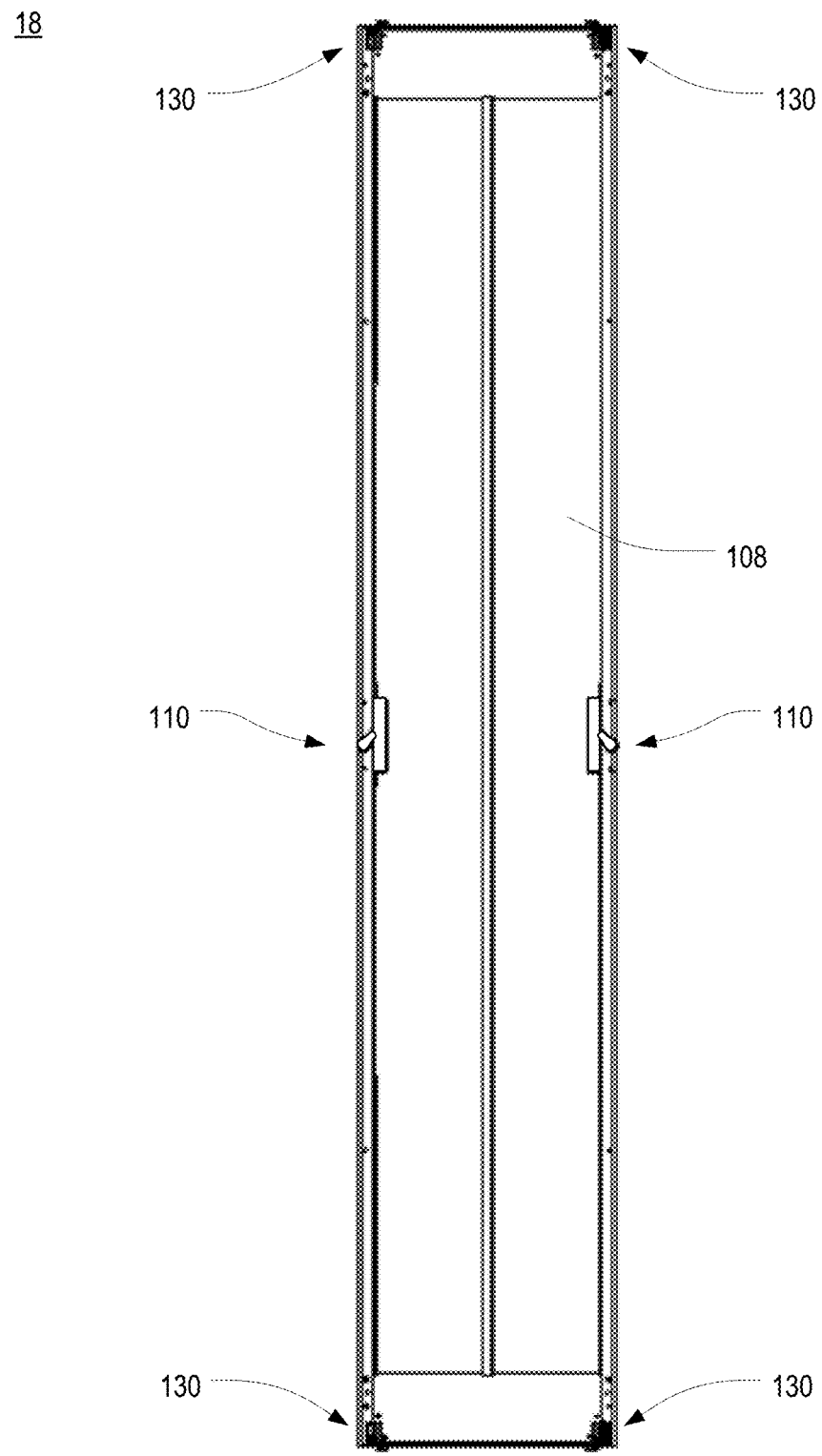
FIG. 46 is a rear elevation view of the door assembly of FIG. 1.
Figure 47:
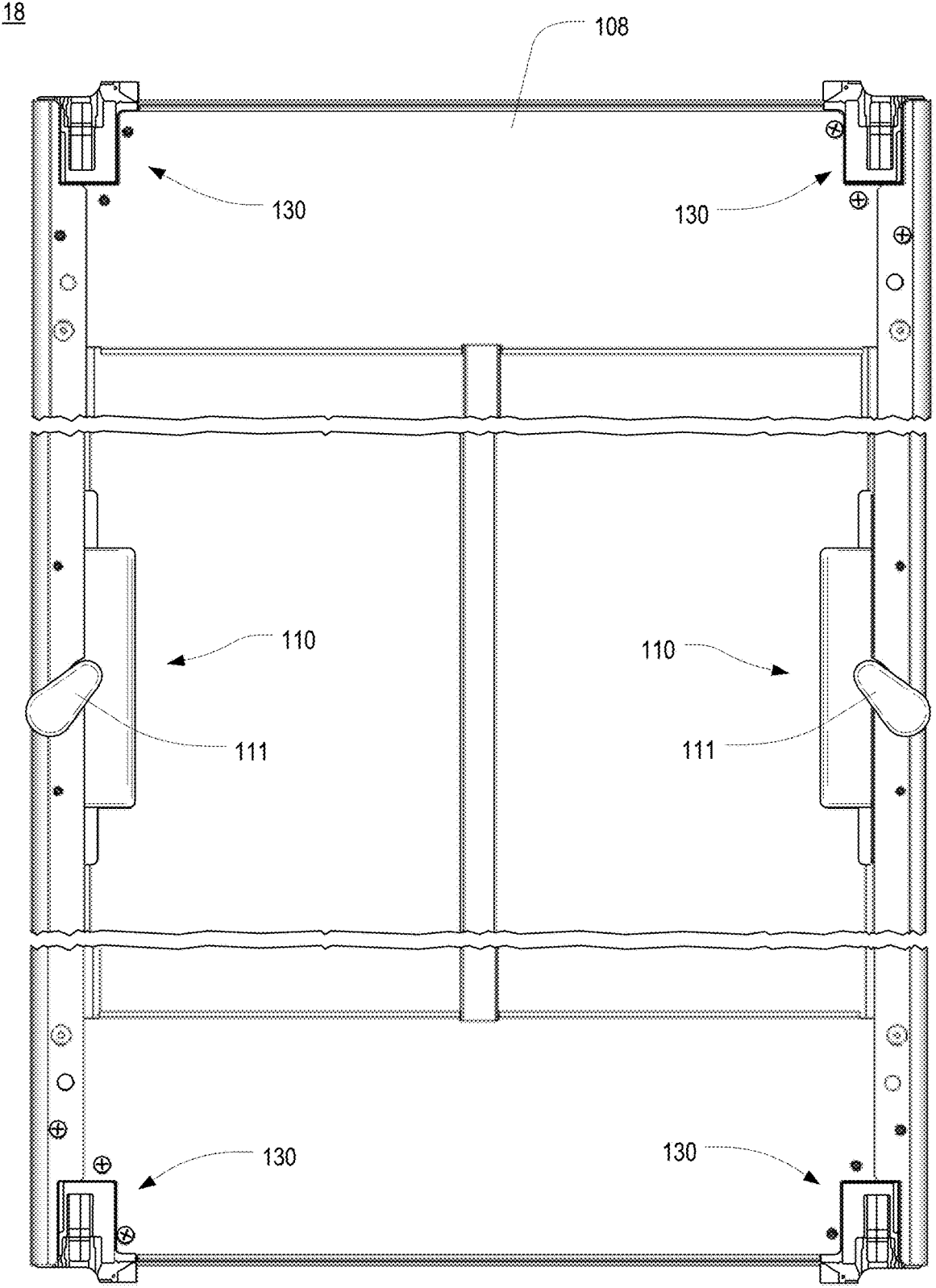
FIG. 47 is an enlarged fragmentary rear elevation view of the door assembly of FIG. 1.

Referring back to FIG. 1, the cable manager 10 includes, in at least some embodiments, a door assembly 18. FIGS. 45-47 are a front elevation view, a rear elevation view, and an enlarged fragmentary rear elevation view, respectively, of the door assembly 18 of FIG. 1. As shown therein, the door assembly 18 includes a door panel 108 having a hinge set along each side and a corresponding latch assembly 110 for each hinge set. As used herein, the term "door panel" refers generally to the portion of the door assembly 18 that swings back and forth relative to the hinges, and may include a plurality of individual panels as well as a variety of other structure. Each hinge set includes a top and bottom hinge assembly 130 that is operationally connected to a respective latch assembly 110. Because each side of the door panel 108 includes its own hinge set and latch assembly 110, the door assembly 18 may be hinged open from either side, and/or the door panel 108 may be removed completely, as shown in FIG. 2. Although shown as part of the cable manager 10, it will be appreciated that the latch assemblies 110 and hinge sets could be used on other cable managers and/or on any variation of electronic equipment (IT) cabinet or enclosure, or at least some other applications, where it is desired to have a door that hinges opens from either side.

Figure 48:
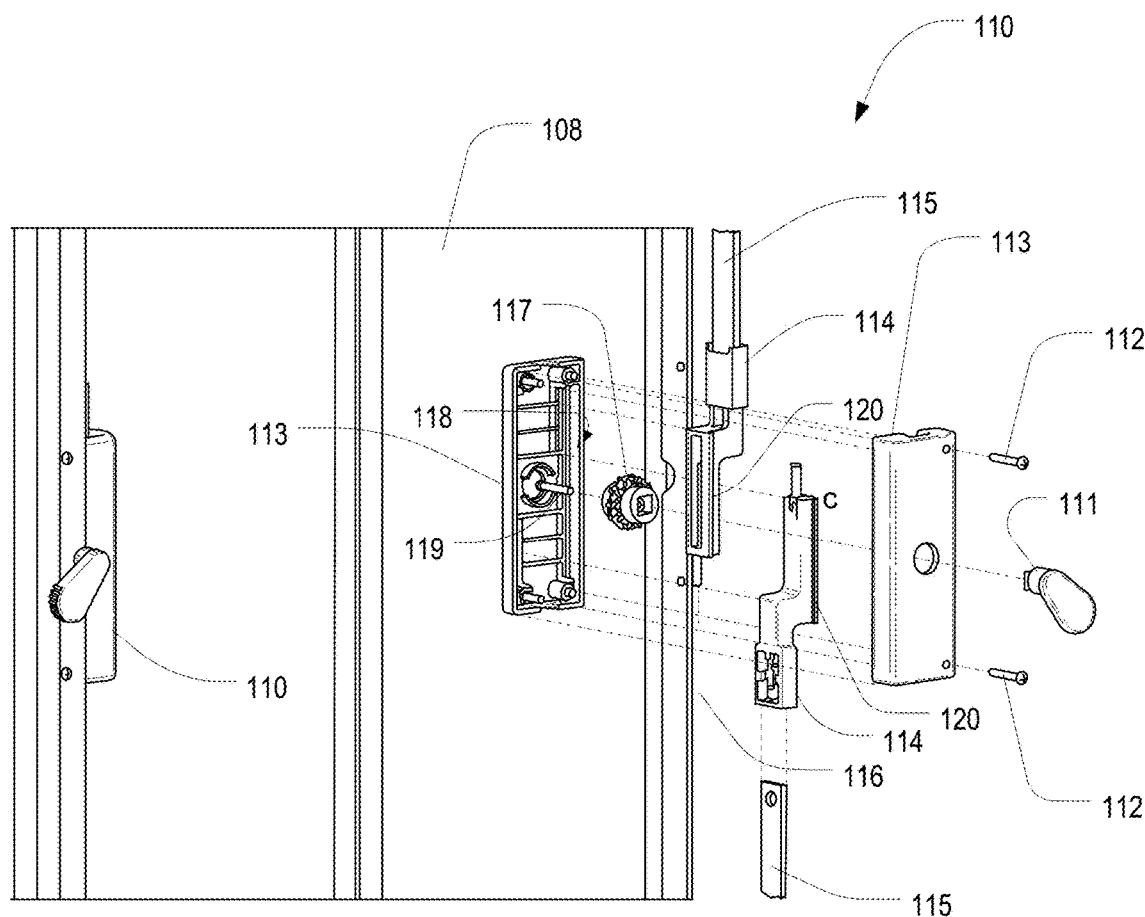
FIG. 48 is a fragmentary, partially exploded, orthogonal view of portions of the door panel and latch assemblies of FIGS. 45-47.
Figure 49:
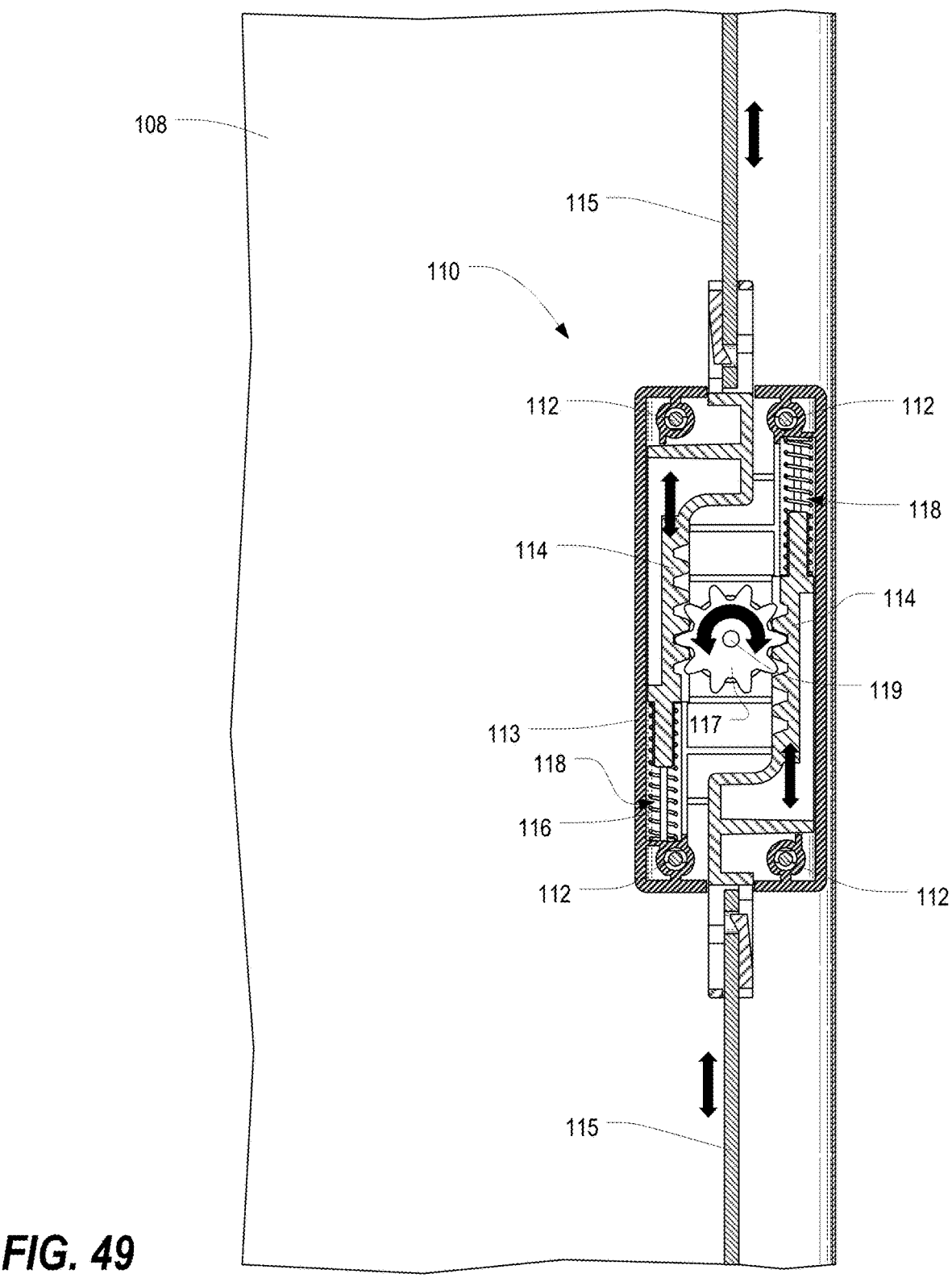
FIG. 49 is a fragmentary, rear cross-sectional view of portions of the door panel and latch assemblies of FIGS. 45-47.

FIGS. 48 and 49 are a fragmentary, partially exploded, orthogonal view and a fragmentary, rear cross-sectional view, respectively, of portions of the door panel 108 and latch assemblies 110 of FIGS. 45-47. As shown therein, each latch assembly 110 includes a latch handle 111, a pair of racks 114, a pair of lock rods 115, a pair of compression springs 116, and a gear 117, all contained in a latch housing 113. The latch housing 113 preferably includes two substantially identical halves that are held together with assembly screws 112. The handle 111 is connected to the gear 117 by an assembly screw or other axle 119. The racks 114, which include an upper rack and a lower rack, are disposed on either side of the gear 117 such that the teeth of each rack mesh with the teeth of the gear 117. Rotation of the gear 117 is thus linked to upward and downward movement of the racks 114. To facilitate movement, each rack 114 includes lengthwise ears 120 that ride in tracks 118 formed in both halves of the housing 113. A compression spring 116 is disposed at the proximal end of at least one of the racks 114, while the distal end of each rack 114 is attached to a proximal end of a respective lock rod 115. In operation, movement of the handle 111 turns the gear 117, which in turn effectuates upward and downward movement of the racks 114 in their tracks 118, thereby moving the lock rods 115 up and down.

In at least some embodiments, the door panel 108 and frame are made of sheet metal and steel tube, but other designs and materials may alternatively be utilized. In at least some embodiments, the lock rods 115 are made of aluminum, but other designs and materials may alternatively be utilized. In at least some embodiments, the screws 112,119 and springs 116 are made of steel, but other designs and materials may alternatively be utilized. In at least some embodiments, the other components are all made of injection-molded PC/ABS, but other thermoplastic polymers and other materials may additionally or alternatively be utilized.

Figure 50:
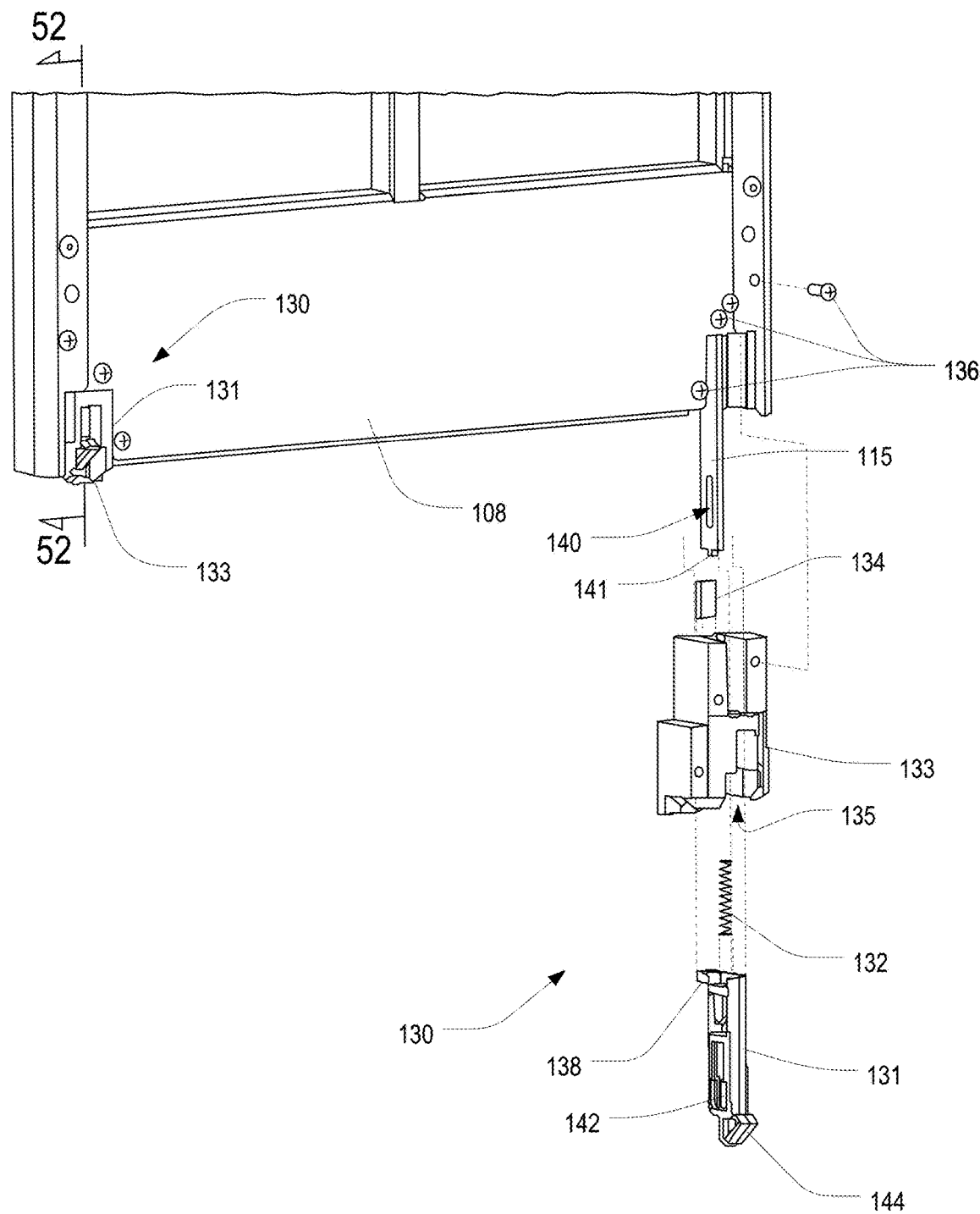
FIG. 50 is a fragmentary, partially exploded, orthogonal view of portions of the door panel and the lower hinge assemblies of FIGS. 45-47.
Figure 51:
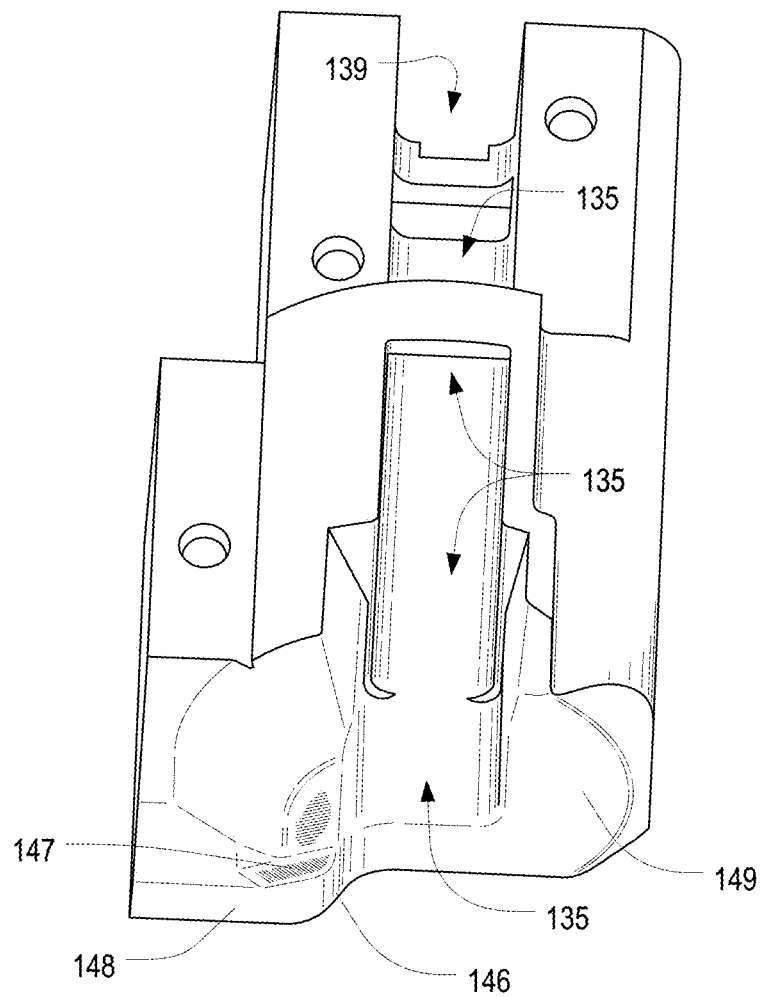
FIG. 51 is a bottom orthogonal view of the lower right hinge body of FIG. 50.
Figure 52:
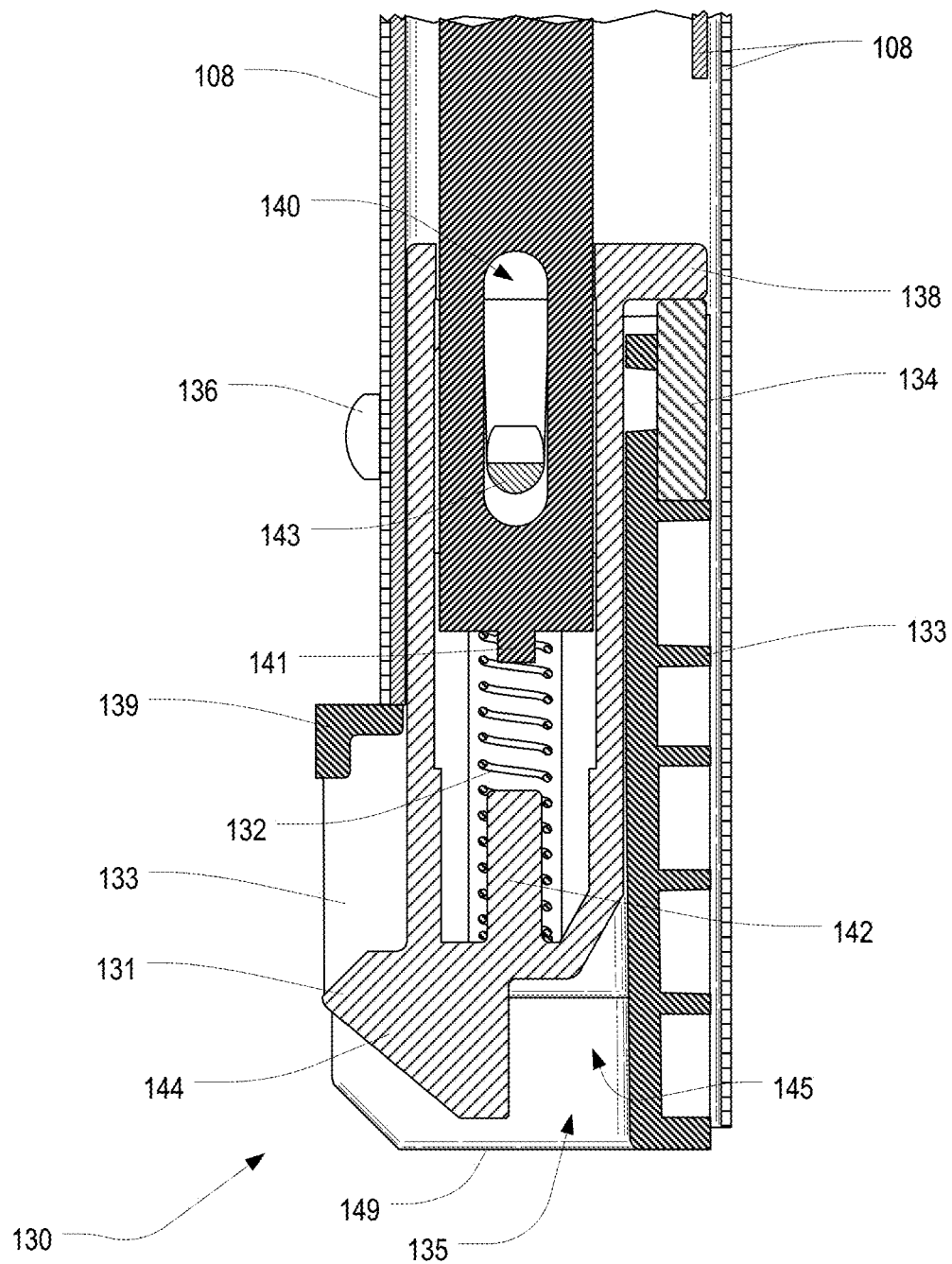
FIG. 52 is a side cross-sectional view of portions of the door panel and one of the lower hinge assemblies of FIG. 50, taken along line 52-52.

FIG. 50 is a fragmentary, partially exploded, orthogonal view of portions of the door panel 108 and the lower hinge assemblies 130 of FIGS. 45-47. Each hinge assembly 130 includes a hinge body 133 that carries a bolt 131 in a central cavity 135. FIG. 51 is a bottom orthogonal view of the lower right hinge body 133 of FIG. 50, and FIG. 52 is a side cross-sectional view of portions of the door panel 108 and one of the lower hinge assemblies 130 of FIG. 50, taken along line 52-52. (It will be appreciated that the hinge body 133 in the lower left-hand corner of FIG. 50 is a mirror image of the hinge body 133 in the lower right-hand corner, and that some of the other components of each hinge assembly 130 are likewise left- or right-handed.) At its proximal end, the bolt 131 receives the distal end of one of the lock rods 115, while at its distal end, the bolt 131 extends out of the opposite end of the hinge body 133. As shown in FIG. 52, the bolt 131 includes an internal pin 143 that extends laterally through a slot 140 in the lock rod 115 such that the lock rod 115 is free to move longitudinally, relative to the bolt 131, over the length of the slot 140. The bolt 131 is biased away from the end of the lock rod 115 by a compression spring 132 disposed between a boss or other structure 141 on the end of the lock rod 115 and another internal pin 142 that extends vertically within the bolt 131.

As perhaps best shown in FIG. 50, the hinge body 133 is fastened to the door panel 108 with assembly screws 136. With particular reference to the arrangement shown in FIG. 52, the bolt 131 has vertical freedom of movement, relative to the hinge body 133, but its downward movement is limited by the interface between a tab 138 at the proximal end of the bolt 131 (the top of the bolt 131 in FIGS. 50 and 52) and the proximal end of the hinge body 133 (the top of the hinge body 133 in FIGS. 50-52), and its upward movement is limited by the interface between the bolt strike 144 and another portion 139 of the hinge body 133. Contact between the bolt tab 138 and the hinge body 133 may be cushioned by a bumper 134 of neoprene or other material in order to reduce noise, physical damage to the parts, and/or the like. Contact between the bolt strike 144 and the hinge body 133 is naturally cushioned by the compression spring 132, but a bumper (not shown) may be utilized here as well. Notably, when the bolt 131 is fully extended as shown in FIG. 52, a hinge pin cavity 145 is defined behind the bolt strike 144, within the end of the central cavity 135 of the hinge body 133.

Figure 53:
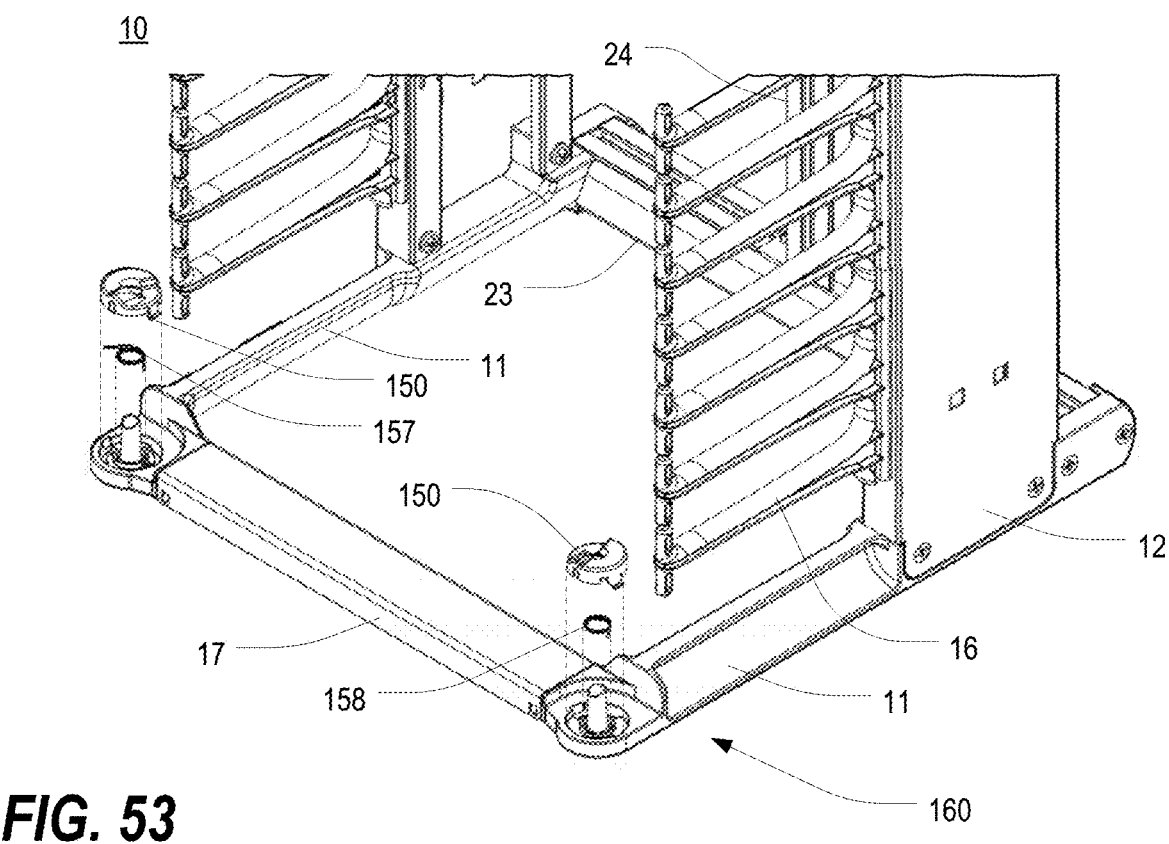
FIG. 53 is a fragmentary, partially-exploded, isometric view of the lower portion of the cable manager of FIG. 2.
Figure 54:
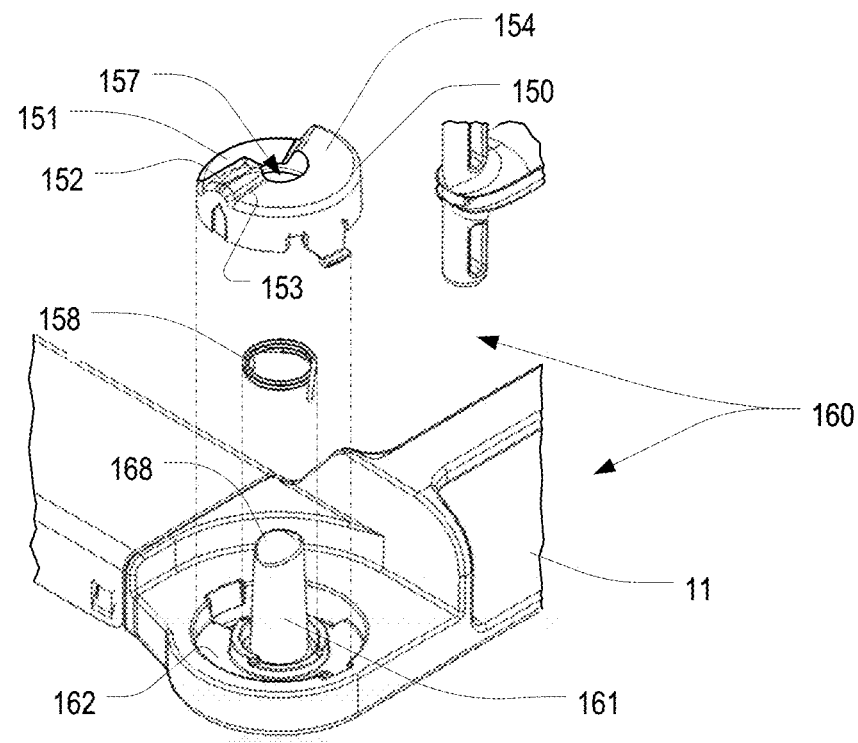
FIG. 54 is an enlarged view of portions of the view of FIG. 53, shown with the cross bar removed.
Figure 55:
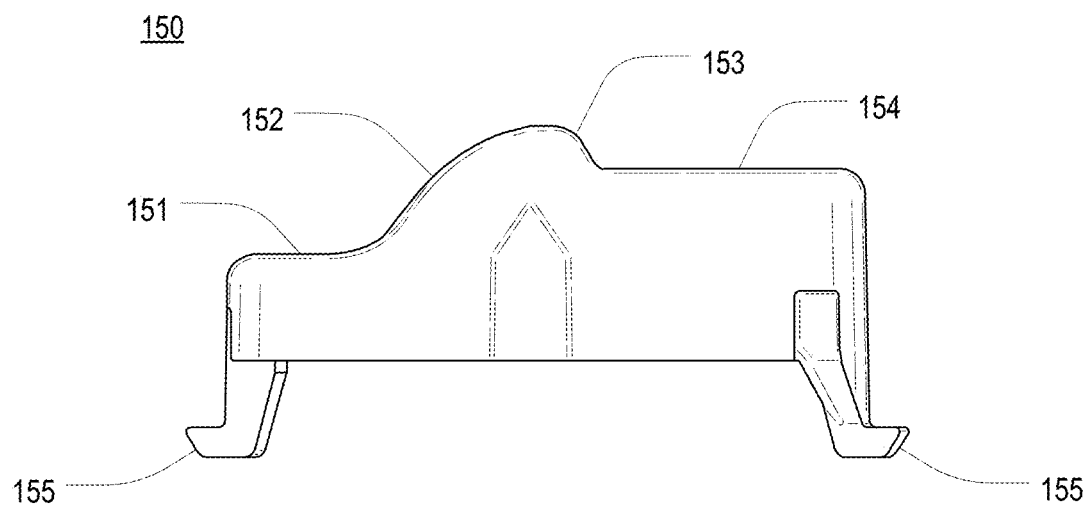
FIG. 55 is a side elevation view of the lifter disk of FIG. 54.
Figure 56:
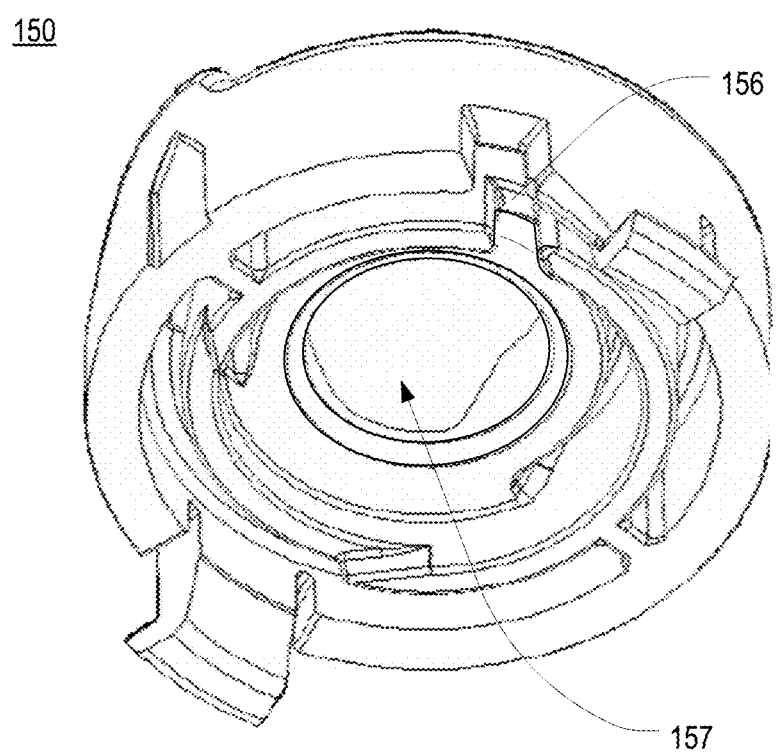
FIG. 56 is a bottom orthogonal view of the lifter disk of FIG. 54.
Figure 57:
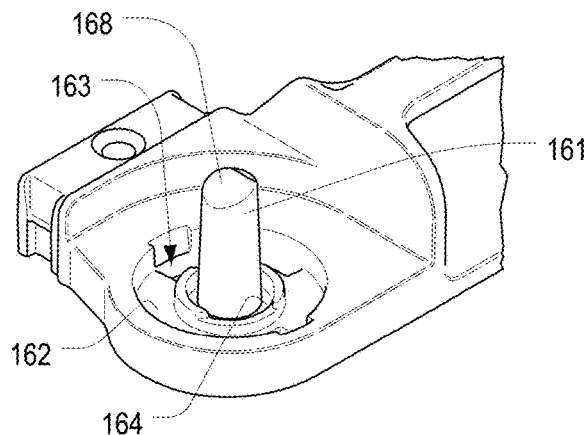
FIG. 57 is a fragmentary top isometric view of a portion of the distal end of the lower right support arm of FIG. 53.
Figure 58:
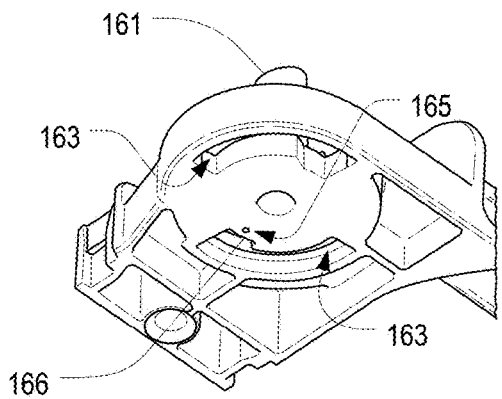
FIG. 58 is a fragmentary bottom isometric view of a portion of the distal end of the lower right support arm of FIG. 53.
Figure 59:
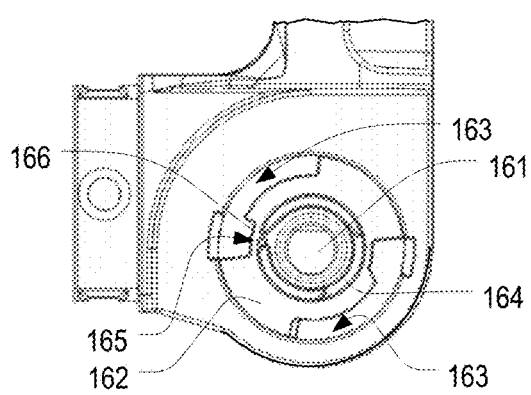
FIG. 59 is a fragmentary top plan view of a portion of the distal end of the lower right support arm of FIG. 53.
Figure 60:
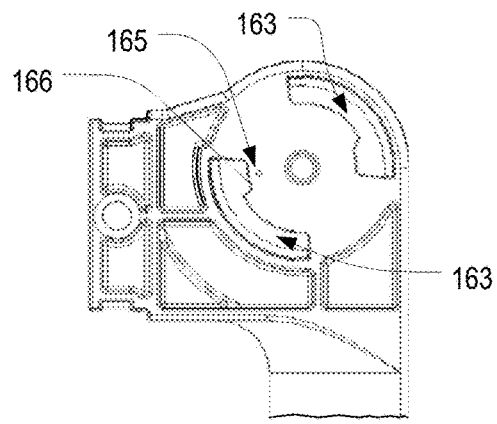
FIG. 60 is a fragmentary bottom plan view of a portion of the distal end of the lower right support arm of FIG. 53.

The door assembly 18 may be mounted between the support arms 11 by mounting the hinge assemblies 130 between upper and lower hinge mounts 160, each of which includes a lifter disk 150 or lifter blank 159 and a lifter nest 162. In this regard, FIG. 53 is a fragmentary, partially-exploded, isometric view of the lower portion of the cable manager 10 of FIG. 2, and FIG. 54 is an enlarged view of portions of the view of FIG. 53, shown with the cross bar 17 removed. As shown therein, a lifter disk 150 and corresponding torsion spring 158 are disposed in a lifter nest 162 at the end of each lower support arm 11. FIGS. 55 and 56 are a side elevation view and a bottom orthogonal view, respectively, of the lifter disk 150 of FIG. 54. (It will be appreciated that the lifter disk 150 in the lower left-hand corner of FIG. 53 is a mirror image of the lifter disk 150 in FIG. 54, and that some of related components are likewise left- or right-handed.) With reference to FIGS. 55 and 56, each lifter disk 150 includes a lower bearing surface 151, a lifting ramp 152, an engagement tooth 153, a raised bearing surface 154, a pair of snap tabs 155, a torsion spring arm catch 156, and a central opening 157. As shown in FIG. 54, the lower bearing surface 151, the lifting ramp 152, the engagement tooth 153, and the raised bearing surface 154 are arranged axially around the central opening 157.

Each lifter nest 162 is disposed in or at the end of a corresponding lower support arm 11. In this regard, FIGS. 57-60 are a fragmentary top isometric view, a fragmentary bottom isometric view, a fragmentary top plan view, and a fragmentary bottom plan view, respectively, of a portion of the distal end of the lower right support arm 11 of FIG. 53. (Although not illustrated, the upper support arms 11 are identical in at least some embodiments, except for left- and right-handedness, in order to simplify manufacturing and reduce unique part count, but the upper support arms may alternatively be uniquely designed.) Arranged in the lifter nest 162 are a hinge pin 161, a snap slot 163 for each snap tab 155 on the lifter disk 150, a torsion spring nest 164, a torsion spring end catch 165, and a snap catch 166 at the end of each snap slot 163. The lifter disk 150 is positioned in the lifter nest 162 such that the hinge pin 161 extends upward through the central opening 157 of the disk 150 and the snap tabs 155 extend through the snap slots 163 and are retained there. The torsion spring 158 is disposed in the torsion spring nest 164 with one end held in the torsion spring end catch 165 (shown as a hole, but other a notch or other structure may be used) and the other end held in the torsion spring arm catch 156 of the lifter disk 150 (visible in FIG. 56). In this arrangement, the lifter disk 150 can rotate around the axis of the hinge pin 161, as limited by the snap tabs 155 in the snap slots 163, but is biased in one direction by the torsion spring 158.

Each lifter disk 150 interfaces with the hinge body 133 and bolt 131 of a respective bottom hinge assembly 130. With particular reference to FIG. 51, the hinge body 133 includes an engagement tooth 147, a lower bearing surface 148, and an upper bearing surface 149. The profile of the engagement tooth 147 defines a lifting ramp 146. The door assembly 18 may be installed on the bottom hinge pins 161 by setting the bottom of the door onto the lower cross bar 17 so that the hinge pins 161 slide up into the hinge pin cavities 145. When the door assembly 18 is in installed and is positioned in its closed state (shown in FIG. 1), and when the lifter disk 150 is in its biased orientation, the lower bearing surface 148 of the hinge body 133 rests on the lower bearing surface 151 of the lifter disk 150 and the upper bearing surface 149 of the hinge body 133 rests on top of the lifting ramp 146/engagement tooth 147 with the lifting ramp 146 of the hinge body 133 in close proximity to the lifting ramp 152 of the lifter disk 150.

Figure 61:
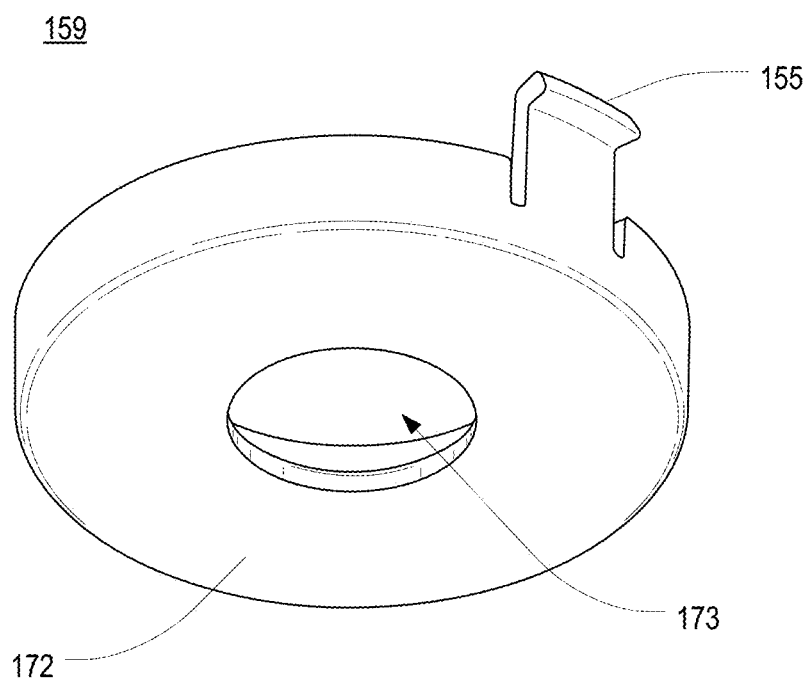
FIG. 61 is a bottom isometric view of a lifter blank from one of the upper support arms of FIGS. 1 and 2.

Although not illustrated in FIG. 53, a lifter blank 159 is disposed in or at the end of each upper support arm 11. In this regard, FIG. 61 is a bottom isometric view of a lifter blank 159 from one of the upper support arms 11 of FIGS. 1 and 2. The lifter blank 159 includes a bearing surface 172, a central opening 173, and a pair of snap tabs 155. Each lifter blank 159 is preferably disposed, in the orientation shown in FIG. 61, in a respective lifter nest 161 in the end of one of the upper support arms 11 such that the hinge pin 161 extends down through the central opening 173 of the blank 159. With the bottom of the door assembly 18 installed on the lower hinge pins 161, the upper end of the door assembly 18 may be installed on the upper hinge pins 161 by pushing the top of door assembly 18 toward the upper support arms 11 until the bolt strikes 144 make contact with the hinge pins 161. Because of the sloped surface of the bolt strike 144 and the sloped surface 168 on the top of the hinge pins 161, each bolt 131 is driven into its hinge body 133 (downward in the upper hinge assemblies 130), against the bias of the compression spring 132, until the bolt 131 clears the hinge pin 161. At this point, the bolt 131 springs outward again, driven by the compression spring 132, and the hinge pin 161 settles into the hinge pin cavity 145.

Once the door assembly 18 is installed, it may be opened along either side via the latch handle 111. When one of the latch handles 111 is rotated by a user, the corresponding gear 117 is likewise rotated (counterclockwise in FIG. 49), causing the racks 114 to be translated inward against the bias of the compression springs 116. Inward movement of the racks 114 also causes the lock rods 115 on the selected side of the door assembly 18 to be pulled inward. At their distal ends, the lock rod slots 140 pull on the internal pins 143 of the bolts 131, retracting the bolts 131 into the central cavities 135 of the hinge bodies 133. Once the bolts 131 have been retracted a sufficient distance to clear the hinge pins 161, the door assembly 18 can be pulled open and rotated about the hinge assemblies 130 on the opposite side of the door assembly 18.

Figure 62A:
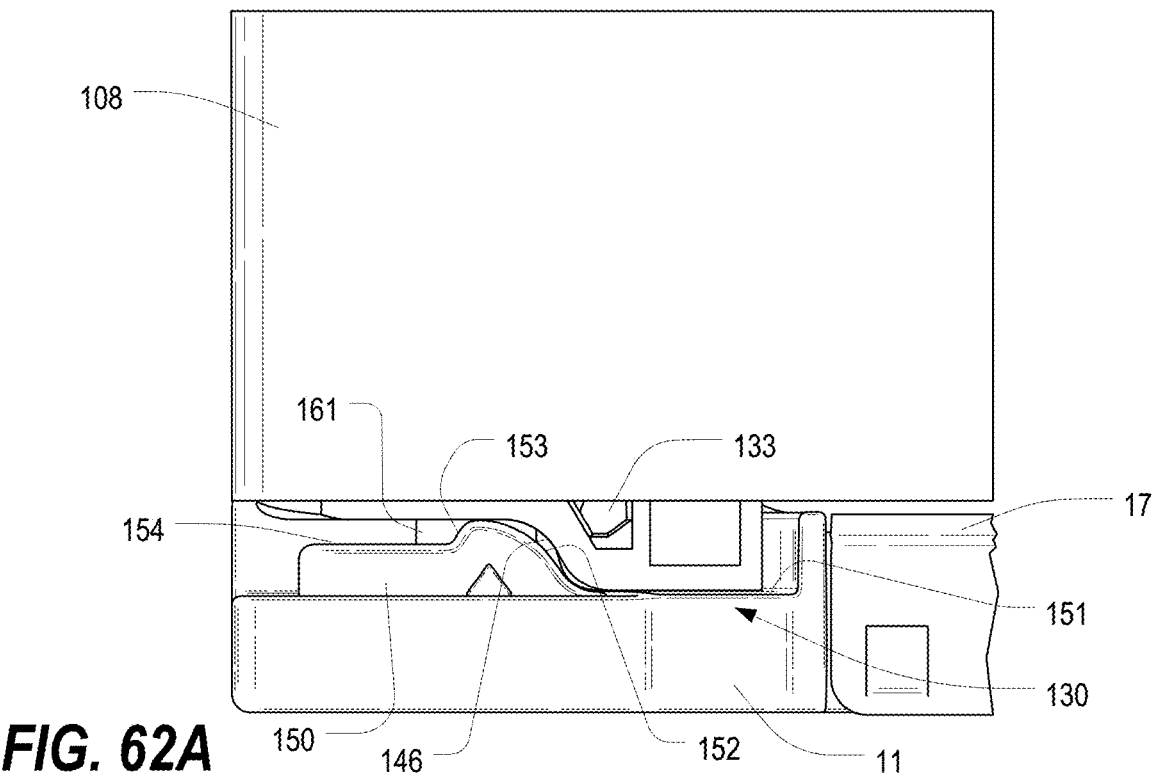
FIGS. 62A-66 are enlarged fragmentary front elevation views of the lower left corner of the cable manager of FIG. 1 with the door assembly shown in various states of operation.
Figure 62B:
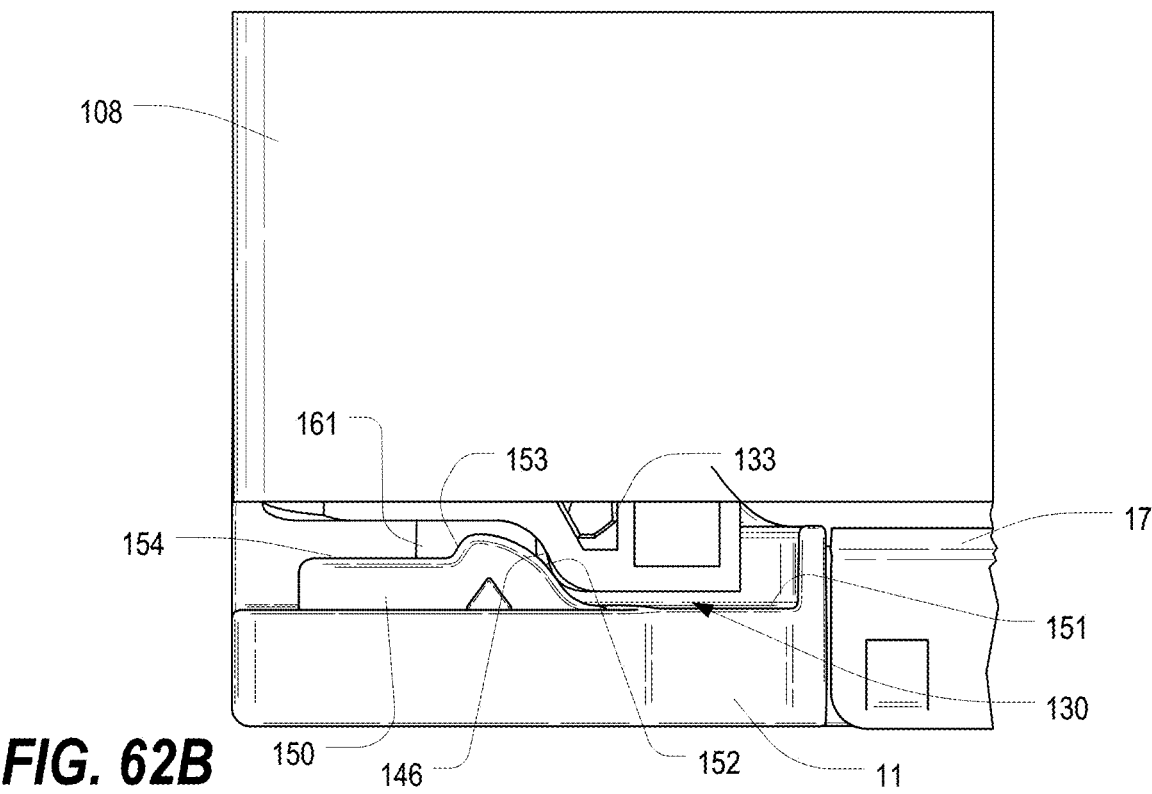
Figure 63:
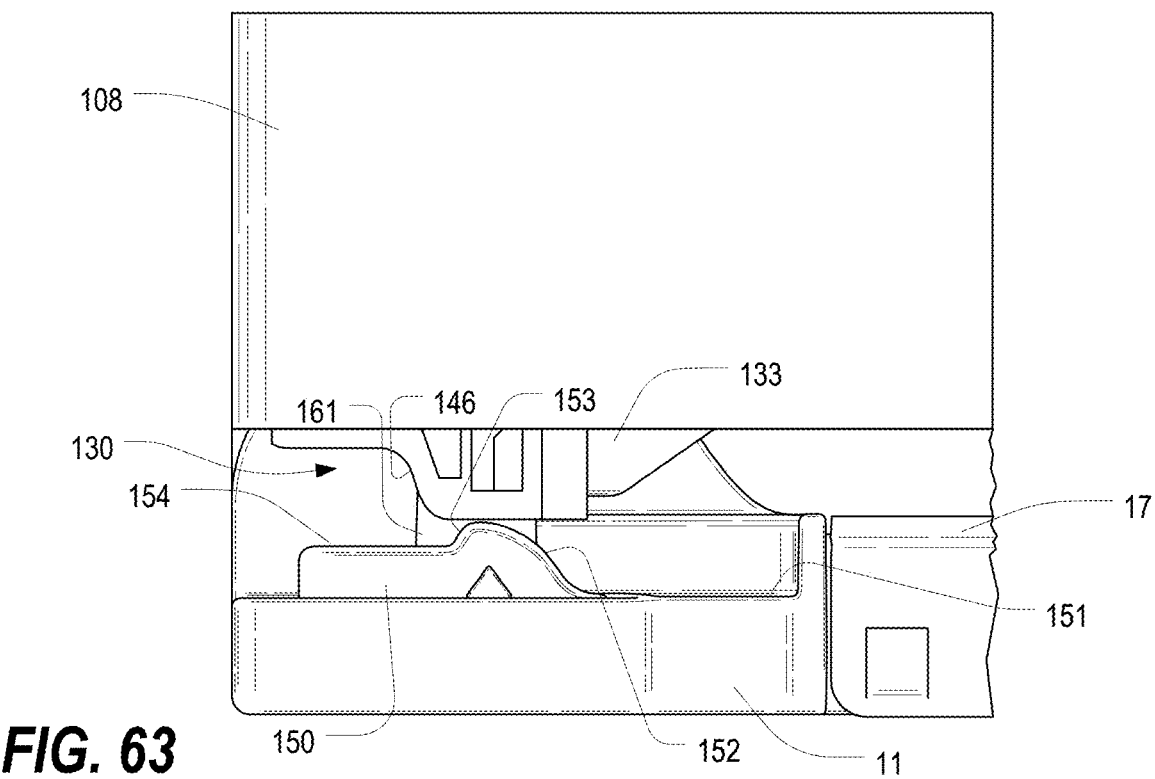
Figure 64:
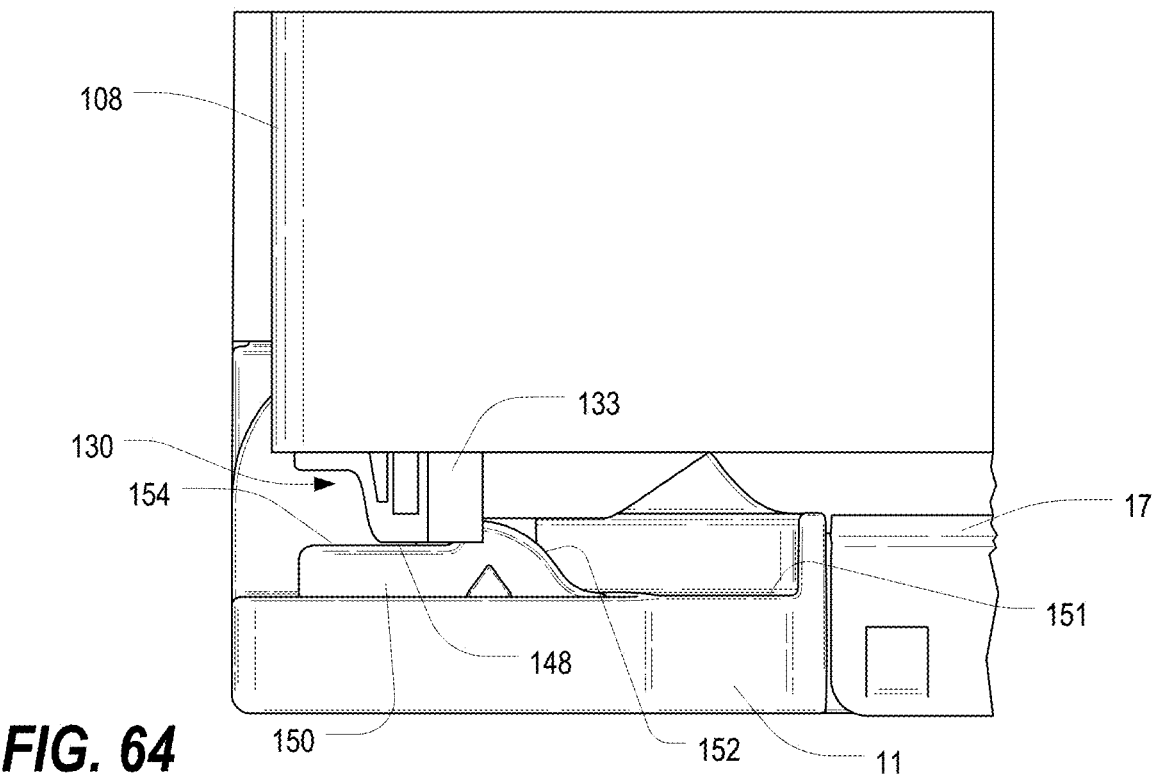
Figure 65:
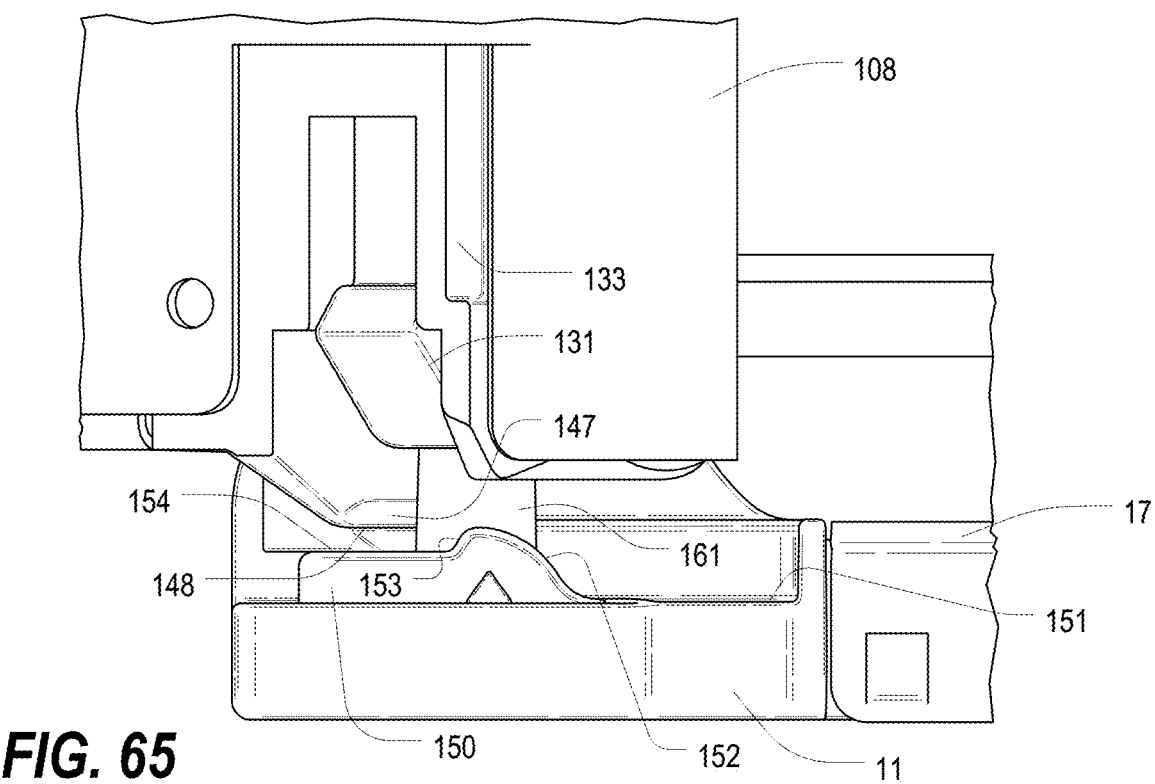
Figure 66:
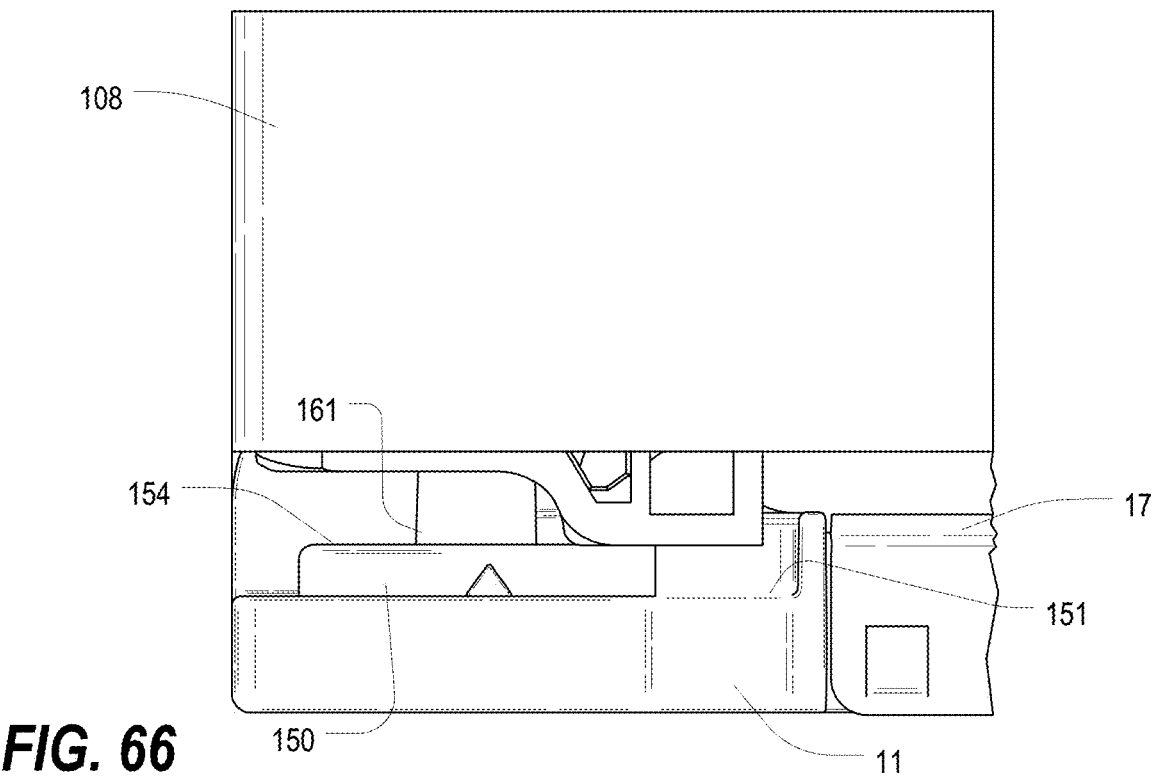

While the bolts 131 are being retracted along one side of the door assembly 18, the hinge assemblies 130, lifter disks 150, etc. along the other side of the door assembly 18 operate to facilitate rotation of the door assembly 18 about the hinge pins 161 with little interference from the bottom or sill of the door frame (i.e., the cross bar 17, the hinge area, etc). In this regard, FIGS. 62-66 are enlarged fragmentary front elevation views of the lower left corner of the cable manager 10 of FIG. 1 with the door assembly 18 shown in various states of operation. In FIG. 62, the door panel 108 is fully closed, the lifter disk 150 is in its natural state (i.e., rotated to its fullest extent by the torsion spring 158), and the hinge body 133 is resting on the lower bearing surface 151 of the lifter disk 150. As the door panel 108 is opened, the hinge assembly 130 rotates around the hinge pin 161, and the hinge body 133 is forced upward as its lifting ramp 146 makes contact with the lifting ramp 152 of the lifter disk 150, as shown in FIG. 62B. The hinge body 133 continues to be pushed upward by the lifting ramp 152 until it reaches the top thereof, as shown in FIG. 63. After that, further rotation of the door panel 108 moves the hinge body 133 past the engagement tooth 153 of the lifter disk 150 and allows the lower bearing surface 148 of the hinge body 133 to drop down onto the raised bearing surface 154 of the lifter disk 150, as shown in FIG. 64. The hinge body 133 can then be rotated freely on the raised bearing surface 154 of the lifter disk 150, thereby permitting the door panel 108 to be rotated it is fully open, as shown in FIG. 65.

Advantageously, the geometry of the lifting disk 150 and hinge body 133 serves to raise the bottom of the door panel 108 above the cross bar 17 during most of the opening process, thus minimizing or eliminating frictional interference or "rub" between the bottom of the door panel 108 and the cross bar 17. The ramp 152 of the disk 150 pushes the ramp 146 of the hinge body 133 upward, as shown in FIG. 62B, and once the hinge body 133 clears the top of the ramp 152 and drops down to rest on the raised bearing surface 154, the remainder of the opening process is smooth.

Notably, the lifter disk 150 generally remains stationary in its natural state during the entire opening process. However, when the door panel 108 starts to close, the engagement tooth 147 (visible in FIG. 65) of the hinge body 133 eventually makes contact with the engagement tooth 153 of the lifter disk 150 (the state shown in FIG. 64). At this point, the weight of the door panel 108 pushing down on the lifter disk 150 tends to lock the engagement teeth 147,153 together, and further closing movement of the door causes the lifter disk 150 to rotate with the rotation of the door, against the biasing force of the torsion spring). Because the hinge body 133 is carried on the raised bearing surface 154 of the lifter disk 150 as the lifter disk 150 rotates, the bottom of the door panel 108 remains elevated above the cross bar 17 and above the opposite side hinge area, thereby making it easier to close the door panel 180 without frictional interference. Notably, the hinge body 133 and the rest of the hinge assembly 130 remain elevated even when the door panel 108 is fully closed and latched on the opposite side. Only when the bolts 131 are retracted and the hinge assemblies 130 released from the hinge pins 161 (such as when a user wishes to open the door assembly 18 in the opposite direction) is the hinge body 130 released from the engagement tooth 153 of the lifter disk 150, at which point the torsion spring 158 biases the lifter disk 150 back to its natural state.

The latch assemblies 110, hinge assemblies 130, and hinge mounts 160 implement a latch mechanism by using a biased bolt and pin, thereby providing a slam function and keeping the door tightly closed. As described previously, the sloped surface of the bolt strike 144 collides with the sloped surface 168 of the pin 161, thereby forcing the bolt 131 into the hinge body 133 until the end of the bolt 131 clears the top of the pin 161, at which point it springs downward and traps the pin 161 in the hinge pin cavity 145.

Many variations in the design of the door assemblies 18 and the hinge assemblies 130 and corresponding hinge mounts 160. Parts shown herein may be made of specific materials, but could be made of any other material(s) that would be considered suitable or advantageous. In the particular design shown and described herein, the lifter disk 150 rotates relative to the end of the support arm 11, while the lifting ramp 146 is static relative to the hinge body 133. It will be appreciated, however, that these features could be switched, with a lifter disk (or its equivalent) carried by, and rotatable relative to, the hinge assembly or other portion of a door, and a lifting ramp that is mounted on, and static relative to, an end of the support arm.

In the particular design shown and described herein, the lifting function is achieved using a lifter disk, which is implemented as a rotational piece with a ramp and catch feature, wherein "tooth" geometry is provided on the hinge block and the lifter disk such that engagement between the structures rotates the lifter disk with the hinge when the door is closed. This tooth geometry is shown as an angled ramp surface with a radiused profile at the top and bottom of the ramp. In some embodiments, a rubber pad or other cushioning material or features could also be added in that area to soften the drop of the door during engagement of the teeth on the hinge and lifter. Furthermore, in various embodiments, the geometry could be changed in any way that still allows engagement and for the hinge and lifter to catch. Still further, in various embodiments, this function could be performed by any part on the frame or door that engages and disengages based on the current state of the door (opened left, opened right, closed, or the like). Such a part could, in various embodiments, rotate around an axis that is different from the one about which the door rotates, and in other embodiments could slide or otherwise move in a linear or other motion.

In the particular design shown and described herein, the lifter disk 150 is installed during general assembly of the cable manager 10 by simply snapping it into position, but in other embodiments it could also be attached by any other mechanical means that allows it to rotate. Likewise, the hinge assemblies are shown as being attached to the door using assembly screws 136 but could also be attached using another fastening method such as rivets or a snap feature. The hinge assemblies 130 and lifter disks 150 are shown as having left- and right-handed versions, but in other embodiments these elements could be designed to be the same on each side. Similarly, although the left- and right-handed hinge assemblies 130 are the same both top and bottom, in other embodiments they could be different. Still further, although lifter disks 150 are used at the bottom and lifter blanks 159 are used in corresponding locations at the top, in other embodiments they could be designed to be the same both top and bottom.

The latch mechanism shown uses a bolt and pin to allow a slam function and keep the door tightly closed. This also creates the axis around which the door hinges. However, in some embodiments, the latch mechanism could instead have a hinge pin on the door that is drawn up and down by the handle. This would interface with a corresponding hole, slot or feature on the frame to hold in place when engaged.

The latch currently uses a gear and rack assembly which is driven by a latch handle to pull the lock rods and lock bolts toward the center of the door. In some embodiments, however, this part of the design could be modified or replaced with any number of parts that perform the same function such as a simplified latch and lock rod assembly, a cable assembly, or any number of variations of latch assembly designs. The latch handle is shown as a lever on the rear face of the door, extending towards the outside edge. The handle, and corresponding latch assembly, could be placed on any face or edge of the door and be any geometry that allows a user to turn, lift, slide or otherwise move the latch handle to engage and disengage the latch assembly.

Advantageously, various embodiments of the cable manager design of the present invention use a rotating lifter to lift the door as it is opened. After the door is opened past a certain point, the hinge and the lifter engage and the hinge-side of the door is raised. The door is still in the raised state during the closing process, which enables the door to be closed without any interference with the frame or hinge area on the latching side. This allows the door to swing smoothly and freely, when closing, all the way through latch engagement. Subsequently, when the door is opened in the opposite direction, the previously engaged lifter finally returns to its natural position and the door is lifted onto the opposite lifter on the new hinge-side of the door. The invention also includes several aspects of improved functionality compared to previous door hinge designs, including smooth slam-latch capability. Various of these improvements are not limited to use with a cable manager door, but may be used in doors for other electronic equipment structures and even, in some cases, for other structures.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. A half-spool accessory installation in a cable manager, the half-spool accessory installation comprising:
    first and second half-spool accessories, each of which includes a curved support portion to provide a bend radius for cables, an end flange disposed at an end of the curved support portion, and one or more resilient snaps extending downwardly from the curved support portion; and
    an elongate support arm having a proximal end connected to the cable manager and a distal end extending into a cable management space, the support arm having a generally uniform cross-sectional shape along its length for accommodating the first and second half-spool accessories;
    wherein the one or more resilient snaps of the first half-spool accessory are engaged against corresponding ledges along a first side of the support arm, and the one or more resilient snaps of the second half-spool accessory are engaged against corresponding ledges along a second side of the support arm opposite of the first side, whereby the curved support portions of the first and second half-spool accessories together define a curved profile that substantially surrounds a section of the support arm.

2. The half-spool accessory installation of claim 1, wherein the curved profile is generally cylindrical-shaped.

3. The half-spool accessory installation of claim 1, wherein a position of each of the first and second half-spool accessories is independently adjustable along the length of the support arm.

4. The half-spool accessory installation of claim 1, wherein each of the first and second half-spool accessories includes one or more notches along side edges of the curved support portion to provide finger grips.

5. The half-spool accessory installation of claim 1, wherein each of the first and second half-spool accessories includes one or more standoffs extending downwardly from the curved support portion for positioning against the support arm.

6. The half-spool accessory installation of claim 1, wherein, for each of the first and second half-spool accessories, a connection between the curved support portion and the end flange is arcuate.

7. The half-spool accessory installation of claim 5, wherein the one or more standoffs of each of the first and second half-spool accessories each include a curved edge that interfaces with a corresponding curved surface of the support arm.

* * * * *